(12) United States Patent
Zischka et al.

(10) Patent No.: US 11,000,568 B2
(45) Date of Patent: May 11, 2021

(54) MEANS AND METHODS FOR TREATING COPPER-RELATED DISEASES

(71) Applicants: HELMHOLTZ ZENTRUM MÜNCHEN—DEUTSCHES FORSCHUNGSZENTRUM FÜR GESUNDHEIT UND UMWELT (GMBH), Neuherberg (DE); THE REGENTS OF THE UNIVERSITY OF MICHIGAN, Ann Arbor, MI (US); IOWA STATE UNIVERSITY RESEARCH FOUNDATION, INC., Ames, IA (US)

(72) Inventors: Hans Zischka, Munich (DE); Josef Lichtmannegger, Neuching (DE); Alan Angelo Dispirito, Ames, IA (US); Jeremy David Semrau, Ann Arbor, MI (US)

(73) Assignees: HELMHOLTZ ZENTRUM MÜNCHEN—DEUTSCHES FORSCHUNGSZENTRUM FÜR GESUNDHEIT UND UMWELT (GMBH), Neuhergerg (DE); IOWA STATE UNIVERSITY RESEARCH FOUNDATION, Ames, IA (US); THE REGENTS OF THE UNIVERSITY OF MICHIGAN, Ames, IA (US)

(*) Notice: Subject to any disclaimer, the term of this patent is extended or adjusted under 35 U.S.C. 154(b) by 0 days.

(21) Appl. No.: 16/063,220

(22) PCT Filed: Dec. 16, 2016

(86) PCT No.: PCT/EP2016/081407
§ 371 (c)(1),
(2) Date: Jun. 15, 2018

(87) PCT Pub. No.: WO2017/103094
PCT Pub. Date: Jun. 22, 2017

(65) Prior Publication Data
US 2019/0328835 A1 Oct. 31, 2019

(30) Foreign Application Priority Data
Dec. 18, 2015 (EP) .................... 15201070
Feb. 19, 2016 (LU) ...................... 92979

(51) Int. Cl.
*A61K 38/16* (2006.01)
*A61P 1/16* (2006.01)

(52) U.S. Cl.
CPC .............. *A61K 38/164* (2013.01); *A61P 1/16* (2018.01)

(58) Field of Classification Search
CPC .. A61K 31/30; A61K 31/315; A61K 31/4166; A61K 38/164; A61P 1/16; A61P 21/02; A61P 25/00; A61P 25/14; A61P 25/16; A61P 25/28; A61P 29/00; A61P 31/04; A61P 31/10; A61P 35/00; A61P 35/02; A61P 39/02; A61P 39/04; A61P 3/10; A61P 43/00
See application file for complete search history.

(56) References Cited

U.S. PATENT DOCUMENTS

| 7,199,099 B2 * | 4/2007 | DiSpirito | C07K 5/1008 514/15.1 |
|---|---|---|---|
| 8,735,538 B1 | 5/2014 | DiSpirito et al. | |
| 2004/0171519 A1 * | 9/2004 | DiSpirito | C07K 5/1008 514/2.4 |

FOREIGN PATENT DOCUMENTS

WO   WO 2004/056849 A2   7/2004

OTHER PUBLICATIONS

Summer et al. The biogenic methanobactin is an effective chelator for copper in a rat model for Wilson disease. Journal Trace Elements in Medicine and Biology, 2011. vol. 25, pp. 36-41. (Year: 2011).*
Summer et al. The biogenic methanobactin is an effective chelator for copper in a rat model for Wilson Disease. Journal of Trace Elements in Medicine and Biology, 2011. vol. 25, pp. 36-41. (Year: 2011).*
Lichtmanneger et al. Methanobactin reverses acute liver failure in a rat model of Wilson disease. The Journal of Clinical Investigation. Jul. 2016, vol. 126, No. 7, pp. 2721-2735. (Year: 2016).*
Bandow et al. Spectral and copper binding properties of methanobactin from the facultative methanotroph Methylocystis strain SB2. J Inorg Biochem, 2012, vol. 110. pp. 72-82. (Year: 2012).*
Staph Infection Resources. Staph and MRSA linked to yeast and fungal infections.Jun. 17, 2011. Accessed online at https://www.staph-infection-resources.com/blog/secondary-yeast-candida-fungal-infections/ on Feb. 27, 2020. (Year: 2011).*
European Office Action for Patent Application No. 16823220.5, dated Dec. 10, 2019, 6 pages.

(Continued)

*Primary Examiner* — Marcela M Cordero Garcia

(57) ABSTRACT

The present invention relates to the field of (bio-)medicine, and more particularly to the treatment of copper-related diseases. Novel means and methods for depleting (excess) copper from organs and/or the circulation are provided. Agents with a high copper binding affinity and stabilized forms thereof are provided, as well as a novel treatment regimen. The means and methods of the present invention are particularly useful for treatment of Wilson Disease, but also for treatment of other conditions.

31 Claims, 27 Drawing Sheets
Specification includes a Sequence Listing.

(56) References Cited

OTHER PUBLICATIONS

Kenney and Rosenzweig, "Chemistry and Biology of the Copper Chelator Methanobactin," ACS Chemical Biology 7(2):260-268 (2012).

Pesch et al., "Copper complexation of methanobactin isolated from *Methylosinus trichosporium* OB3b: pH-dependent speciation and modeling," Journal of Inorganic Biochemistry 116:55-62 (2012).

Pesch et al., "Competitive ligand exchange between Cu-humic acid complexes and methanobactin," Geobiology 11:44-54 (2013).

Schilsky,"Treatment of Wilson's Disease: What Are the Relative Roles of Penicillamine, Trientine, and Zinc Supplementation?" Current Gastroenterology Reports 3:54-59 (2001).

Choi et al., "Spectral and thermodynamic properties of Ag(I), Au(III), Cd(II), Co(II), Fe(III), Hg(II), Mn(II), Ni(II), Pb(II), U(IV), and Zn(II) binding by methanobactin from Methylosinus trichosporium OB3b," *Journal of Inorganic Biochemistry* 100: 2150-2161, 2006.

\* cited by examiner

Figure 4 (cont'd)
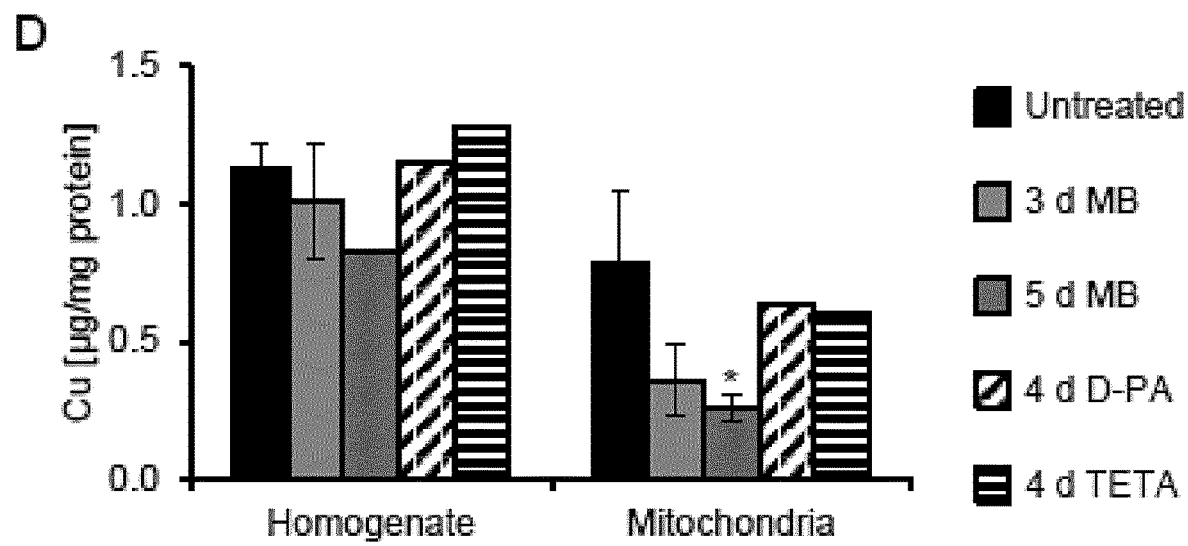
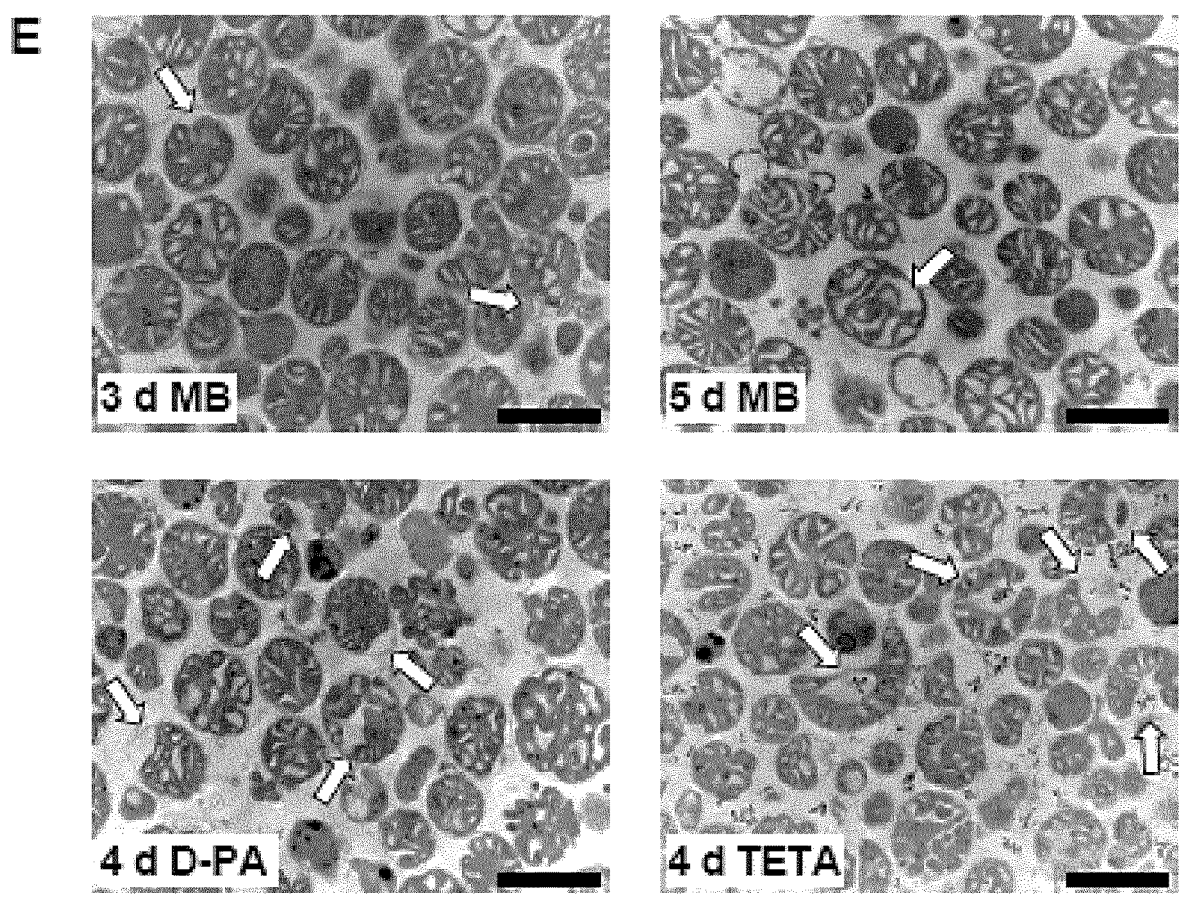

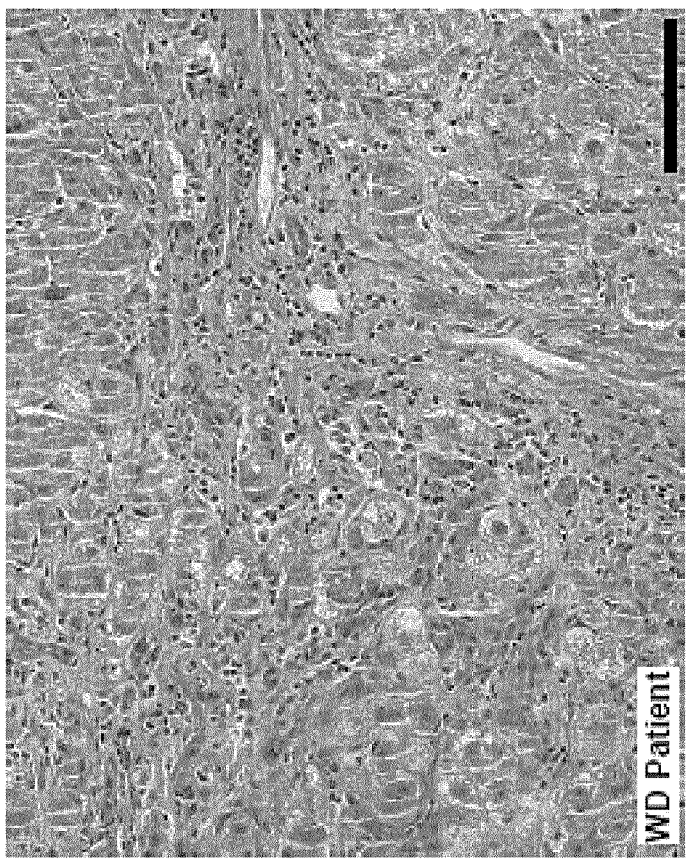
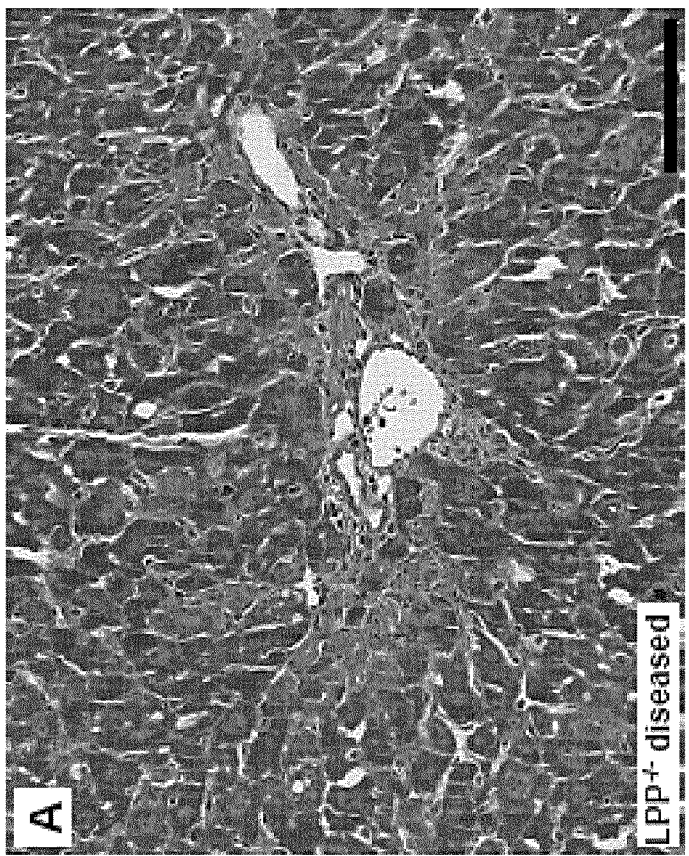
Figure 6

Figure 9
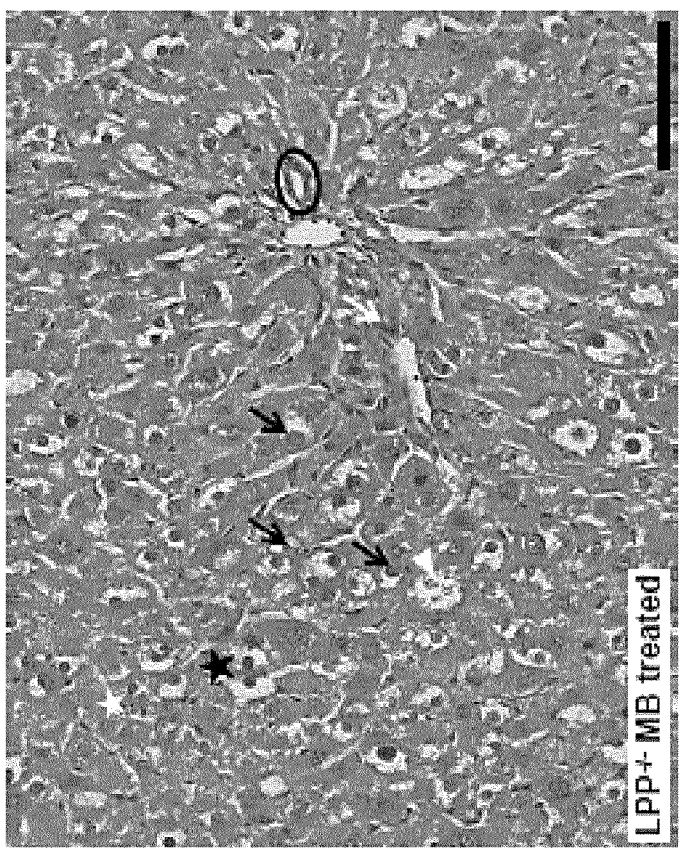
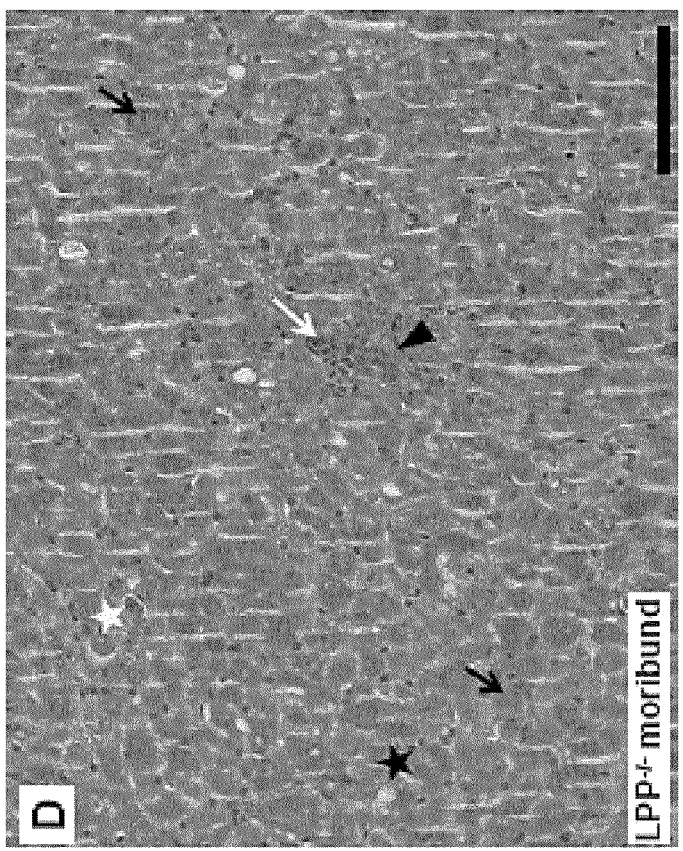

Figure 9 (cont'd)
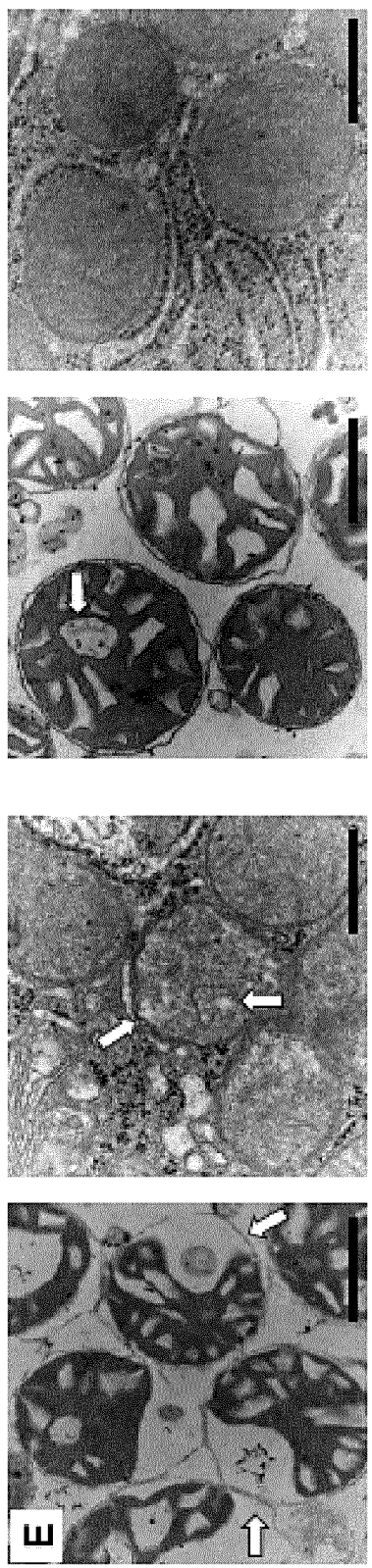
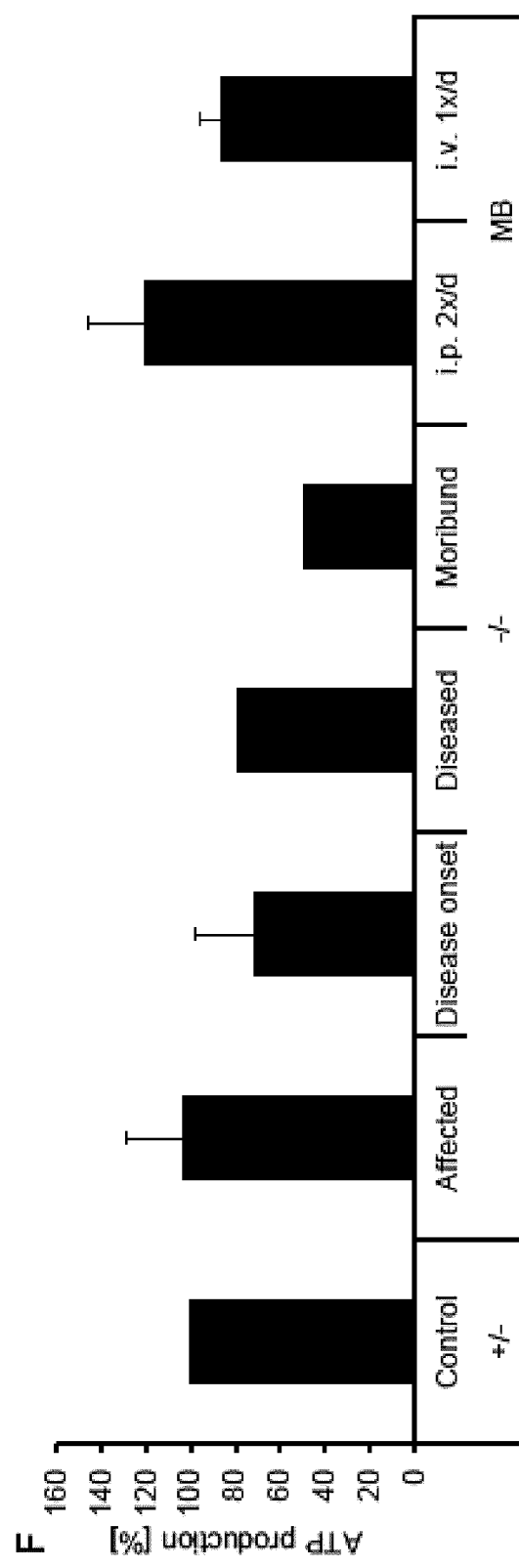

Figure 10

| Group Sex, Rat(s) | Age [d] | Weight [g] Start | Weight [g] End | AST [U/L] Start | AST [U/L] End | Bilirubin [mg/dl] Start | Bilirubin [mg/dl] End | Copper [ng/mg protein] Homogenate | Copper [ng/mg protein] Mitochondria | Mitochondrial Cu depletion[a] [%] |
|---|---|---|---|---|---|---|---|---|---|---|
| A | | | | | | | | | | |
| Control (+/-) | | | | | | | | | | |
| f, N=15 | 83-146 | - | 170±13 | - | 115±28 | - | < 0.5 | 14±2 | 27±2 | - |
| m, N=11 | 75-95 | - | 274±36 | - | 123±35 | - | < 0.5 | 17±4 | 53±16 | - |
| Affected (-/-) | | | | | | | | | | |
| f, N=4 | 85-92 | - | 165±16 | - | 138±37 | - | < 0.5 | 1353±137 | 415±84 | - |
| m, N=11 | 66-93 | - | 253±25 | - | 151±33 | - | < 0.5 | 1188±196 | 464±248 | - |
| Disease onset (-/-) | | | | | | | | | | |
| f, N=5 | 83-93 | - | 146±10 | - | 315±53 | - | < 0.5 | 1477±211 | 566±35 | - |
| m, N=6 | 80-107 | - | 275±45 | - | 244±44 | - | < 0.5 | 1337±155 | 476±159 | - |
| Diseased (-/-) | | | | | | | | | | |
| f, N=1 | 84 | - | 162 | - | 590 | - | 0.5 | 1389 | 670 | - |
| m, N=4 | 91-107 | - | 274±20 | - | 412±124 | - | 1.3±1.1 | 1389±79 | 1129±328 | - |
| Moribund (-/-) | | | | | | | | | | |
| f, N=3 | 97-106 | - | 140±5 | - | 454±96 | - | 14.2±5.5 | 1667±478 | 1398±301 | - |
| m, N=1 | 95 | - | 255 | - | 570 | - | 8.0 | 1261 | 1602 | - |
| B | | | | | | | | | | |
| MB 5x i.p. (-/-) | | | | | | | | | | |
| f, rat 1 (A) | 91 | 157 | 154 | 116 | 87 | < 0.5 | < 0.5 | - | 205 | 50.7 |
| m, rat 2 (Do)[b] | 90 | 197 | 205 | 480 | 194 | < 0.5 | < 0.5 | 806 | 321 | 32.4 |
| m, rat 3 (Do) | 90 | 231 | 242 | 270 | 160 | < 0.5 | < 0.5 | 851 | 251 | 47.2 |
| f, rat 4 (D) | 95 | 160 | 164 | 369 | 127 | 0.6 | < 0.5 | 915 | 432 | 35.6 |
| C | | | | | | | | | | |
| MB 5x i.v. (-/-) | | | | | | | | | | |
| f, rat 1 (D) | 92 | 135 | 143 | 295 | 155 | 1.5 | < 0.5 | 928 | 532 | 20.6 |
| f, rat 2 (Do) | 92 | 150 | 161 | 70 | 107 | 1.2 | < 0.5 | 1265 | 391 | 31.0 |
| m, rat 3 (Do) | 81 | 234 | 240 | 97 | 98 | 1.6 | < 0.5 | 721 | 173 | 63.7 |
| D | | | | | | | | | | |
| MB 16x i.p. (-/-) | | | | | | | | | | |
| f, rat 1 (D) | 89 | 148 | 155 | 365 | 182 | 1.0 | < 0.5 | 455 | 241 | 64.0 |
| f, rat 2 (D) | 89 | 144 | 160 | 570 | 178 | 0.9 | < 0.5 | 315 | 218 | 67.4 |
| f, rat 3 (M) | 90 | 120 | 155 | 610 | 122 | 15.5 | < 0.5 | 220 | 203 | 85.5 |
| f, rat 4 (Do) | 90 | 143 | 163 | 273 | 131 | < 0.5 | < 0.5 | 513 | 206 | 63.6 | a: Calculated to respective untreated group
b: Abbreviations are A: Affected, Do: Disease onset, D: Diseased, M: Moribund

Figure 11
A: *Methylosinus trichosporium* OB3b
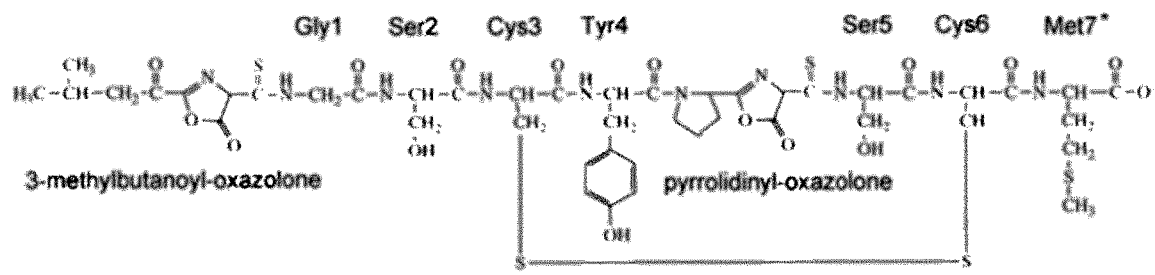
B: *Methylocystis* strain M
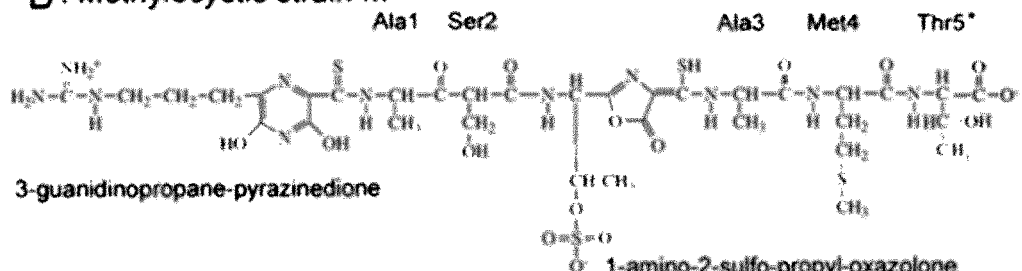
C: *Methylocystis hirsuta* CSC1
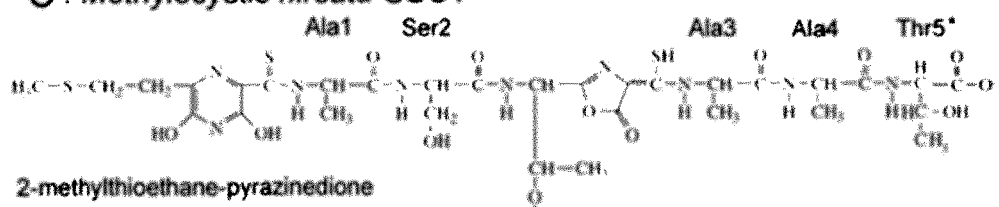
D: *Methylocystis rosea*
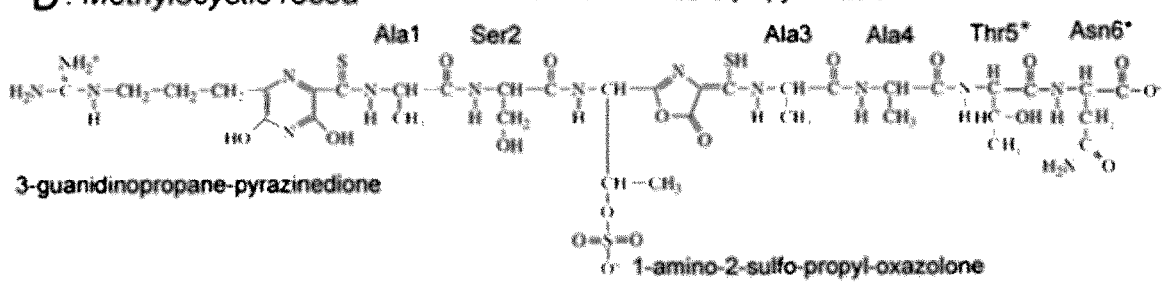
E: *Methylocystis* strain SB2
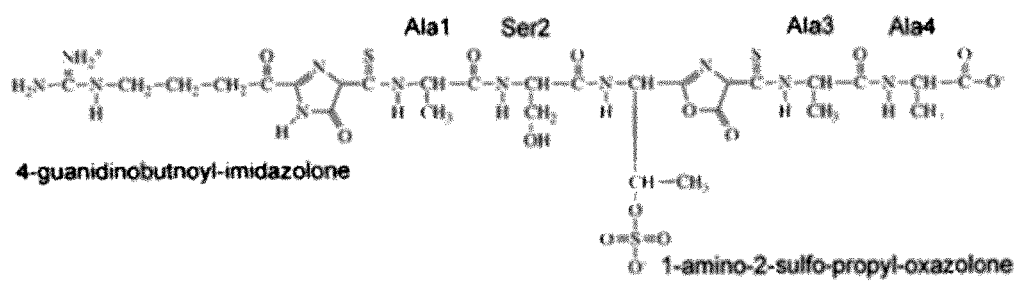

Figure 12

|  | leader peptide | core peptide | SEQ ID NO. |
|---|---|---|---|
| I | | | |
| mb-OB3b: | MTVKIAQKKVLPVIGRAAAL | GSCYPCSCM | (SEQ ID NO.1) |
| mb-LW3 v1: | MAIKIAKKEVLPVVGRLGAM | CSSCPMCHCGPLCP | (SEQ ID NO.2) |
| mb-LW5 v1: | MAIKISKKEVLPVVGRLGAM | CSSCPMCGPLCP | (SEQ ID NO.3) |
| mb-PW1: | MAIKIAKKEVLPVVGRLGAM | CSSCPMCGPLCP | (SEQ ID NO.4) |
| mb-LW4: | MTIKVVKKEILPVIGRVQAM | CACNPPWCGTC | (SEQ ID NO.5) |
| mb-OBBP v1: | MAIKIVKKEILPVIGRVQAP | CSSCSGGGCCGCGPA | (SEQ ID NO.18) |
| II | | | |
| mb-SB2: | MTIRIAKRITLNVIGRASAR | CASTCAATNG | (SEQ ID NO.7) |
| mb-rosea: | MTIRIAKRITLNVIGRASAR | CASTCAATNG | (SEQ ID NO.8) |
| mb-SC2: | MTIRIAKRITLNVIGRASAM | CASTCAATNG | (SEQ ID NO.9) |
| mb-OBBP v2: | MTIKIVKRTALAVNGRAGAD | CGTACWA | (SEQ ID NO.10) |
| mb-LW5 v2: | MAINIVKRTTLVVNGRTGAD | CGTACWG | (SEQ ID NO.11) |
| mb-LW3 v2: | MAINIVKRTTLVVNGRSGAD | CGTACWG | (SEQ ID NO.12) |
| mb-mobilis: | MSIKISARKALQIAGRAGAR | CATICAVAG | (SEQ ID NO.13) |
| mb-B-8: | MTIKISKKEAIEVRGRSGAC | CGSCCAAIGA | (SEQ ID NO.14) |
| mb-14-3: | MSIKIAKKHTLQIAGRAGAC | CASCCAPLGVN | (SEQ ID NO.15) |
| mb-B510: | MTIKIAKKQTLSVAGRAGAC | CGSCCAPVGVN | (SEQ ID NO.16) |
| mb-21721: | MKIKVTKKTTMTVAGRAGAC | CASCCAPVGVN | (SEQ ID NO.17) |

Figure 13
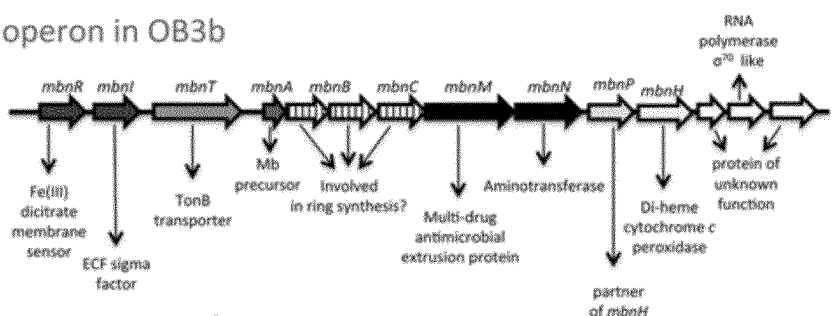
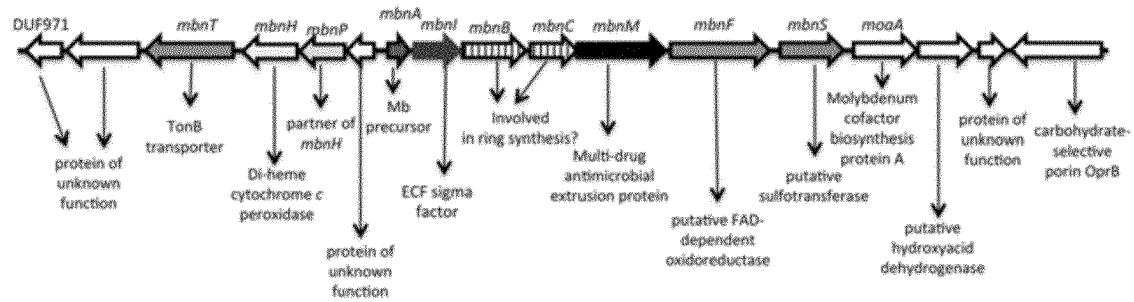

Figure 14

| Experimental day | 1 | 5 | 8 | | 29 | 33 | 36 | | | | 85 |
|---|---|---|---|---|---|---|---|---|---|---|---|
| Treatment | 3x MB/d | | Observation | | 3x MB/d | | Observation | | | | |
| Rat pair | 1 | 2 | | | 3 | 4 | | | | | 5 |

| Rat pair | 1 | | 2 | | 3 | | 4 | | 5 | |
|---|---|---|---|---|---|---|---|---|---|---|
| LPP genotype | +/- | -/- | +/- | -/- | +/- | -/- | +/- | -/- | +/- | -/- |
| Age [d] | 82 | 82 | 89 | 89 | 109 | 109 | 117 | 116 | 166 | 166 |
| Sex | F | F | F | F | F | F | M | M | M | M |
| Ceruloplasmin [U/L] | 234 | 8 | 227 | 1 | 194 | 1 | 163 | 0 | 188 | 0 |
| AST [U/L] Start | - | - | - | 88 | - | 110 | - | 94 | - | 88 |
| AST [U/L] End | 118 | 113 | 93 | 88 | 78 | 86 | 90 | 83 | 137 | 109 |
| Body weight [g] Start | - | - | - | 156 | - | 151 | - | 258 | - | 278 |
| Body weight [g] End | 170 | 179 | 163 | 155 | 186 | 177 | 349 | 291 | 413 | 357 |
| Cu [µg/mg protein] | | | | | | | | | | |
| Homogenate | 0.013 | 0.917 | 0.014 | 0.593 | 0.012 | 1.001 | 0.013 | 0.226 | 0.014 | 1.019 |
| Mitochondria | 0.028 | 0.296 | 0.027 | 0.167 | 0.027 | 0.267 | 0.028 | 0.067 | 0.023 | 0.266 |

MEANS AND METHODS FOR TREATING COPPER-RELATED DISEASES

GOVERNMENT STATEMENT OF INTEREST

This invention was made with government support under grant DE-SC0006630 awarded by the U.S. Department of Energy. The government has certain rights in the invention.

CROSS-REFERENCES TO RELATED APPLICATIONS

This application is a U.S. national phase application of International PCT Patent Application No. PCT/EP2016/081407, which was filed on Dec. 16, 2016, which claims priority to Luxembourg Application No. 92979, filed Feb. 19, 2016, and European Application No. 15201070.8, filed Dec. 18, 2015. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is SCHI_007_00USa_ST25.txt. The text file is 7 KB, created on Jun. 2, 2020, and is being submitted electronically via EFS-Web.

BACKGROUND

Copper is an essential trace element for eukaryotes and most prokaryotes that plays an important role in critical biological functions such as enzyme activity, oxygen transport and cell signaling. However, due to its high redox activity and its ability to catalyze the production of free radicals, copper can have detrimental effects on lipids, proteins, DNA and other biomolecules. Particularly, mitochondria are thought to be the major targets for oxidative damage resulting from copper toxicity. Moreover, copper can interfere with proteins and can displace other metals such as zinc from metalloproteins, thereby inhibiting their activity. In order to prevent copper from exerting its potentially toxic effects, it usually does not exist in free form, but only as a complex. In the human body, approximately 95% of the copper in plasma is bound to proteins such as ceruloplasmin, a multicopper ferroxidase that is synthesized and secreted by hepatocytes. It is estimated that less than 1 atom of free copper is present per cell.

Due to its ambivalent role in metabolism, any imbalance in copper bioavailability inevitably leads to deficiency or toxicity, and all organisms have evolved mechanisms that regulate its absorption, excretion and bioavailability. In mammals, copper absorption occurs in the small intestine via enterocyte uptake, followed by its transfer into the blood by the copper transporter ATP7A. The liver plays a critical role in copper metabolism, serving both as the site of copper storage and regulating its distribution to serum and tissues and excretion of excess copper into the bile. Particularly, hepatocytes transport and regulate physiological copper via the specialized transporter ATP7B.

ATP7A and ATP7B are closely related in structure and function, with approximately 60% amino acid sequence identity. They undergo ATP-dependent cycles of phosphorylation and dephosphorylation to catalyze the translocation of copper across cellular membranes for the metallation of many essential cuproenzymes, as well as for the removal of excess cellular copper to prevent toxicity.

ATP7B mutations result in a major impairment in the ability of hepatocytes to maintain copper homeostasis at the cellular and systemic levels, resulting in impaired biliary copper excretion and persistent copper accumulation in the liver, a condition known as Wilson disease (WD). This can lead—most likely due to the spillover of liver copper (Bandmann et al., The Lancet. Neurology 14, 103-113 (2015))—to deleterious effects on the brain and in many cases to chronic liver disease but also to fulminant hepatic failure (Gitlin, *Gastroenterology* 125, 1868-1877 (2003).

Untreated Wilson Disease is universally fatal, with most patients dying from liver disease. In order to restore body copper homeostasis, the clinically used copper chelators D-penicillamine (D-PA) and trientine (TETA) or the candidate drug tetrathiomolybdate (TTM) are administered daily (Gitlin J D, *Gastroenterology*. 2003 December; 125(6): 1868-77). This lifelong therapy is effective only if commenced before the onset of advanced hepatic or neurologic disease (Roberts et al., *Am J Clin Nutr* 88, 851S-854S (2008)). The same holds true for zinc salts, which are primarily used in mild cases of WD to decrease copper absorption via the gastrointestinal tract or as copper maintenance therapy in chelator treated WD patients (Gitlin J D, loc. cit.). However, in circumstances of acute liver failure—caused by either delayed diagnosis, treatment failure, or rapidly developing fulminant hepatitis—death is almost certain unless liver transplantation is performed (Gitlin J D, loc. cit.). All of the currently FDA/EMA-approved copper chelators have severe adverse effects, including bone marrow toxicity, nephrotoxicity, hepatotoxicity, anemia and triggering of autoimmune disease (Gitlin J D, loc. cit.). Due to the toxicity of D-PA, discontinuation of treatment is required in almost one third of WD patients (Weiss & Stremmel, *Current gastroenterology reports* 14, 1-7 (2012)).

Currently approved pharmacological treatments usually fail to restore copper homeostasis in acute WD, thus rendering liver transplantation the only viable treatment option. Given these issues, there is a clear unmet medical need for an alternative and innovative treatment of WD and other copper-related disease. The technical problem underlying the present application is to comply with the unmet medical need for an alternative and innovative treatment of copper-related disease, such as WD, particularly acute WD.

SUMMARY

The present inventors, for the first time, suggest—based on the unexpected capability of methanobactin to massively deplete copper from hepatocytes and hepatocyte mitochondria—(1) a novel treatment regimen involving phases of copper depletion followed by phases of non-treatment, (2) a novel treatment of (previously difficult-to-treat or untreatable) acute phase Wilson Disease and (3) a stabilized form of methanobactin that retains the superior capabilities of unstabilized Methanobactin (and is thus suitable for use in accordance with the treatment regimen and medical indication set out above) but offers the benefit of increased stability at body temperature.

Methanobactins are low molecular mass copper-binding molecules produced by many methanotrophic bacteria and have been demonstrated to mediate copper acquisition from the environment (Semrau et al., 2010. FEMS Microbiol. Rev 34:496-531). For the first time, the present inventors have demonstrated that methanobactins hold considerable potential for treatment of a variety of copper-related diseases and conditions, and, due to their excellent copper binding affinities (Choi et al., 2006. Biochemistry 45: 1442-1453) and tolerance in vivo, are promising new agents for a massive and fast depletion of excess copper levels in patients in need thereof. Due to their beneficial properties, methanobactins are considered to be particularly useful for acute de-coppering therapy in Wilson Disease patients.

Thus, in a first aspect, the present invention relates to a copper-binding methanobactin for use in a method of treatment of Wilson Disease in a subject, wherein treatment comprises a treatment cycle of (a) a first phase of methanobactin administration followed by (b) a second phase of non-treatment, wherein the second phase exceeds the first phase. Said first phase may last for a period of 1, 2, 3, 4, 5, 6, 7, 8, 9, 10 or more consecutive days, and may involve administration of methanobactin in single doses once daily, twice daily, three times daily, four times daily, every other day or continuously. The second phase may last for at least 1 week, 2 weeks, 3 weeks, 4 weeks, 5 weeks, or more. At least one further treatment cycle may follow on the second phase of non-treatment of the treatment cycle. Particularly, treatment according to the method of the invention may comprise continuous treatment cycles.

In a further aspect, the present invention also relates to copper-binding methanobactin for use in a method of treatment of acute phase Wilson Disease in a subject.

In any event, the methanobactin for the uses of the invention may comprise or consist of the following general formula (I):

wherein
R1 and R2 are each a 5-membered heterocycle comprising N and associated with an enethiolate;
and each X is independently selected from any amino acid.

It is further contemplated that the methanobactin may be derived from bacteria, including methanotroph and non-methanotroph bacteria, such as *Methylocystis* spec., *Methylosinus* spec., *Methylomicrobium* spec. and *Methylococcus* spec. For instance, the methanobactin may be selected from (a) a *Methylosinus trichosporium* OB3b methanobactin (mb-OB3b) (b) a *Methylocystis* strain SB2 methanobactin (mb-SB2), (c) a *Methylococcus capsulatus* Bath methanobactin (mb-Bath) (d) a *Methylomicrobium album* BG8 methanobactin (mb-BG8), (e) a *Methylocystis* strain M methanobactin, (f) a *Methylocystis hirsuta* CSC1 methanobactin and (g) a *Methylocystis rosea* methanobactin (mb-*rosea*), (h) a *Methylosinus* sp. strain LW3 methanobactin (mb-LW3), (i) a *Methylosinus* sp. strain LW4 methanobactin (mb-LW4), (j) a *Methylocystis* sp. strain LW5 (mb-LW5), (k) a *Methylosinus* sp. strain PW1 methanobactin (mb-PW1), (l) a *Methylocystis parvus* OBBP methanobactin (mb-OBBP), (m) a *Cupriavidus basiliensis* B-8 methanobactin (mb-B-8), (n) a *Pseudomonas extremaustralis* 14-3 methanobactin (mb-14-3), (o) a *Azospirillum* sp. stain B510 methanobactin (mb-B510), (p) a *Tistrella mobilis* KA081020-065 (mb-*mobilis*) methanobactin and (q) a *Comamonas composti* DSM 21721 methanobactin (mb-21721).

The methanobactin for the uses of the invention is envisaged to bind copper, in particular Cu(I), with a $K_d$ of $10^{-15}$ or less.

Said methanobactin may be complexing Zn(I) and/or Zn(II).

In a further aspect, the present invention provides a pharmaceutical composition comprising a stabilized methanobactin. Said pharmaceutical composition may be stable at 37° C. for at least 20 hours or more. Stabilization may be achieved by a) providing the pharmaceutical composition at a pH of ≥9 and/or by providing the methanobactin in the form of a complex with Zn(I) and/or Zn(II). Said zinc:methanobactin complex may be prepared by contacting an amount of Zn(I) and/or Zn(II) and an amount of methanobactin in a ratio of 1:1 in aqueous solution. The pharmaceutical composition of the present invention is envisaged to be useful for treating a variety of diseases, including Wilson Disease, cancer, neurodegenerative diseases, diabetes, bacterial infections, inflammatory diseases, fibrosis, cirrhosis, familiar amyotrophic lateral sclerosis, lead and/or mercury poisoning.

(A) Histopathological comparison (HE staining) of liver damage in diseased LPP$^{-/-}$ rats (upper panel) and untreated WD patients with acute liver failure (lower panel). Tissue necrosis with resorptive inflammation as well as repair (fibrosis) is detectable (black arrowhead), proliferation of bile ducts (circle), anisokaryosis (black arrow), and several inflammatory infiltrations (white arrow) are marked. Insert shows apoptosis (white asterisk) and nodules with ballooned hepatocytes (black asterisk). Scale bar: 100 μm.

(B) Mitochondrial structure impairments in diseased LPP$^{-/-}$ rats (both left panels) and untreated WD livers with acute liver failure (both right panels). Transparent vacuoles of varying sizes (asterisk), cristae dilations (arrow), marked differences in electron densities, and separated inner and outer membranes (arrowhead) can be identified. Scale bar: 500 nm.

(C) Comparable copper burden in whole liver homogenates and in purified liver mitochondria from LPP$^{-/-}$ rats and untreated WD patients with acute liver failure. Control heterozygous LPP$^{+/-}$ (N=17); affected LPP$^{-/-}$ with strongly elevated copper but AST<200 U/L, bilirubin <0.5 mg/dl (N=13); disease onset LPP$^{-/-}$ with AST≥200 U/L, bilirubin <0.5 mg/dl (N=8); diseased LPP$^{-/-}$ with AST≥200 U/L, bilirubin >0.5 mg/dl (N=10). *Significant to control, #significant to affected, †significant to disease onset, *p<0.05, p<0.01, *p<0.001.

Figure 2:
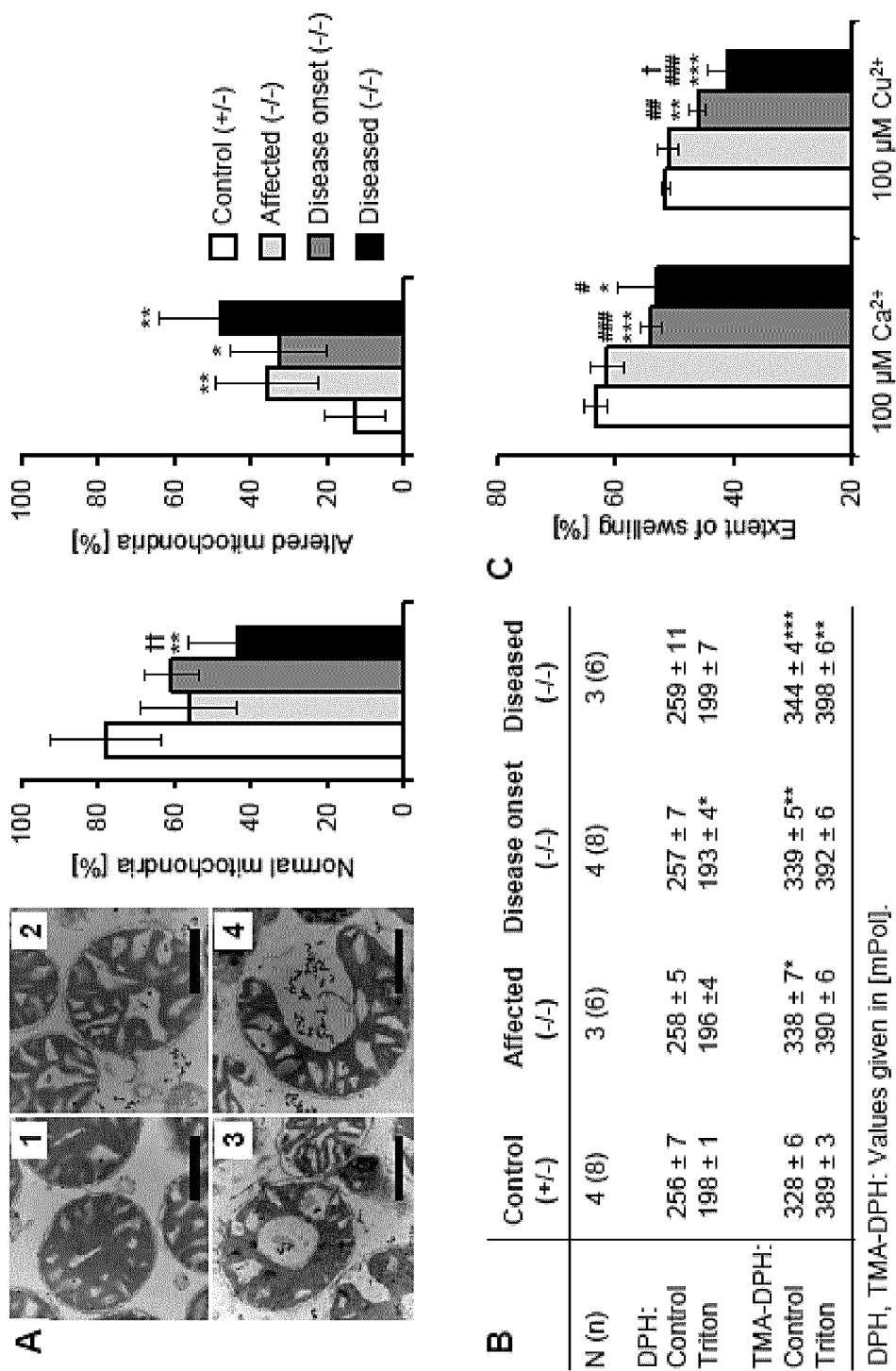
Figure 2:
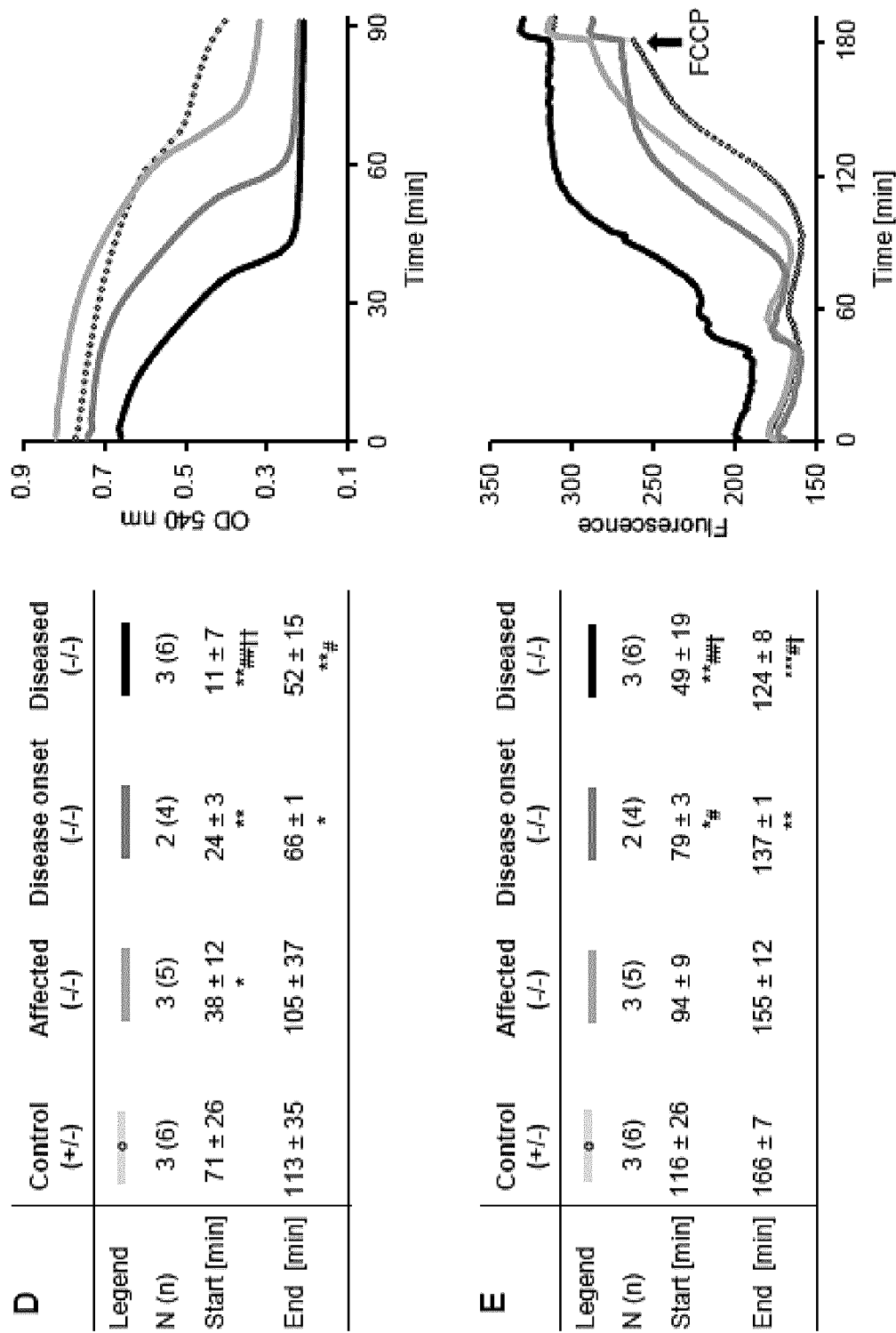

FIG. 2: Increasing copper load severely attacks the mitochondrial membrane integrity.

(A) The progressive disease states in LPP$^{-/-}$ rats are paralleled by a decrease in normally structured mitochondria (type 1 and 2) and an increase in structurally altered mitochondria (type 3 and 4). Scale bar: 500 nm. Control LPP$^{-/-}$ 82-89 d, N=4, n=766; affected LPP-/-82-93 d, N=6, n=886; disease onset LPP$^{-/-}$ 81-93 d, N=4, n=784; diseased LPP$^{-/-}$ 104-107 d, N=5, n=939. N=number of rats, n=number of analyzed mitochondria. *Significant to control, †significant to disease onset, *p<0.05, **p<0.01.

(B) Fluorescence polarization demonstration of physical alterations in mitochondrial membrane properties at the protein-lipid interface (TMA-DPH) but not at the membrane inner lipid phase (DPH) in LPP$^{-/-}$ vs. control mitochondria. N=number of rats, n=number of measurements. *Significant to control, *p<0.05,p<0.01, *p<0.001.

(C) Upon calcium or copper induced MPT isolated LPP$^{+/-}$ mitochondria undergo large amplitude swelling, which is significantly reduced in LPP$^{-/-}$ mitochondria from diseased and disease onset rats. (N=2-3, n=4-6). *Significant to control, #significant to affected, †significant to disease onset, *p<0.05, p<0.01, *p<0.001.

(D) Calcium-induced (100 μM) MPT can be efficiently inhibited by Cys-A (5 μM). This blocking effect is severely impaired in mitochondria from diseased and disease onset LPP$^{-/-}$ rats. Table (left) shows mean values and standard deviations whereas curves (right) depict one exemplary measurement. *Significant to control, #significant to affected, †significant to disease onset, *p<0.05, **p<0.01.

(E) LPP$^{-/-}$ mitochondria lose their membrane potential at earlier time points compared to control mitochondria. Table (left) shows mean values and standard deviations whereas curves (right) depict one exemplary measurement. *Significant to control, #significant to affected, †significant to disease onset, *p<0.05, p<0.01, *p<0.001.

Figure 3:
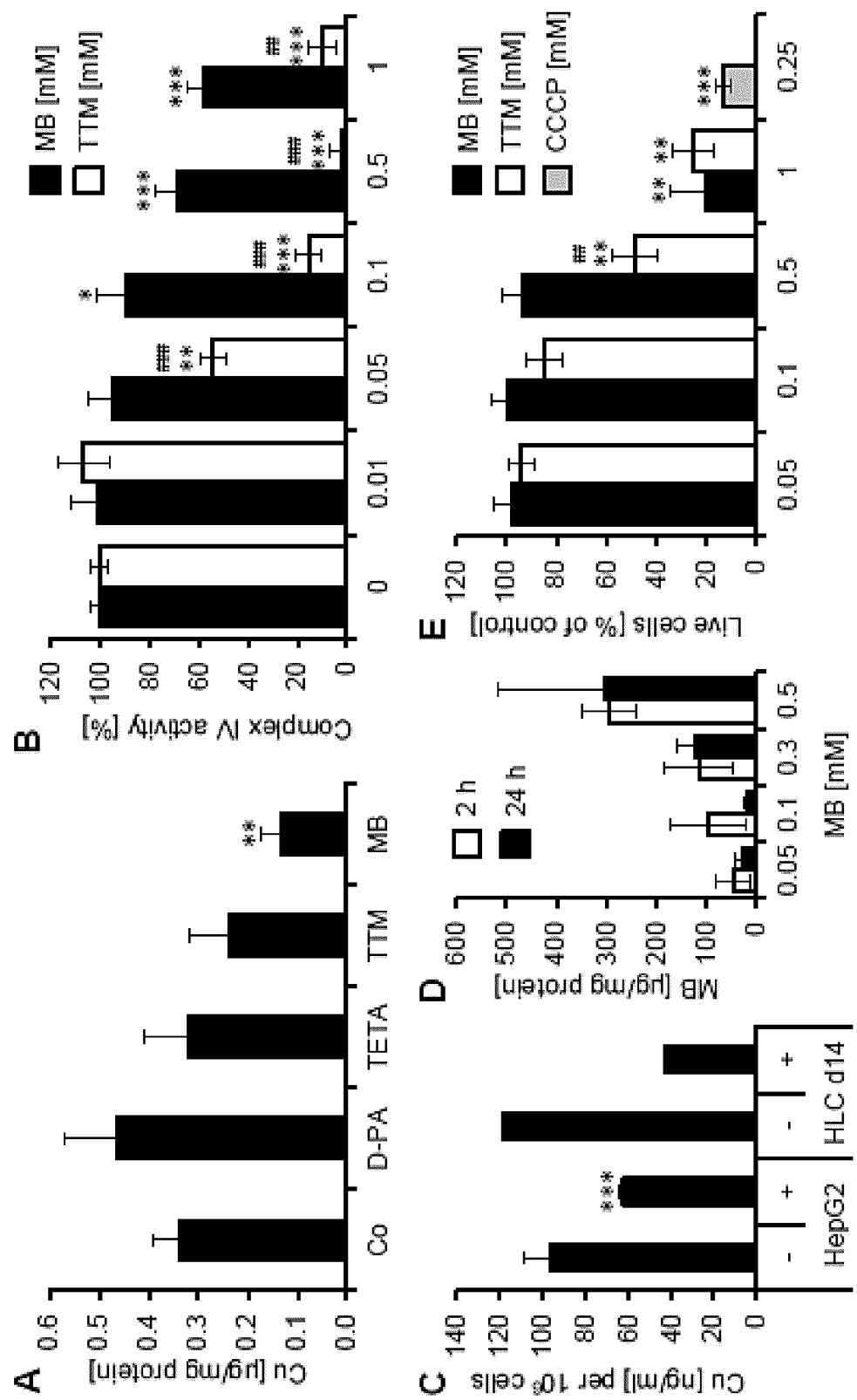
Figure 3:
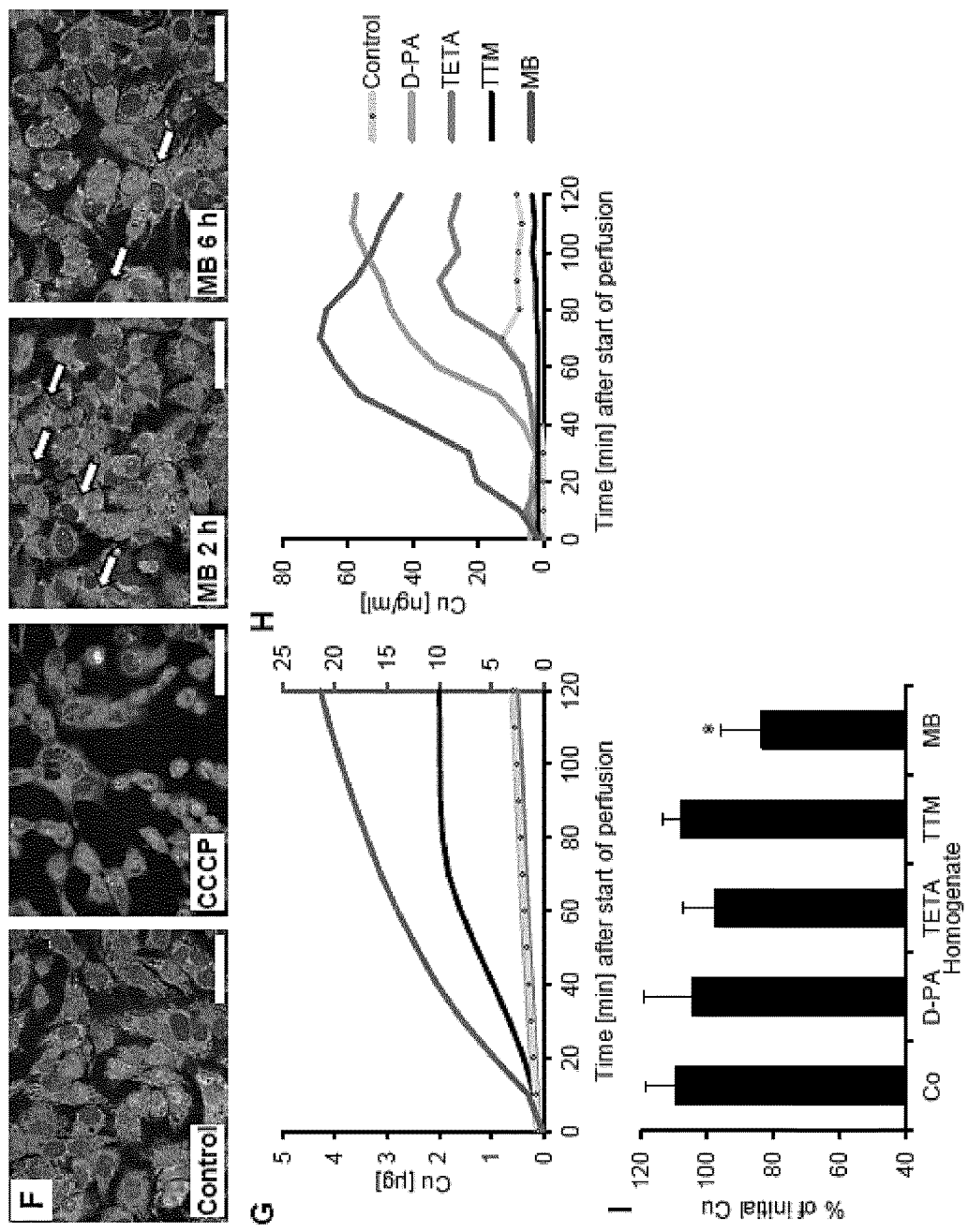

FIG. 3: Methanobactin (MB) driven copper depletion from liver mitochondria, hepatocytes and whole liver.

(A) MB driven copper extraction from freshly isolated copper burdened LPP$^{-/-}$ mitochondria vs. copper extraction by the copper chelators D-PA, TETA, and TTM (2 mM each, 30 min incubation, Co=buffer treated control, N=3). *Significant to control, **p<0.01.

(B) Toxicity of MB to the copper-dependent mitochondrial respiratory complex IV activity, versus toxicity observed with TTM (MB: N=3, n=9; TTM: N=1, n=3) .*Significant to buffer control, #significant to respective concentration of MB, *p<0.05, p<0.01, *p<0.001.

(C) Copper preloaded HepG2 (N=3) and WD patient-derived hepatocyte like (HLC) cells (one out of two independent experiments) are highly efficiently de-coppered by MB ((+) 24 h MB treated, (-) untreated control). Significant to untreated control, ***p<0.001.

(D) Dose-dependent intracellular MB uptake into HepG2 cells (given in μg MB per mg cellular protein) at 2 and 24 hours (N=3).

(E) Cellular (HepG2) toxicity of MB in comparison to TTM(N=3, n=9). The Δψ dissipating protonophor CCCP served as positive control. *Significant to buffer control, #significant to respective concentration of MB, p<0.01, *p<0.001. Arrows indicate cells with low Δψ.

(F) MB (500 μM) treated HepG2 cells show only intermediate phases of mitochondrial membrane potential loss (250 μM CCCP, N=2). Staining indicates nuclei (blue), mitochondria with Δψ (orange-red) and mitochondria without Δψ (green). Scale bar: 50 μm.

(G) Cumulative copper excretion into bile upon a two hour LPP$^{-/-}$ liver perfusion. MB (0.7 μM) forces tenfold higher copper amounts into bile in comparison to TTM (0.8 μM) (please note the different scales for MB (right, blue axis) and D-PA, TETA and TTM (left, black axis)). D-PA (2.2 μM) and TETA (1.8 μM) did not bring copper into bile (N=3, Co=Krebs-Ringer buffer control).

(H) Copper concentration in the perfusate during a two hour LPP$^{-/-}$ liver perfusion. All chelators except TTM transport copper to the perfusate (concentrations as in G, N=2).

(I) Two hour LPP$^{-/-}$ liver perfusion. MB significantly reduces the liver copper content in contrast to D-PA, TETA, TTM and Krebs-Ringer buffer perfused controls (Concentrations of chelators as in G, N=3). *Significant to control, *p<0.05.

Figure 4:
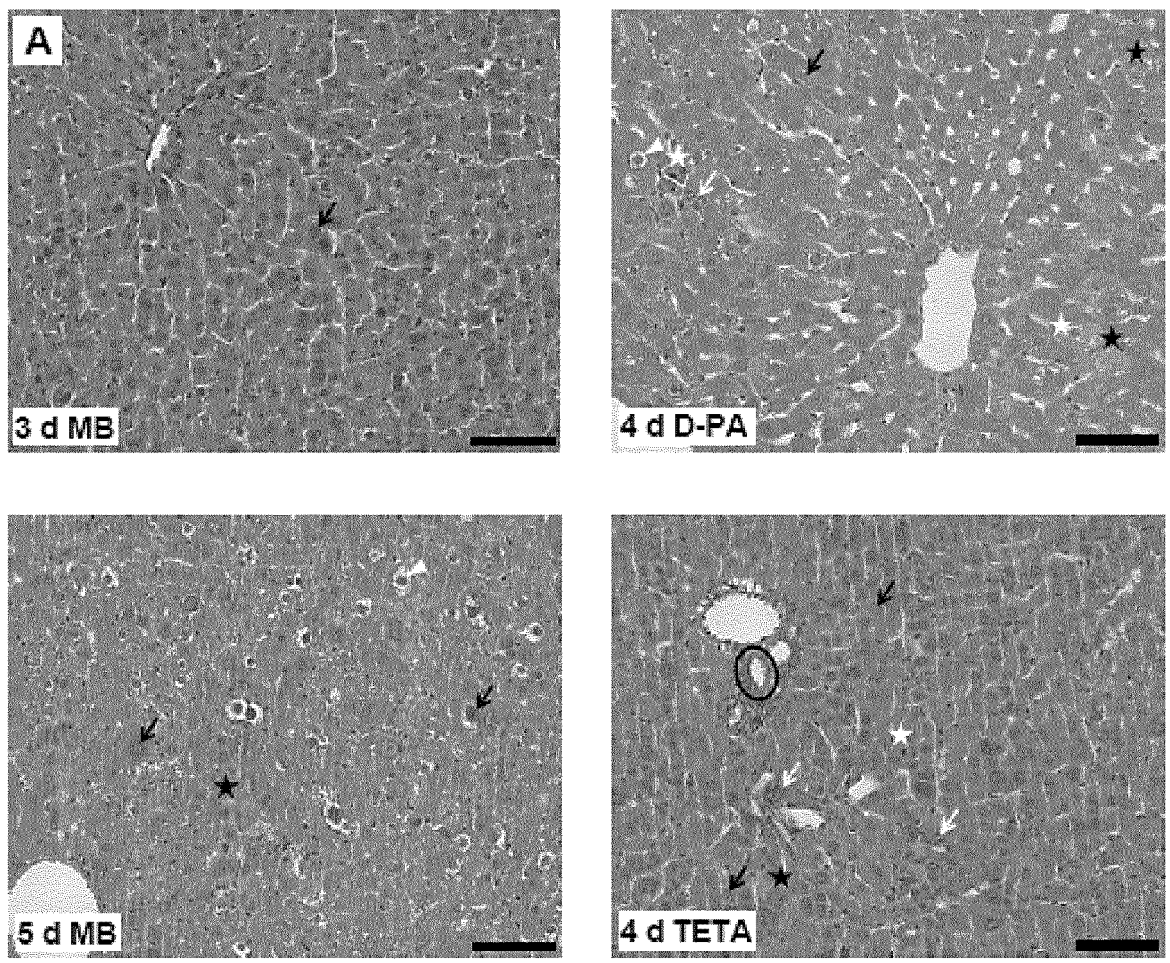
Figure 4:
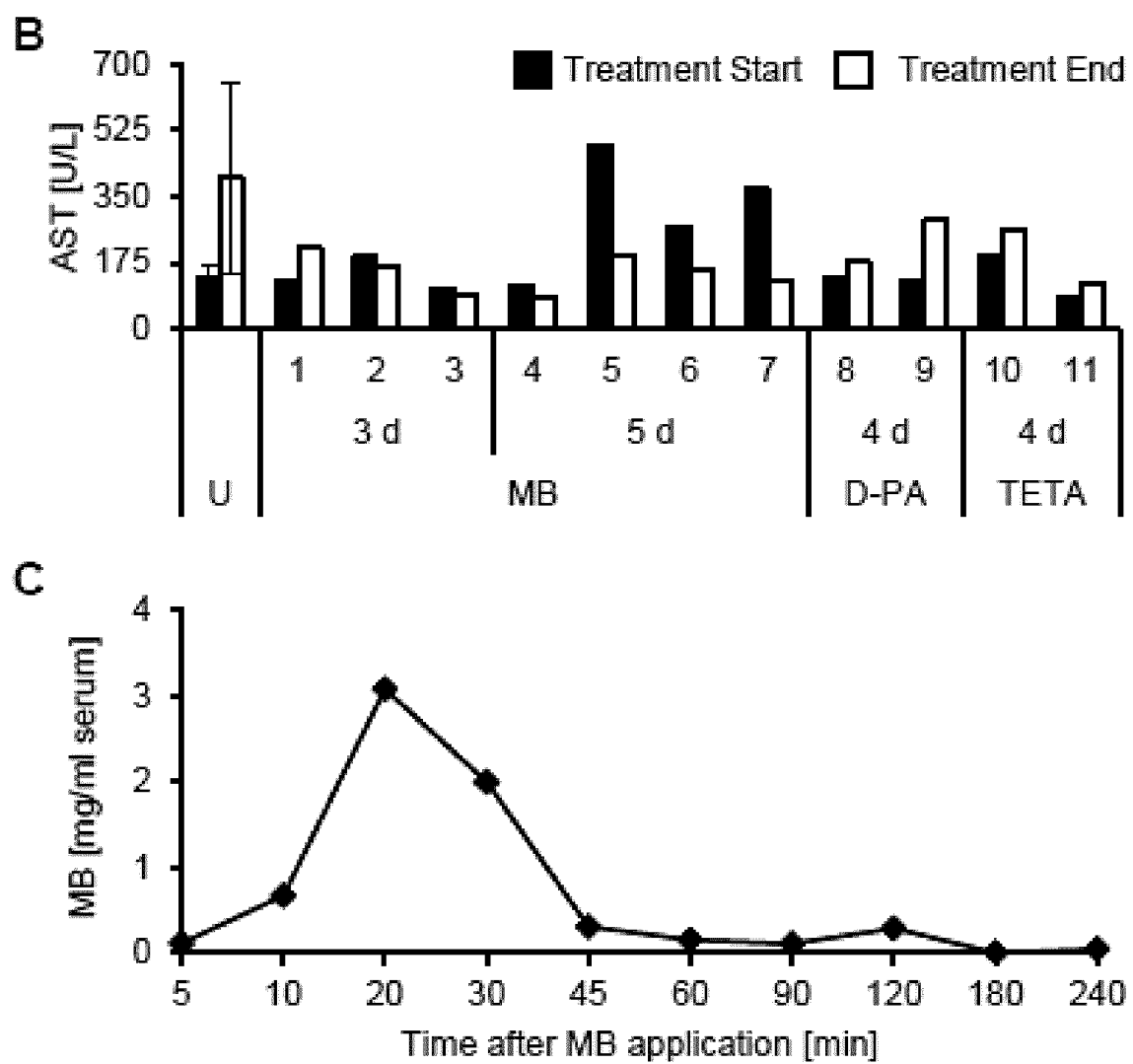

FIG. 4: Acute liver failure is efficiently avoided by a short-term in vivo treatment with methanobactin (MB).

Figure 1:
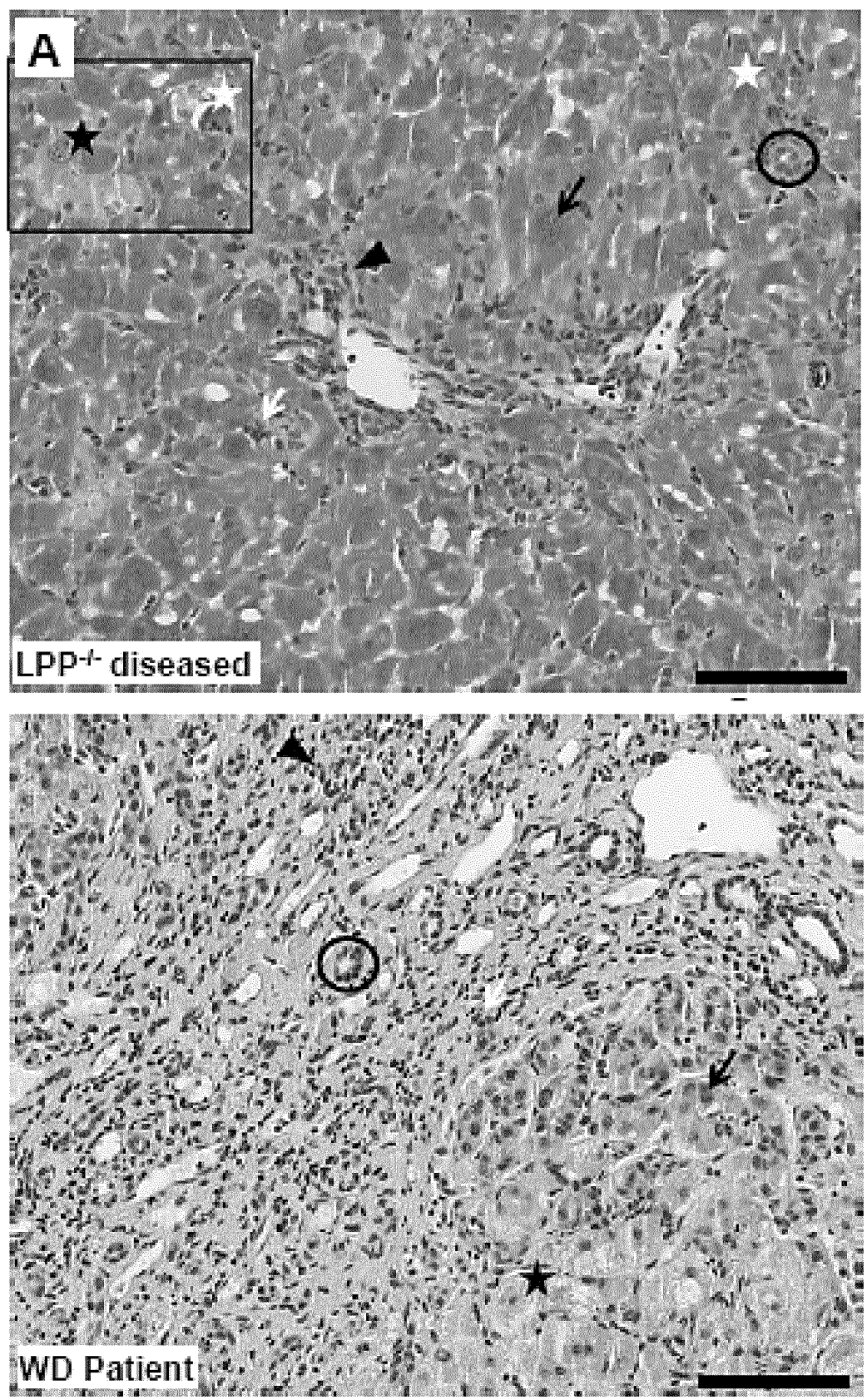
FIG. 1: Liver disease in the LPP rat mirrors acute liver failure in WD patients by a devastating mitochondrial copper overload.
Figure 1:
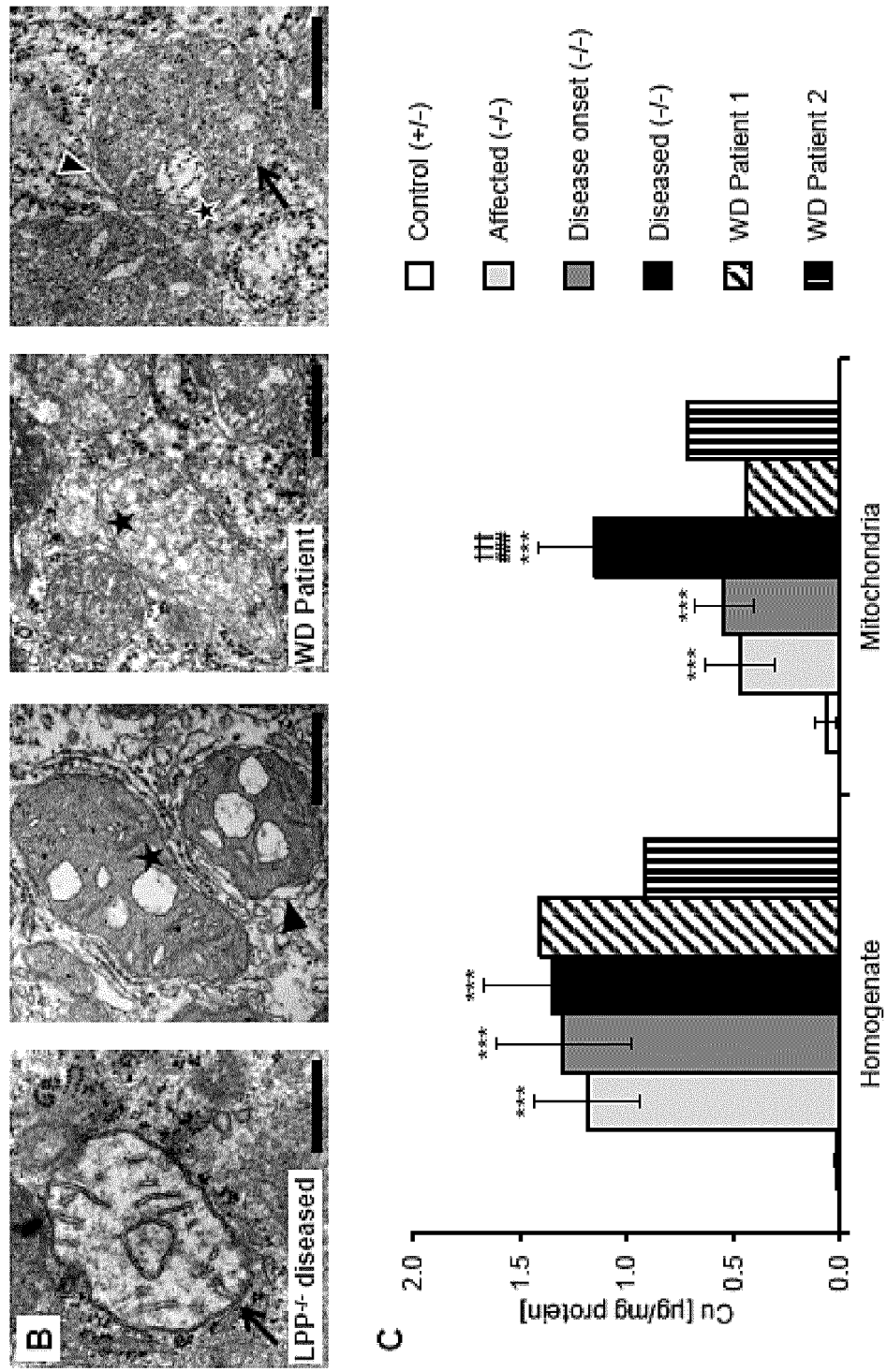
Figure 6:
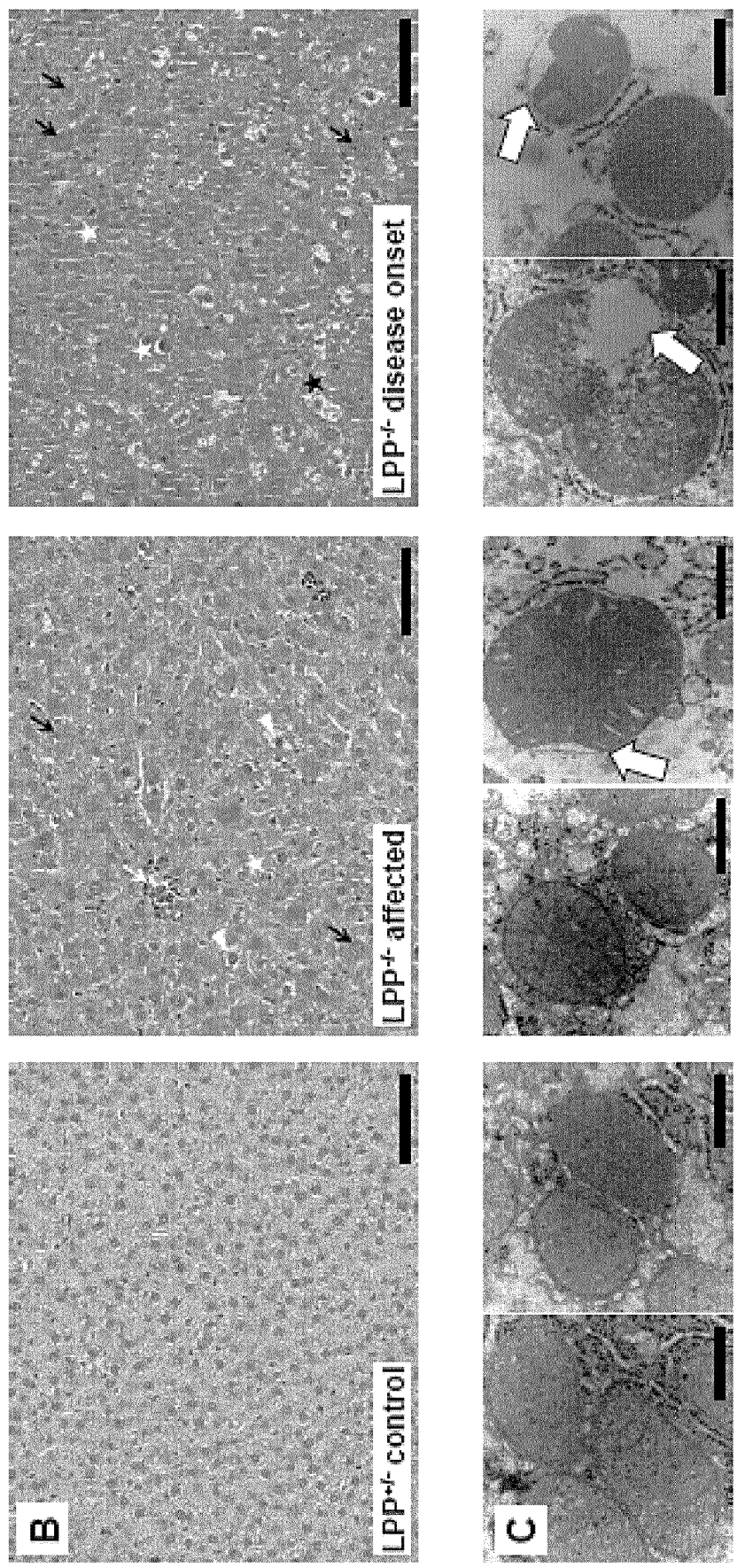
Figure 6:
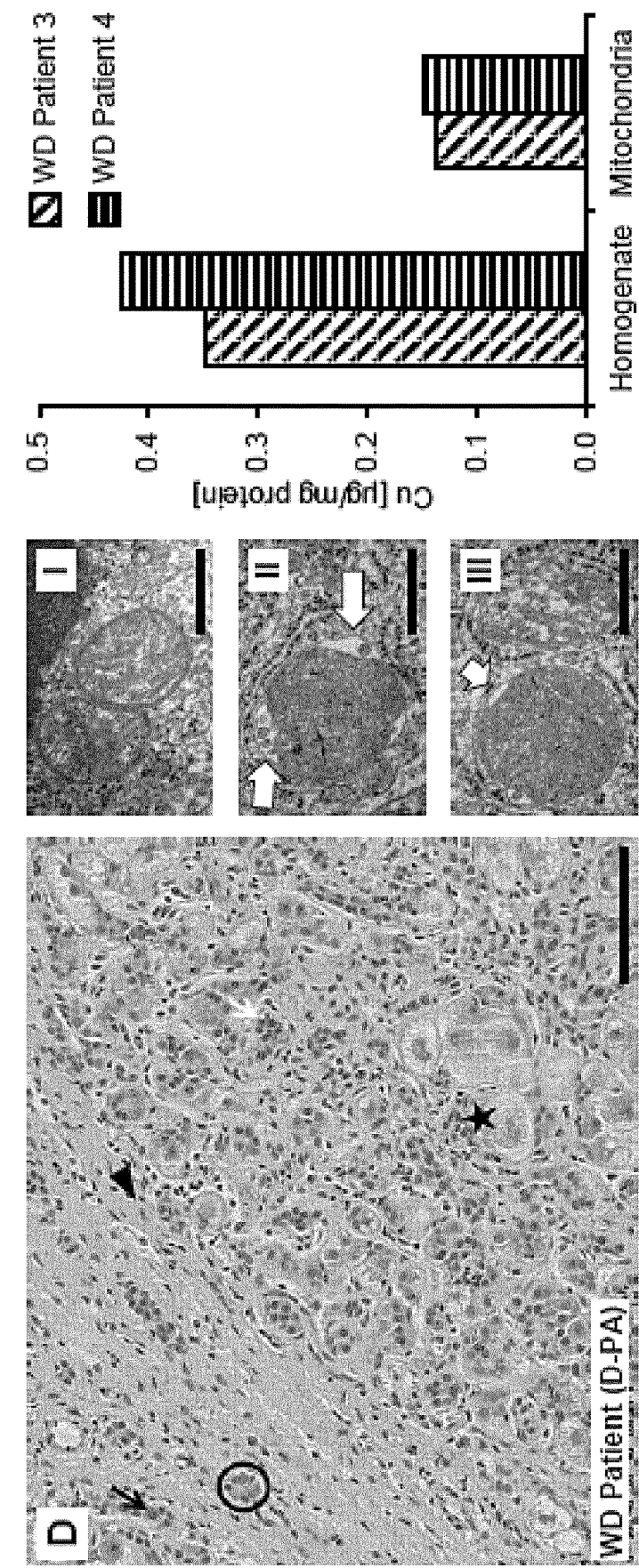

(A) Reductions in histopathological features of overt liver damage were found in LPP$^{-/-}$ livers treated for 3 or 5 days by MB but not upon four days D-PA or TETA treatment (scale bar: 100 μm, HE staining, legend to symbols as in FIGS. 1, 6). Daily doses were 150 mg (130 μmol) MB/kg bw, 100 mg (540 μmol) D-PA/kg bw or 480 mg (2190 μmol) TETA/kg bw.

(B) In contrast to untreated LPP$^{-/-}$ controls (U, N=6) and D-PA (no. 8,9) or TETA (no. 10, 11) treated LPP$^{-/-}$ rats, short-term MB treated LPP$^{-/-}$ animals (no. 1-7) presented with markedly decreased AST levels, returning to normal.

(C) Upon i.p. injection, MB is only detectable in the serum for half an hour, indicating a very short systemic residence time (n=2).

(D) Short-term MB treated LPP$^{-/-}$ rats (N=3, each) presented with a progressive but minor reduction at the whole liver copper level but a significant reduction at the mitochondrial copper level, in contrast to untreated LPP$^{-/-}$ controls (N=4) and D-PA or TETA (N=2, each) treated LPP$^{-/-}$ rats. *Significant to untreated controls, *p<0.05.

(E) In contrast to mitochondria isolated from untreated LPP$^{-/-}$ controls (FIG. 2A) and D-PA or TETA treated LPP$^{-/-}$ rats, massively reduced numbers in mitochondria with severely impaired structure (type 4) were isolated from short-term MB treated LPP$^{-/-}$ rats. (N=2, each, quantification in FIG. 9A, scale bar: 1 μm).

Figure 5:
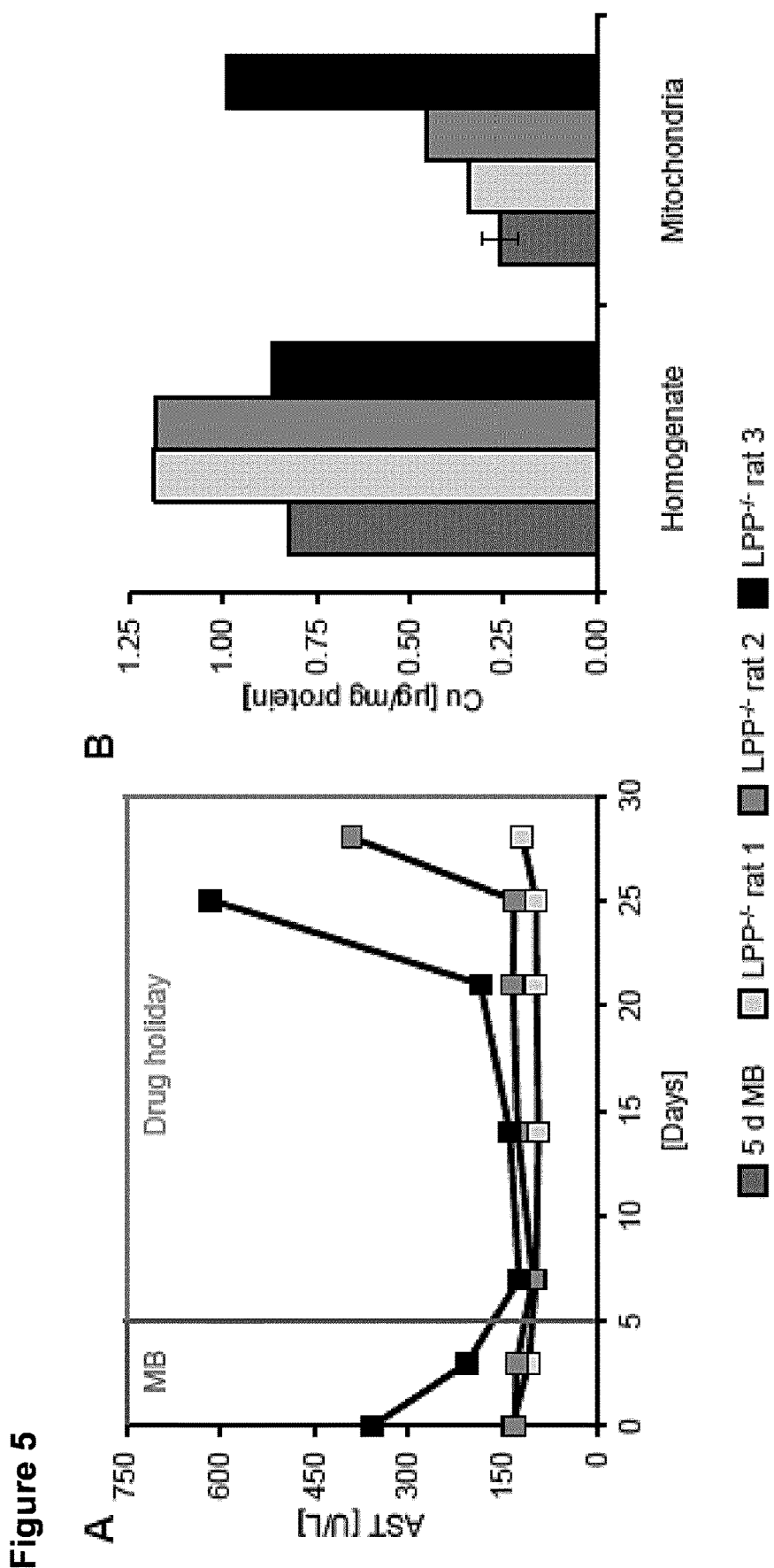
Figure 5:
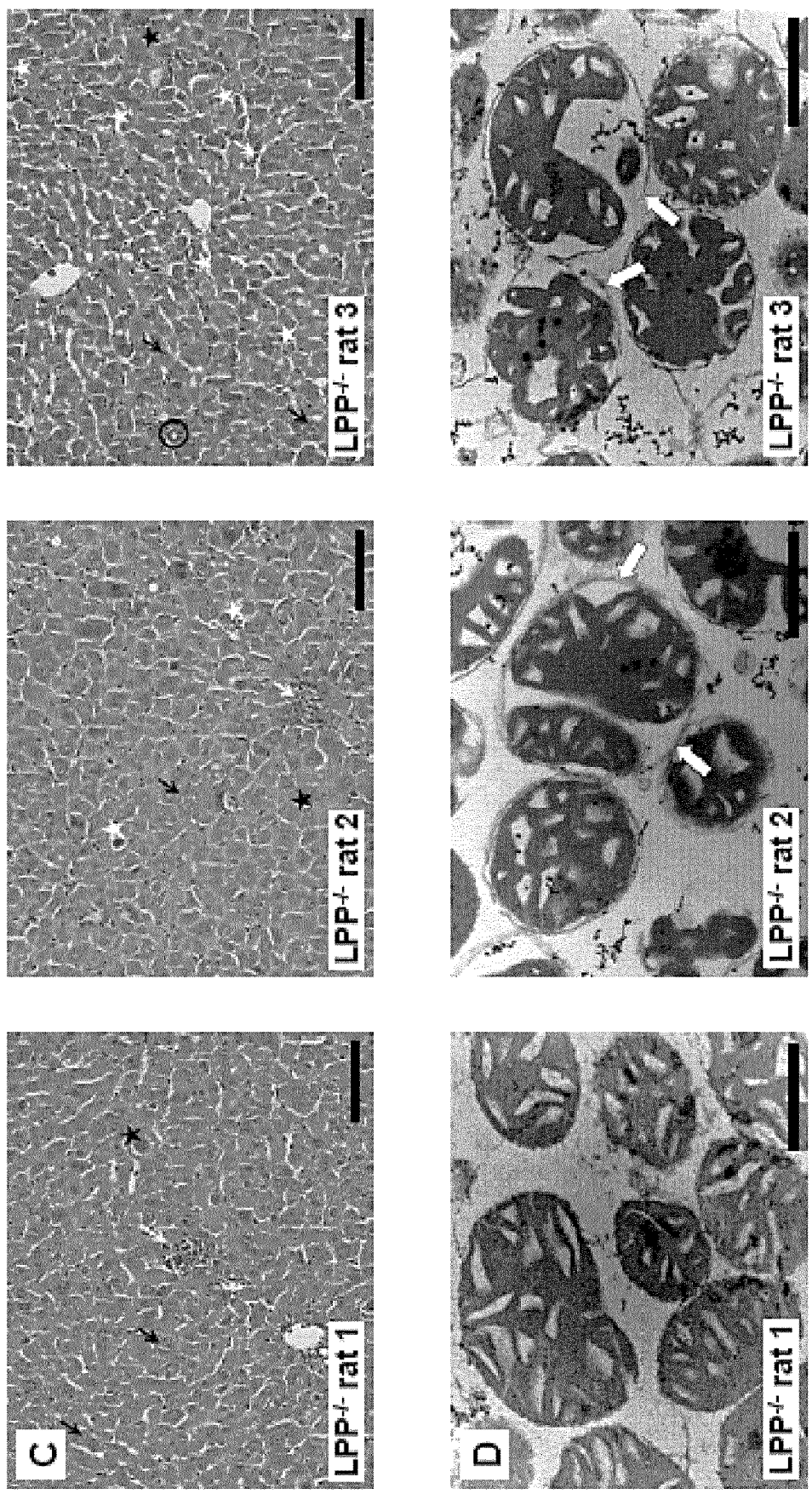

FIG. 5: The protection against acute liver failure by methanobactin lasts several weeks.

(A) Short-term MB treated LPP$^{-/-}$ rats stay healthy for at least two weeks, thereafter serum AST and bilirubin (not shown) levels rise again. At the time of analysis one animal (no 1) is still healthy and two animals (no 2, 3) are diseased.

(B, C, D) In this order (rat 1-3) the mitochondrial copper content increases but not the whole liver copper content (B), the typical histological features of overt liver damage with increased frequency (C), and increased severity of mitochondrial structure impairments (D). Scale bar: 100 μm in (C) and 500 nm in (D).

FIG. 6:

(A) Masson trichrome staining demonstrated signs of fibrosis (stained blue) in diseased LPP$^{-/-}$ rat liver (left panel) but marked fibrosis in explanted WD patient liver (right panel). Scale bar: 100 μm.

(B) Histopathological analysis (HE staining) of LPP rat livers at different disease states shows increasing alterations during progression of the disease (Scale bar: 100 μm; white asterisk: (different stages of) apoptosis, black arrow: anisokaryosis, black asterisk: ballooned hepatocytes, white arrow: inflammatory infiltrates; white arrowhead: cytoplasmic condensation).

(C) Electron micrographs of LPP rat liver mitochondria in situ corresponding to the disease states as in B (Scale bar: 500 nm). Separated inner and outer membranes are indicated by arrows.

(D) Liver damage in explanted livers of WD patients with D-PA treatment failure. Left panel: HE stain reveals histopathological features of liver damage and massive fibrosis (black arrowhead, Scale bar: 100 μm). Middle panels: Some areas presented with relatively intact mitochondria (I), others demonstrated severe structural impairments (II, III, cf. FIG. 1B, Scale bar: 500 nm). Right panel: In comparison to untreated WD patients with acute liver failure (cf. FIG. 10), lower total copper contents were determined in tissue homogenates and in isolated mitochondria from livers of WD patients with D-PA treatment failure.

FIG. 7:

(A) Copper loading of isolated control mitochondria (LPP$^{+/-}$). Mitochondria (4 mg/ml) were pre-incubated with DTT (1 mM), challenged with concentrated (20 mM) or diluted (2 mM) copper stock solutions, subsequently re-purified by density gradient centrifugation, and their copper load determined (N=4).

(B) Copper pre-loaded LPP$^{+/-}$ mitochondria from (A) were incubated with copper chelators (2 mM) for 30 min and subsequently re-purified by density gradient centrifugation. (N=5, *significant to control, *p<0.05, **p<0.01).

(C) Comparison of the effect of MB to LPP$^{+/-}$ control mitochondria vs. LPP$^{-/-}$ mitochondria on copper-dependent mitochondrial respiratory complex IV activity (LPP$^{+/-}$: N=3, n=9, LPP$^{-/-}$: N=2, n=6, *significant to buffer control, #significant to respective concentration of LPP$^{+/-}$, *p<0.05, p<0.01, *p<0.001).

(D) MB treatment causes a 50% reduction of copper in HepG2 cells with basic copper load (N=3, (+) 24 h MB treated, (−) untreated control, *significant to untreated control *p<0.05), (E) Dose dependent toxicity (neutral red) of histidine bound copper on HepG2 cells (N=5; *significant to control, *p<0.05)

FIG. 8:

(A) Bile flow during two hour LPP$^{-/-}$ liver perfusion. Displayed are mean values of three independent experiments.

(B) Cumulative biliary copper excretion during two hour LPP$^{-/-}$ liver perfusion by MB (N=3).

(C) Parallel LDH and copper release into the perfusate during two hour LPP$^{-/-}$ liver perfusion.

FIG. 9:

(A) Quantification to FIG. 4E. In contrast to mitochondria isolated from untreated and D-PA or TETA treated LPP$^{-/-}$ animals, massively reduced numbers in mitochondria with severely impaired structure (type 4) were isolated from short-term MB treated LPP$^{-/-}$ animals (N=number of rats, n=number of mitochondria; Affected (A): N=6, n=886; Disease onset (Do): N=4, n=784; 3 d MB: N=2, n=324; 5 d MB: N=2, n=527; D-PA: N=2, n=252; TETA: N=2, n=366).

(B) Respiratory analysis of mitochondria from the MB treated LPP$^{-/-}$ rats in FIG. 5 after MB drug holiday. At the time of analysis mitochondria from the still healthy animal (no. 1) are as intact as control mitochondria (respiratory control ratio with succinate as substrate, RCR$_S$), whereas mitochondria from the two diseased animals (no. 2, 3) are impaired.

(C) Stability analysis of metal free MB and Zn-loaded MB followed by absorbance measurements of their two metastable oxazolone rings (OxaA/ZnA at 394 nm and OxaB/ZnB at 340 nm)$^{57}$ at 37° C. In contrast to metal free methanobactin, Zn-MB is time stable at 37° C.

(D) Histopathological analysis of untreated (left) and MB treated (right) moribund LPP$^{-/-}$ rats. Liver damage was present in both tissues, however less severe in the MB treated animal indicating liver regeneration (Scale bar: 100 μm, HE staining, symbols as in FIGS. 1, 6).

(E) Mitochondria from the animals described in D, either isolated (left) or in situ (right). In contrast to the untreated animal, only minor structural alterations were observed in the MB treated LPP$^{-/-}$ rat (Scale bar: 500 nm).

(F) Progressively impaired ATP production of mitochondria isolated from LPP$^{-/-}$ rats at different disease states. Short term MB treatments reverse this impairment.

FIG. 10:

Different application routes or treatment regimens can further enhance MB induced mitochondrial de-coppering.

Short term treatments of one week by either 5× MB i.p, 5× MB i.v., and especially by 16×MB i.p. (one week, twice daily) drastically reduce the mitochondrial copper load.

FIG. 11:

Chemical structures of full-length mbs from *M. trichosporium* OB3b (A) (144, 155), *Methylocystis* strain sp.M (B) (136), *M. hirsuta* CSC1 (C) (136), *M. rosea* (D) (136) and *Methylocystis* strain sp. SB2 (E) (135).

FIG. 12: Mb precursor peptides.

Sequences detected in bacteria of known genome sequence from methanotrophs with structurally characterized mbs are shown in red, sequences detected in bacteria of known genome sequence from methanotrophs are shown in blue and sequences detected in bacteria of known genome sequence from non-methanotrophs are shown in green. Bar above amino acids represent the amino acid pair that is or proposed to be post-translationally modified into an oxazolone, imidazolone or pyrazinedione group. Abbreviations: methanobactin from *Methylosinus trichosporium* OB3b (mb-OB3b), *Methylosinus* sp. strains LW3 (mb-LW3), LW4 (mb-LW4), PW1 (mb-PW1), *Methylocystis parvus* OBBP (mb-OBBP), *Methylocystis rosea* (mb-*rosea*), *Methylocystis* strains SB2 (mb-SB2), SC2 (mb-SC2), and LW5 (mb-LW5), *Cupriavidus basiliensis* B-8 (mb-B-8), *Pseudomonas extremaustralis* 14-3 (mb-14-3), *Azospirillum* sp. stain B510 (mb-B510), *Tistrella mobilis* KA081020-065 (mb-*mobilis*) and *Comamonas composti* DSM 21721 (mb-21721).

FIG. 13: Mb gene clusters.

Gene clusters of complete genomes of methanotrophs *M. trichosporium* OB3b, *Methylocystis* sp. SB2 and *Methylocystis rosea*.

FIG. 14: Repetetive treatment regimen with recurrent de-coppering phases.

LPP−/− rats were subjected to the first treatment cycle consisting of three daily MB injections (i.p.) for five days followed by a period of non-treatment. Recurrent treatment cycles resulted in marked reduction in mitochondrial and liver copper load and doubling of time before disease onset as compared to untreated animals.

Figure 15:
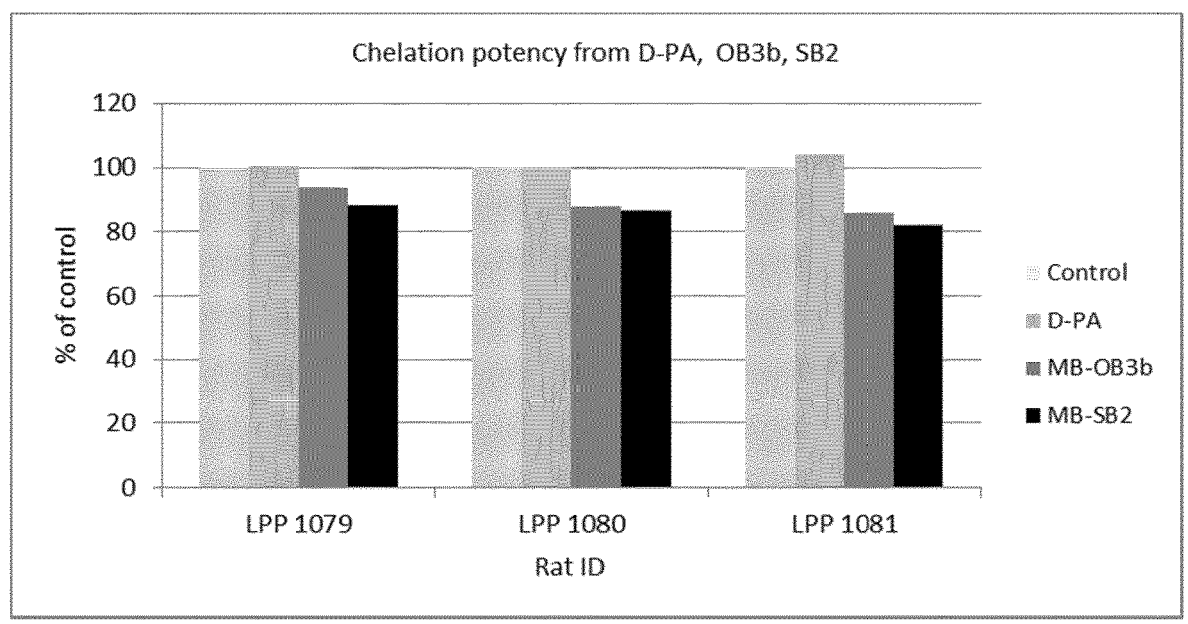

FIG. 15: A structurally and chemically different methanobactin (MB) peptide such as mb-SB2 from *Methylocystis* strains SB2 exhibits similar therapeutic potential in depleting copper from hepatocyte mitochondria.

MB-SB2 from *Methylocystis* strains SB2 acts as a promising cooper chelator compared to existing clinically approved cooper chelators such as D-PA on freshly isolated mitochondria from three different LPP$^{-/-}$ rats (1 mM of D-PA, Ob3b, SB2, 30 min incubation, Control=buffer treated control, N=3). MB peptide mb-SB2 from *Methylocystis* strains SB2 is structurally and chemically deviating from other MB peptides (f.e. from mb-OB3b derived from *Methylosinus trichosporium* OB3b).

DETAILED DESCRIPTION

Wilson Disease (WD), an autosomal recessively inherited copper overload disorder, is a yet incurable disease that is fatal when left untreated. The overall therapeutic approach is the restoration and maintenance of normal copper homeostasis, either by medical therapy or by liver transplantation. Copper chelators (such as D-penicillamine, trientine and tetrathiomolybdate) and/or zinc salts presently represent the gold standard of WD treatment. Regardless of the specific approach chosen, treatment must be continued throughout the patient's lifetime, because abnormal copper accumulation cannot be controlled by a low copper diet. Importantly, non-adherence or discontinuation of medical therapy is associated with the risk of intractable hepatic or neurologic deterioration.

Presently available treatment options are, unfortunately, only of limited efficacy in terms of reducing copper levels; and are moreover incapable of restoring physiological copper excretion via the bile. Along with severe side effects, the need for high dosages and repeated administration (often several times a day), results in a severe impairment of quality of life and overall poor patient compliance.

Moreover, commonly prescribed WD therapeutics fail to restore liver function once WD manifests as advanced liver failure—e.g., due to delayed diagnosis, poor compliance, or rapid, fulminant hepatitis. In this case, liver transplantation with all its inherent risks and detriments presently remains the only viable option. Although liver transplantation is effective to restore normal biliary copper excretion (thereby preventing disease recurrence) and promotes removal of copper from extrahepatic sites, given the chronic shortage of suitable donor organs and the substantial morbidity and mortality associated with the procedure, it is considered as a treatment option only in life-threatening circumstances.

Novel means and methods for WD treatment are thus urgently needed. The surprising findings underlying the present invention show that methanobactins, methanotroph-derived chalkophores, are surprisingly potent and well-tolerated de-coppering agents. Unexpectedly, the present inventors found that due to their superior copper binding affinity, methanobactins (in contrast to other copper chelators, being far less efficient) can advantageously be used for massive depletion of (excess) copper with a long-term effect—thereby allowing for a novel treatment regimen that is expected to markedly improve patient compliance and, consequently, overall therapeutic success. Moreover, the present inventors found that methanobactins are even capable of removing accumulated mitochondrial copper—which has recently been suggested as a crucial causative factor for oxidative stress underlying tissue and organ damage in a number of diseases. Therefore, methanobactins are not only promising agents for treatment of WD, but also for a number of unrelated diseases that have been linked to increased copper levels in the blood, in whole cells and/or in mitochondria within.

Wilson Disease

Wilson Disease (WD) is an inherited disorder associated with mutations in the copper transporting ATPase ATP7B, resulting in impaired, non-functional or impaired ATP7B protein activity. More than 500 mutations in ATP7B have been identified, most of which are low-abundance mutations.

WD is typically characterized by severe impairment (or even complete absence) of biliary copper excretion, resulting in hepatic copper overload and, eventually, copper spillover into the circulation and/or central nervous system.

A variety of signs and symptoms reflecting cellular injury from excess copper may be present in affected patients. Many types of liver disease may be encountered in patients with Wilson Disease, and presenting symptoms of liver disease can be highly variable, ranging from asymptomatic, with only biochemical abnormalities, to overt cirrhosis. Wilson Disease may also present as acute liver failure as described elsewhere herein. Other manifestations include Coombs positive hemolytic anemia, cardiomyopathy, and endocrine dysfunction. Neurologic signs, more common in the second or third decade of life, are variable, and most often include tremor, ataxia, and dystonia, consistent with neuropathologic findings of basal ganglia involvement. The most common psychiatric features are abnormal behaviour (typically increased irritability or disinhibition), personality changes, anxiety, and depression.

Diagnosis of WD typically requires a combination of tests that are reflected by the diagnostic score that was proposed by the Working Party at the $8^{th}$ International Meeting on WD, Leipzig 2001 (Ferenci et al. Liver Int. 2003; 23(3): 139-42) and is now included in the European Association for the Study of the Liver (EASL) clinical practice guidelines for Wilson Disease (EASL Clinical Practice Guidelines: Wilson's disease, J Hepatol. 2012 March; 56(3):671-85). Often, the combination of Kayser-Fleischer rings and a low serum ceruloplasmin decreased by 50% of the lower normal value, typically 0.1 g/L or less, is sufficient to establish a diagnosis. Kayser-Fleischer rings are caused by deposition of copper in Desçemet's membrane of the cornea and can be assessed by slit lamp examination. ATP7B loss-of-function and consequent failure to incorporate copper during ceruloplasmin biosynthesis results in the secretion of an apoprotein that is devoid of enzymatic activity and rapidly degraded, accounting for low serum concentrations of enzymatically active ceruloplasmin and thus proportionally low total serum concentrations of copper typically seen in WD patients, except in cases of severe liver injury or acute liver failure, when there are high serum concentrations of non-ceruloplasmin-bound copper due to its sudden release from the liver.

Other important diagnostic parameters according to the EASL Clinical Practice Guidelines (loc. cit.) include increased urinary copper excretion (>1.6 µmol/24 h or >0.64 µmol/24 h in children), non-ceruloplasmin-bound copper ("free copper") levels >1.6 µmol/L and a hepatic parenchymal copper content of >4 µmol/g dry weight. Direct genetic testing for ATP7B mutations are also increasingly available to confirm clinical WD diagnosis.

Notably, methanobactin treatment according to the present invention is in general envisaged for WD manifesting by any of the aforementioned signs and symptoms. Due to their superior copper binding affinity, methanobactins are considered useful in any form of WD. Unless noted otherwise, the term "Wilson Disease" or "WD" thus includes acute and non-acute forms of WD, presenting with hepatic and/or neurological deficits, early onset WD in infancy and late-onset WD in adults, previously treated and untreated WD. Advantageously, methanobactins, particularly administered according to the treatment regimen provided herein, are also considered to be effective when otherwise liver transplantation would be indicated, including WD patients with acute liver failure as the first presentation of disease, non-responders to conventional copper chelator therapy, those who present with end-stage liver disease (ESLD) and severe hepatic insufficiency, and patients with neurological WD in the absence of liver failure as reviewed by Schilsky M L, Ann N Y Acad Sci. 2014 May; 1315:45-9. Also encompassed by the term are related copper-overload diseases in non-human mammalian subjects, including dogs. The term WD also includes animal models of WD, such LPP−/− rats carrying an ATP7B mutation that completely abolishes its hepatic copper transport activity.

In general, patients presenting with any of the manifestations mentioned in the foregoing are envisaged to benefit from methanobactin therapy. Particularly, (recurring) treatment cycles of massive copper depletion as a result of methanobactin administration according to the treatment regimen described herein are envisaged as an effective, well-tolerated and patient-compliant treatment option for WD presenting with any of the aforementioned signs and symptoms.

Treatment Regimen

Accordingly, in a first aspect, the present invention provides a copper-binding methanobactin for use in a method of treatment of Wilson Disease in a subject, wherein treatment comprises at least one treatment cycle of (a) a first phase of methanobactin administration followed by (b) a second phase of non-treatment, wherein the second phase exceeds the first phase. "Non-treatment" refers to a period of time during which no methanobactin is administered. Optionally and advantageously, "non-treatment" may include that no other WD therapeutics (in particular copper chelators) are administered. Surprisingly, it turned out that methanobactins as described herein are extremely efficient and well-tolerated de-coppering agents that allow for (recurrent) treatment phases of massive copper depletion with a long-term effect. I.e., the present inventors discovered that steady administration (as with copper chelators known in the art) is not necessarily required when using methanobactins for WD treatment, but that patients can rather undergo (recurrent) phases of methanobactin treatment for removing excess copper, followed by phases that preferably do not require administration of WD therapeutics at all. This is a significant advantage over currently known WD therapeutics which often require life-long, steady administration in high dosages. The treatment regimen according to the present invention is therefore expected to markedly improve quality of life of WD patients, and, thereby, patient compliance and overall therapeutic success.

Particularly, the first phase of the inventive treatment regimen is envisaged to last for a period of 1, 2, 3, 4, 5, 6, 7, 8, 9, 10 or more consecutive days. During the first phase of treatment ("de-coppering phase"), the methanobactin may be administered as described elsewhere herein either in single doses once daily, twice daily, three times daily, four times daily, five times daily, every other day, or continuously. The first phase of administration of the methanobactin is followed by a second phase of non-treatment. Advantageously, said second phase is even thought to exceed the first phase of methanobactin administration as demonstrated in the appended examples, and is hence envisaged to last for at least 1, 2, 3, 4 or 5 weeks or even longer. As will be readily acknowledged by the skilled practitioner, the duration of the second phase will depend on several factors, e.g. nutritional copper intake, body constitution, severity of WD, etc. Nevertheless, a minimum period of non-treatment of at least 1 week is envisaged herein after the first phase of methanobactin administration.

It will be readily understood that recurrent treatment cycles are envisaged, i.e. several treatment cycles as described in the foregoing may follow one another. Specifically, a phase of non-treatment may be followed by a phase of treatment (de-coppering phase), and a subsequent phase of non-treatment may be followed by another de-coppering phase, and so on. Treatment cycles may be reiterated in intervals, over several weeks, months, years, or even life-long. The treatment regimen of the present invention provides for prophylactic depletion of copper on a regular basis (i.e. before signs and symptoms of WD occur) and/or for acute and optionally recurrent de-coppering treatment whenever necessary. The skilled practitioner will readily be able to assess when methanobactin treatment according to the invention is indicated.

Acute WD

As explained previously, the present invention provides a novel and effective treatment regimen that allows for (optionally repeated) copper depletion in WD patients. Another surprising insight underlying the present invention is the fact that methanobactins are effective for treatment of acute WD presenting as acute liver failure (ALF); a condition that was, to date, invariably fatal unless liver transplantation was conducted.

Acute WD is defined herein as WD manifesting as acute liver failure (ALF), which may be the initial presentation of WD or can occur when WD treatment is stopped. Known copper chelators presently used for WD therapy are, by far, not able to bind to and remove enough excess copper to remedy the rapid deterioration of liver function seen in WD patients presenting with ALF. In contrast, methanobactins as described herein have surprisingly been found to be capable of depleting copper so efficiently that even WD patients presenting with acute WD—manifesting as ALF—are envisaged to be effectively treatable without the need of emergency liver transplantation.

Acute liver failure is defined as the rapid development of hepatocellular dysfunction (i.e. within less than 26 weeks from the onset of the first hepatic symptoms), optionally accompanied by coagulopathy and hepatic encephalopathy in a patient. Hepatic encephalopathy may present as deficits in higher brain function (e.g. mood, concentration in grade I) to deep coma (grade IV). Coagulopathy typically manifests as a prolongation in prothrombin time (usually an International Normalized Ratio (INR) 1.5), and progressive thrombocytopenia (detectable in a full blood count).

Diagnosis of ALF is based on physical exam, laboratory findings and patient history. On laboratory testing, liver function can be assessed by evaluating aspartate transaminase (AST), alanine transaminase (ALT), alkaline phosphatase (ALP), gamma glutamyl transpeptidase (GGT), total bilirubin and/or albumin levels. Subjects with ALF due to WD often present with a nonimmune (Coombs-negative) hemolytic anemia that may precede the development of liver failure or occur concurrently with the liver injury. Decay of liver cells may result in the release of large amounts of stored copper into the circulation, thereby increasing "free" (non-ceruloplasmin bound) copper levels. An increase in the alkaline phosphatase (ALP) to bilirubin ratio of less than 4:1 owing to the relative decrease in alkaline phosphatase (ALP) and increased bilirubin (resulting from hemolysis and hepatic dysfunction), a ratio of aspartate transaminase (AST) to alanine transaminase (ALT) of greater than 2.2:1, and increases in serum copper, typically above 200 µg/dL, are suggestive of ALF due to acute WD. Guidance as to how to identify such patients is i.a. provided by Schilsky M L, Ann NY Acad Sci. 2014 May; 1315:45-9 and Bermann et al. Gastroenterology. 1991 April; 100(4):1129-34. Particularly, if both the alkaline phosphatase (ALP) to bilirubin ratio is greater than 4:1 and the AST to ALT ratio is above 2.2 concurrently, ALF due to WD can be assumed.

Diagnosis can be confirmed by evaluating other signs and symptoms suggesting Wilson Disease, including clinical symptoms (e.g. deep jaundice) and the conventional WD diagnostic parameters (ceruloplasmin, serum or urinary copper as described elsewhere herein). The diagnosis has to be ascertained by determining the hepatic copper content by liver biopsy and/or mutation analysis as described previously.

The clinical presentation of acute WD typically progresses rapidly from hepatic to renal failure and, when untreated, leads to almost 95% mortality unless emergency liver transplantation is available. The present inventors were the first to acknowledge that methanobactins can be used as an effective remedy of the severe clinical manifestations of acute WD. It is contemplated that copper depletion by administration of methanobactins may even render liver transplantation in acute WD patients obsolete. Methanobactin treatment of acute WD can be carried out according to the treatment regimen described elsewhere herein, or according to any other treatment scheme that the skilled practitioner considers appropriate. Typically, acute WD treatment will involve a phase of massive copper depletion by administration of a sufficient amount of methanobactin, that may be ended once the signs and symptoms of acute WD subside; and/or laboratory values improve. Subsequently, treatment according to the regimen of the present invention may follow.

Methanobactin

As set out elsewhere herein, the present inventors were the first to acknowledge the therapeutic potential of methanobactins as safe and effective copper depleting agents for WD treatment according to a novel treatment regimen, and for treatment of acute WD that was to date considered to be irreversible by drug therapy. The term "methanobactin" or "mb" as used herein generally refers to a copper-binding (and Cu(II)-reducing) peptide derived from bacteria, particularly methanotroph bacteria. Unless denoted otherwise, "copper" is used herein to refer to both Cu(I) and Cu(II). Naturally occurring methanobactins are thought to be secreted to the extracellular media where they function as chalkophores by binding to Cu(II) or Cu(I) and shuttling the copper into the cell.

The term "methanobactin" as used herein in particular encompasses modified peptides characterized by the presence of one oxazolone ring and a second oxazolone, imidazolone or pyrazinedione ring. The two rings are separated by 2-5 amino acid residues. Each ring has an adjacent thioamide group. Structurally, mbs can be divided into two groups that are both envisaged for the uses according to the present invention (FIGS. 11, 12). One type (Group I) is represented by mb from *Methylosinus trichosporium* OB3b. Based on sequence similarity and alignments, the putative mbs from *Methylosinus* sp. strain LW3 (mb-LW3), *Methylosinus* sp. strain LW4 (mb-LW4), *Methylosinus* sp. strain PW1 (mb-PW1), *Methylocystis* strain LW5 (mb-LW5) and one of the two mbs from *Methylocystis parvus* OBBP (mb-OBBP(2)) would also fall within this group (FIG. 12). In this group the rings are separated by 4 or 5 amino acids and the mb contains 2 or more Cys not involved in ring formation.

The second group (group II) is represented by the structurally characterized mbs from *Methylocystis* strains SB2, *rosea* and SC2 (FIGS. 11, 12). This mb group lack the Cys in the core peptide, are smaller and probably less rigid, due to the absence of the disulfide bond found in mb-OB3b. In this group the rings are separated by two amino acids. In contrast to the other members of group II mbs, mb-B-8, mb-14-3, mb-B510 and mb-21721 contain 4 Cys. However, based on the location of the Cys we predict all 4 Cys are modified into the heterocyclic rings. Mbs from the structurally characterized members in this group contain a sulfate group, which may aid in the formation of a tight bend by making a hydrogen bond with the backbone amide of Ser2. The sulfate group also increases $Cu^{2+/1+}$ affinity (El Ghazouani et al., 2012. Proc. Nat. Acad. Sc. 109: 8400). The conserved T/S adjacent to the C-terminal ring suggests that the other members of this group also contain a sulfate group.

It was discovered that the genome region of the putative mb precursor matching sequence in *M. trichosporium* OB3b had a number of distinctive and striking features (FIG. 13). These include (a) a precursor peptide translationally modified peptide; (b) a potential cleavage site between the leader and core peptide, suggestive of secretion; (c) genes upstream and downstream of the mb gene cluster encoding protein sequences compatible with possible roles in maturation of the mb precursor sequence, transport, and regulation of mb biosynthesis. Elaboration on this initial search revealed a series of genomes containing gene clusters with characteristics matching that of the *M. trichosporium* OB3b mb gene cluster, e.g. in *Methylocystis parvus* OBBP *Methylosinus* sp. LW3 as well as non-methanotrophs *Azospirillum* sp. B510, *Azospirillum* sp. B506, *Pseudomonas extremaustralis Pseudomonas extremaustralis* substrain *laumondii* TT01 *Tistrella mobilis, Gluconacetobacter* sp. SXCC. *Gluconacetobacter oboediens Methylobacterium* sp. B34, *Cupriavidus basilensis* B-8, *Photorhabdus luminescens* and *Vibrio caribbenthicus* BAA-2122.

At present the only genes in the *Methylosinus trichosporium* OB3b mb gene cluster with a known function are the structural gene for mb-OB3b, MbnA, and TonB-transporter (MbnT) which is responsible for $Cu^+$-mb-OB3b uptake (Semrau et al., unpublished results). The cytochrome c peroxidase MbnH, and the FAD'-dependent oxidoreductase, present instead or sometimes in addition to MbnH in methanotroph gene clusters MbnF are likely candidates to be involved in the oxidation steps required for ring formation. In addition, the aminotransferase MbnN found in the mb-OB3b, but not the mb-SB2 gene cluster may be involved in formation of the N-terminal keto-isopropyl group, and the sulfotransferase MbnS found in the mb-SB2 and mb-*rosea*, but not the mb-OB3b gene cluster may catalyse sulfonation of the threonine. One other gene product, the multidrug and toxin extrusion (MATE) protein has been suggested to be involved in secretion of mature mbs.

Generally, the present invention encompasses methanobactins encoded by a mb gene, preferably a *Methylosinus trichosporium* OB3b mb gene or variant or ortholog thereof. The term "variant" in reference to a nucleic acid sequence refers to polymorphisms, i.e. the exchange, deletion, or insertion of one or more nucleotides, respectively, as compared to the "parent" nucleic acid sequence that the variant is derived from. "Orthologs", or orthologous genes, are genes in different species that evolved from a common ancestral gene by speciation. As used herein a variant or ortholog encodes a copper-binding methanobactin preferably exhibiting the same advantageous properties as the mb evaluated in the appended examples. It is envisaged that the variant or ortholog of the mb-OB3b gene comprises or consists of a nucleic acid sequence having at least about 60%, such as at least about 65%, 70%, 75%, 80%, 85%, 90%, 95% or 99% sequence identity to the mb gene.

The mb OB3b gene, variant or ortholog thereof is envisaged to encode an mb precursor peptide that comprises or consists of an amino acid sequence that has at least about 60%, such as at least about 65%, 70%, 75%, 80%, 85%, 90%, 95% or 99% sequence identity to the amino acid sequence of the known mb-OB3b precursor peptide with UniProt Acc. No. E3YBA4 (entry version No. 15 of Jun. 24, 2015) and as depicted in SEQ ID No. 1 (FIG. 12). Particularly, and as described in more detail below, the mb OB3b gene was found to encode a precursor peptide including a leader peptide and a core peptide, separated by a potential cleavage site. Preferred % sequence identities for the overall precursor peptide are indicated above. Moreover, the encoded (i.e., non-translationally modified) methanobactin (i.e., core peptide) is envisaged to comprise or consist of an amino acid sequence that has at least about 60%, such as at least about 65%, 70%, 75%, 80%, 85%, 90%, 95% or 99% sequence identity to the amino acid sequence of the known mb-OB3b core precursor peptide as depicted in SEQ ID No. 1 (FIG. 12).

Generally, the term "sequence identity" indicates the extent to which two (nucleotide or amino acid) sequences have identical residues at the same positions in an alignment, and is often expressed as a percentage. Preferably, identity is determined over the entire length of the sequences being compared. Thus, two copies of exactly the same sequence have 100% identity, but sequences that are less highly conserved, and have deletions, additions, or replacements, may have a lower degree of identity. Those skilled in the art will recognize that several algorithms are available for determining sequence identity using standard parameters, for example Blast (Altschul, et al. (1997) Nucleic Acids Res. 25:3389-3402), Blast2 (Altschul, et al. (1990) J. Mol. Biol. 215:403-410), Smith-Waterman (Smith, et al. (1981) J. Mol. Biol. 147:195-197) and ClustalW. Accordingly, for instance, the amino acid sequences of SEQ ID No: 1 may serve as "subject sequence" or "reference sequence", while the amino acid sequence or nucleic acid sequence of a polypeptide or polynucleotide different therefrom can serve as "query sequence".

A high affinity for copper is a common feature of methanobactins. Therefore, methanobactins of the invention are envisaged to bind copper—specifically Cu(I)—with high binding affinity. The term "affinity" or "binding affinity" refers to the strength of the binding of a ligand, such as a methanobactin to Cu(I). The affinity of the binding of a given ligand to its target is often determined by measurement of the on-rate constant ($k_{on}$) and off-rate constant ($k_{off}$) and calculating the quotient of $k_{off}$ to $k_{on}$ to obtain the equilibrium dissociation constant $K_d$ ($K_d=k_{off}/k_{on}$) which is inversely related to the binding affinity, i.e. the lower the $K_d$ value, the higher the binding affinity. Preferred methanobactins of the invention bind Cu(I) with an equilibrium dissociation constant or $K_d$ in the nanomolar range, i.e. $10^{-7}$, $10^{-8}$, $10^{-9}$, in the picomolar range, i.e. $10^{-10}$, $10^{-11}$, $10^{-12}$, or in the femtomolar range, i.e. $10^{-13}$, $10^{-14}$, $10^{-15}$. Preferably, methanobactins of the invention bind Cu(I) with a $K_d$ in the femtomolar range, and are particularly envisaged to bind Cu(I) with a $K_d$ of $10^{-15}$ or less. A number of different methods have been used to determine metal binding affinity constants for mbs. All measurement methods show Cu(II)/(I) and Cu(I) affinities of ~$10^{21}$ M$^{-1}$ or greater, and is one of the highest known for biological systems. With respect to this proposal, mb-OB3b has been shown to remove Cu from metallothionein in both in vitro and in vivo experiments. Mbs have been shown to solubilize and bind insoluble forms of Cu(I) under anaerobic conditions, and to extract Cu from copper minerals, humic materials, and glass Copper (Cu(I)) binding affinity can for example be measured according the ESI-MS approach of Banci et al. (Nature. 2010 Jun. 3; 465(7298):645-8) which relies on the simultaneous monitoring of the variation in the metallated/non-metallated Cu(I) binding ligand ratios at increasing concentrations of a competing ligand, namely dithiothreitol (DTT) or diethyl-dithiocarbamate (DETC). Alternatively, Cu(I) binding affinities can for example be determined from competition titrations with the chromophoric copper chelator bathocuproine disulfonate (BCS) as described by El Ghazoiani A et al., Proc Natl Acad Sci USA. 2012 May 29; 109(22):8400-4. Measuring Cu(I) binding affinities with this method, methanobactins encompassed by the present invention will also exhibit a $K_d$ of $10^{-15}$ or less, such as $10^{-16}$, $10^{-17}$, $10^{-18}$, $10^{19}$, $10^{-20}$, $10^{-21}$ or less.

As set out previously herein, methanobactins exhibiting high copper binding affinities (and binding Cu(I) with a $K_d$ of $10^{-15}$ or less, "high-affinity mb") are particularly envisaged for the uses according to the present invention, and in particular for massive copper depletion in (acute) WD therapy. However, methanobactins with a higher $K_d$ (i.e. binding Cu(I) with a lower affinity) can also be successfully employed in treatment of a variety of diseases. E.g., in cases when a less extensive and/or quick copper depletion is desired, methanobactins with a lower binding affinity towards Cu(I) ("low-affinity mb") can be utilized. It is also contemplated to combine methanobactins with different Cu(I) binding affinities for treatment. E.g., one or more treatment cycles with a high-affinity mb for extensive removal of copper from a patient can be followed by one or more treatment cycles with a low-affinity mb for maintenance therapy in order to keep copper levels low without excessively depleting copper. Vice versa, treatment could also be started with low-affinity mb and, after one or more treatment cycles, optionally gradually be continued using mbs with a higher Cu(I) binding affinity.

The term "methanobactin" includes naturally occurring methanobactins and functional variants, fragments and derivatives thereof which retain the capability of complexing copper (i.e., Cu(I) and Cu(II)), and preferably bind Cu(I) with a binding affinity that is comparable or even higher than that of the naturally occurring methanobactins.

As set forth previously, the methanobactin of the invention may be derived from bacteria listed in FIG. 12, including *Methylocystis* spec., *Methylosinus* spec., *Methylomicrobium* spec. and *Methylococcus* spec. Particularly, the methanobactin may be selected from (a) a *Methylosinus trichosporium* OB3b methanobactin (mb-OB3b) (b) a *Methylocystis*. strain SB2 methanobactin (mb-SB2), (c) a *Methylococcus capsulatus* Bath methanobactin (mb-Bath) (d) a *Methylomicrobium* album BG8 methanobactin (mb-BG8), (e) a *Methylocystis* strain M methanobactin, (f) a *Methylocystis hirsuta* CSC1 methanobactin and (g) a *Methylocystis rosea* methanobactin (mb-*rosea*), (h) a *Methylosinus* sp. strain LW3 methanobactin (mb-LW3), (i) a *Methylosinus* sp. strain LW4 methanobactin (mb-LW4), (j) a *Methylocystis* sp. strain LW5 (mb-LW5), (k) a *Methylosinus* sp. strain PW1 methanobactin (mb-PW1), (l) a *Methylocystis parvus* OBBP methanobactin (mb-OBBP), (m) a *Cupriavidus basiliensis* B-8 methanobactin (mb-B-8), (n) a *Pseudomonas extremaustralis* 14-3 methanobactin (mb-14-3), (o) a *Azospirillum* sp. stain B510 methanobactin (mb-B510), (p) a *Tistrella mobilis* KA081020-065 (mb-*mobilis*) methanobactin and (q) a *Comamonas composti DSM* 21721 methanobactin (mb-21721).

Methanobactins selected for the uses according to the present invention preferably have the same advantageous properties as the mb evaluated in the appended examples and/or as described elsewhere herein.

In general, methanobactin of the invention may comprise, or consist of, the following general formula (I):

$$R^1 - (X)_{2-5} - R^2 \qquad (I)$$

wherein
R$^1$ and R$^2$ are each a 5-membered heterocycle comprising N and associated with an enethiolate;
and each X is independently selected from any amino acid.

The term "amino acid" or "amino acid residue" typically refers to an amino acid having its recognized definition such as an amino acid selected from the group consisting of: alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (Ile or I): leucine (Leu or L); lysine (Lys or K); methionine (Met or M); phenylalanine (Phe or F); pro line (Pro or P); serine (Ser or S); threonine (Thr or T); tryptophan (Trp or W); tyrosine (Tyr or Y); and valine (Val or V), although modified, synthetic, or rare amino acids may be used as desired. Generally, amino acids can be grouped as having a nonpolar side chain (e.g., Ala, Ile, Leu, Met, Gly, Phe, Pro, Val); a negatively charged side chain (e.g., Asp, Glu); a positively charged sidechain (e.g., Arg, His, Lys); or an uncharged polar side chain (e.g., Asn, Cys, Gln, Ser, Thr, Trp, and Tyr). The term encompasses naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Particularly, where the methanobactin is mb-OB3b, it is contemplated to comprise or consist of the formula (II)

$$R^1GSCYR^2SCM \qquad (II),$$

wherein $R^1$ is selected from (N-2-isopropylester-(4-thionyl-5-hydroxy-imidazole) and N-2-isopropylester-(4-thiocarbonyl-5-hydroxy-imidazolate), and $R^2$ is selected from pyrrolidine-(4-hydroxy-5-thionyl-imidazole) and pyrrolidine-(4-hydroxy-5-thiocarbonyl-imidazolate). Said mb-OB3b may in particular comprise or consist of the formula (IV):

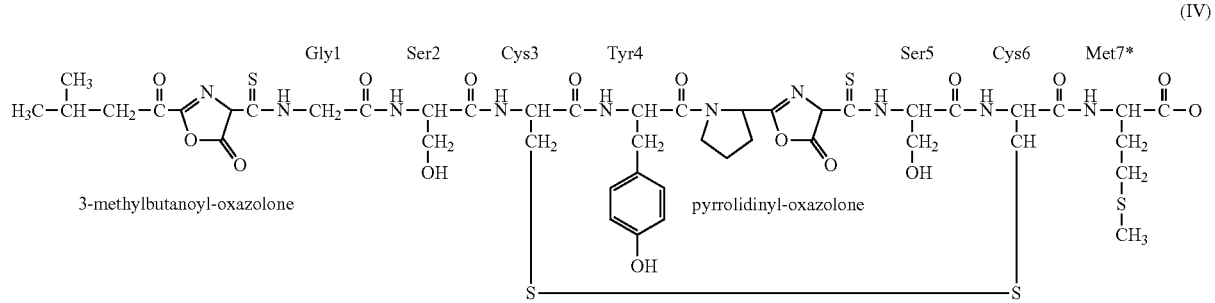 [SMILES: CSCCC(NC(=O)C1CSSCC(NC(=O)C(CO)NC(=O)CNC(=S)C2N=C(C(=O)CC(C)C)OC2=O)C(=O)NC(Cc2ccc(O)cc2)C(=O)N2CCCC2C2=NC(C(=O)O2)C(=S)NC(CO)C(=O)N1)C(=O)O]

(IV)

When complexing zinc or copper, said mb-OB3b is envisaged to have the following structure (VI)

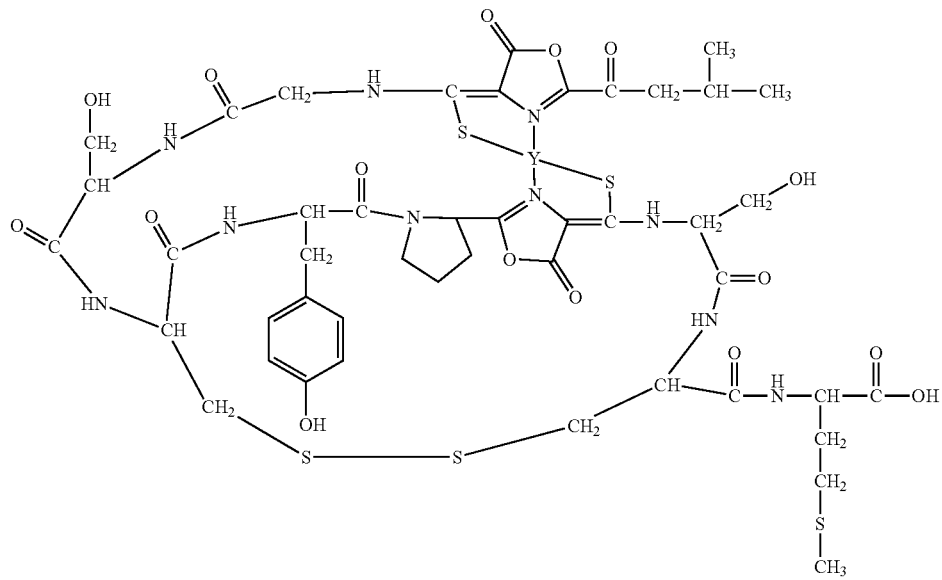

(VI)

wherein Y is selected from copper (Cu(I) or Cu(II)) or zinc (Zn(I) or Zn(II)).

Where the methanobactin is mb-SB2, it is envisaged to be of the formula (III)

$$R^1ASR^2AA \qquad (III)$$

wherein $R^1$ is 4-guanidinobutanoyl-imidazole and $R^2$ is 1-amino-2-hydroxy-oxazolone.

Said mb-SB2 may in particular be of the formula (V):

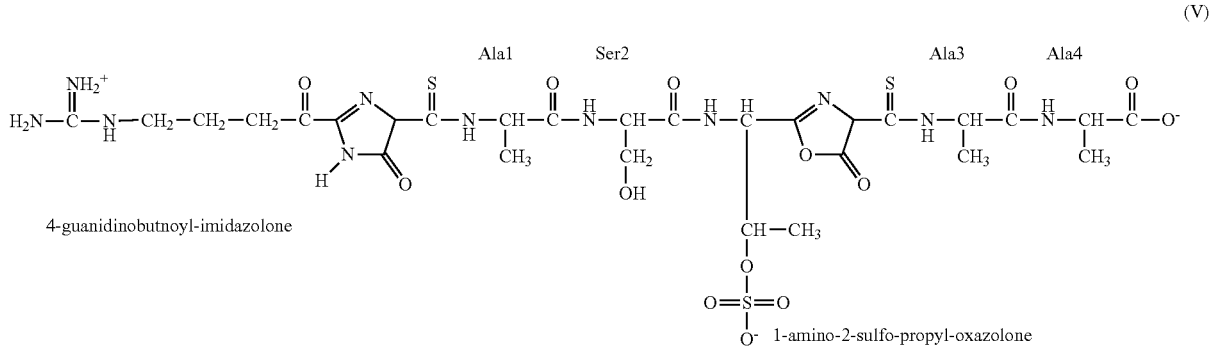

When complexing zinc or copper, said mb-SB2 is envisaged to have the following structure (VII):

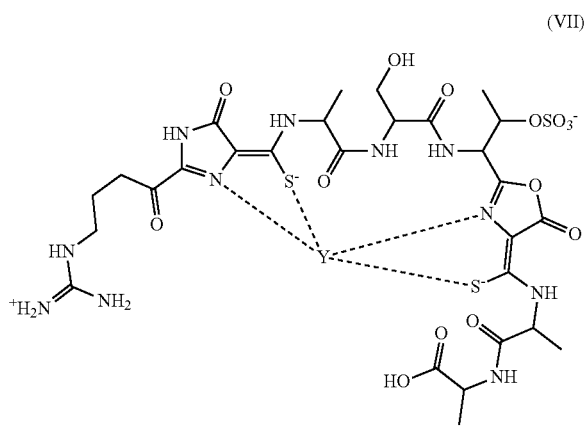

wherein Y is selected from copper (Cu(I) or Cu(II)) or zinc (Zn(I) or Zn(II)).

This specific MB peptide mb-SB2 from *Methylocystis* strains SB2 acts most effectively as a promising copper chelator compared to existing clinically approved cooper chelators such as D-PA. mb-SB2 even depletes copper at least as effective as another MB peptide mb-OB3b derived from *Methylosinus trichosporium* OB3b, as mentioned above.

MB peptide mb-SB2 from *Methylocystis* strains SB2 is structurally and chemically deviating from other MB peptides, especially from mb-OB3b derived from *Methylosinus trichosporium* OB3b). Yet, a structurally different and less heavy peptide within the MB-family exhibits a similar therapeutic potential as a copper chelator.

When used herein, the terms "complexing" and "binding" are used interchangeably, i.e. for instance a methanobactin "binding" copper is to be understood as a methanobactin "complexing" copper, and vice versa. The term "complexing" generally means forming a complex consisting of a central ion and surrounding array of molecules that are known as ligands or complexing agents. For the present invention, the central ion will be copper (i.e. Cu(I) or Cu(II)), or zinc (i.e. Zn(I) or Zn(II)) and the ligand will be methanobactin. One methanobactin will typically complex one copper or zinc ion, forming a methanobactin-copper complex or a methanobactin-zinc complex, respectively. The person skilled in the art will readily understand that methanobactin-copper complexes will typically form after administration of the methanobactin to the subject, when methanobactin complexes and thereby depletes (excess) copper in the subject's body. Methanobactin-zinc complexes are envisaged herein as stabilized forms of methanobactin as described below.

As set out elsewhere herein, methanobactin fragments, variants and derivatives are also envisioned for the uses described herein.

"Methanobactin fragments" are "functional" or "copper-binding" peptides that retain the copper-binding region of the "parent" methanobactin they are derived from. It is for instance envisaged to provide particularly small methanobactin fragments that are capable of crossing the blood-brain-barrier in order to effectively treat neurological WD or other conditions associated with copper overload in the CNS.

The term "methanobactin variant" refers to methanobactins having the general methanobactin formula of a "parent" methanobactin (FIG. 12), but containing at least one amino acid substitution, deletion, or insertion as compared to the parent methanobactin, provided that the variant retains the desired copper-binding affinity and/or biological activities described herein.

"Methanobactin derivatives" are chemically modified methanobactins. Generally, all kind of modifications are comprised by the present invention as long as they do not abolish the beneficial effects of the methanobactins. That is, methanobactin derivatives preferably retain the copper-binding affinity and/or biological activity of the methanobactins they are derived from. Methanobactin derivatives also include stabilized methanobactins as described in the following.

Possible chemical modifications in the context of the present invention include acylation, acetylation or amidation of the amino acid residues. Other suitable modifications include, e.g., extension of an amino group with polymer chains of varying length (e.g., XTEN technology or PASylation®), N-glycosylation, O-glycosylation, and chemical conjugation of carbohydrates, such as hydroxyethyl starch (e.g., HESylation®) or polysialic acid (e.g., PolyXen® technology). Chemical modifications such as alkylation (e.g., methylation, propylation, butylation), arylation, and etherification may be possible and are also envisaged. Further chemical modifications envisaged herein are ubiquitination, conjugation to therapeutic or diagnostic agents, labeling (e.g., with radionuclides or various enzymes), and insertion or substitution by chemical synthesis of non-natural amino acids.

Other possible modifications may involve replacement of oxazolone group with the more stable imidazolone or pyrazinedione group. Gene additions and/or deletions of genes from the operons of Group II methanobactins into Group I or vice versa should result in alteration may result in a change in the type of ring. Replacement of oxazolone group(s) with either imidazolone or pyrazinedione group(s) should increase the stability of methanobactin to the point where oral administration may be possible.

For the purpose of the invention the methanobactin as defined above also includes the pharmaceutically acceptable salt(s) thereof. The phrase "pharmaceutically acceptable salt(s)", as used herein, means those salts of methanobactins that are safe and effective for treatment. Pharmaceutically acceptable salts include those formed with anions such as those derived from hydrochloric, phosphoric, acetic, oxalic, tartaric acids, choline etc., and those formed with cations such as those derived from sodium, potassium, ammonium, calcium, ferric hydroxides, isopropylamine, triethylamine, 2-ethylamino ethanol, histidine, procaine, etc.

As set forth previously, the methanobactin fragments, variants and derivatives preferably retain the advantageous capabilities of the methanobactins evaluated in the appended examples.

Biological Effect

As explained previously, methanobactins according to the present invention are envisaged to elicit the desired biological effects as described herein, i.e. they are preferably capable of binding copper with a high binding affinity, and effecting its depletion from the system and preferably its excretion via the bile. Without wishing to be bound by specific theory, the present inventors have established that mitochondrial impairment due to an increased copper load progressively increases with disease state in livers from LPP−/− rats, a model of WD. As shown in the appended examples, methanobactins are able to rapidly deplete mitochondrial and hepatocellular copper. It is envisaged that methanobactins as described herein preferably exhibit the same advantageous characteristics.

Thus, methanobactins are envisaged for the use of treatment of Wilson Disease, wherein the treatment reduces (i) whole liver copper levels, (ii) overall hepatocyte copper levels and/or (iii) hepatocyte mitochondrial copper levels. Moreover, methanobactins will preferably effect excretion of (excess) copper via the bile.

Therapeutic Effect

Administration of methanobactins to subjects in need thereof (in particular WD patients) is expected to elicit a therapeutic effect. The term "therapeutic effect" as used herein generally refers to a desirable or beneficial impact of a treatment, e.g. amelioration or remission of the disease manifestations. The term "manifestation" of a disease is used herein to describe its perceptible expression, and includes both clinical manifestations, hereinafter defined as indications of the disease that may be detected during a physical examination and/or that are perceptible by the patient (i.e., symptoms), and pathological manifestations, meaning expressions of the disease on the cellular and molecular level. Amelioration or remission of WD manifestations can be assessed by using the same tests as described for diagnosis of WD. Additionally or alternatively it is also possible to evaluate the general appearance of the respective patient (e.g., fitness, well-being) which will also aid the skilled practitioner to evaluate whether a therapeutic effect has been elicited. The skilled person is aware of numerous other ways which are suitable to observe a therapeutic effect of the compounds of the present invention.

Stabilized Methanobactin

In a further aspect, the present inventors have discovered ways to provide methanobactins in stabilized form.

Without wishing to be bound by specific theory, it was discovered that mb-OB3b is susceptible to time- and/or temperature-dependent decay. Thus, in order to allow an increased biological half-life and/or plasma concentration of methanobactins in the subject's body during (and after) treatment, and therefore preferably improve therapeutic efficacy and provide for a long-term effect of methanobactin treatment, it is envisaged to provide stabilized forms of methanobactin. Generally, any form of chemical modification is conceivable that enables stabilization of the methanobactins (see also methanobactin derivatives). Specifically, the present invention provides stabilized forms of methanobactins complexing zinc, i.e. Zn(I) or Zn(II). Unless denoted otherwise, the term "zinc" generally refers to Zn(I) and/or Zn(II). Furthermore, the present inventors found that methanobactins can be stabilized when provided at a pH of 9. Thus, it is envisaged to provide stabilized forms of methanobactins, i.e. methanobactins complexing Zn(I) or Zn(II) and/or being provided at a pH of 9, 10, or 11, for the uses and methods of the present invention. In particular, such stabilized forms of methanobactins can be used for treatment of WD according to the treatment regimen set out elsewhere herein, and/or for treatment of acute phase WD. Stabilized forms of methanobactins as described herein have not been used as medication before. The present invention thus also comprises a pharmaceutical composition comprising a stabilized methanobactin, wherein said methanobactin complexes Zn(I) and/or Zn(II) and/or is provided at a pH≥9. The skilled practitioner will readily understand that when the methanobactin is provided at a pH≥9 for reasons of stabilization, the pharmaceutical composition comprising methanobactin (optionally complexing zinc) is required to have a pH≥9, too.

A pharmaceutical composition comprising a methanobactin complexing Zn(I) or Zn(II) can be provided by contacting an amount of Zn(I) and/or Zn(II) and an amount of methanobactin in a ratio of 1:1 in aqueous solution. Use of equimolar amounts of zinc and methanobactin may be beneficial in order to avoid an excess amount of free zinc ions in the pharmaceutical composition.

Pharmaceutical Composition

As set out in the foregoing, a pharmaceutical composition comprising methanobactin, in particular in stabilized form, is also envisaged herein. In particular, said pharmaceutical composition is envisaged for the use of treatment of Wilson Disease, wherein the treatment reduces (i) whole liver copper levels, (ii) overall hepatocyte copper levels and/or (iii) hepatocyte mitochondrial copper levels. I.e., the pharmaceutical composition preferably comprises methanobactins complexing Zn(I) or Zn(II) and/or are provided in a pH 9. Said composition may be stable at 37° C. for at least 20, 50, 75, 100, 125, 150 hours or more. Accordingly, further aspects of the invention include a pharmaceutical composition comprising (in particular, stabilized) methanobactin as described herein and the use of the said (stabilized) methanobactin for the manufacture of a pharmaceutical composition. The term "pharmaceutical composition" particularly refers to a composition suitable for administering to a human. However, compositions suitable for administration to non-human animals are also envisaged herein.

The pharmaceutical composition and its components (i.e. active ingredients and optionally excipients or carriers) are preferably pharmaceutically acceptable, i.e. capable of eliciting the desired therapeutic effect without causing any undesirable local or systemic effects in the recipient. Pharmaceutically acceptable compositions of the invention may in particular be sterile and/or pharmaceutically inert. Specifically, the term "pharmaceutically acceptable" may mean approved by a regulatory agency or other generally recognized pharmacopoeia for use in animals, and more particularly in humans.

The (stabilized) methanobactin described herein is preferably present in the pharmaceutical composition in a therapeutically effective amount. By "therapeutically effective amount" is meant an amount of methanobactin that elicits the desired therapeutic effect. The exact amount dose will depend on the purpose of the treatment, and will be ascertainable by one skilled in the art using known techniques. Therapeutic efficacy and toxicity can be determined by standard pharmaceutical procedures in cell cultures or experimental animals, e.g., $ED_{50}$ (the dose therapeutically effective to 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are generally preferred.

The pharmaceutical composition is envisaged to comprise a methanobactin as described herein, particularly in stabilized form, and preferably in a therapeutically effective amount, optionally together with one or more carriers, excipients and/or additional active agents.

"Excipients" include fillers, binders, disintegrants, coatings, sorbents, antiadherents, glidants, preservatives, antioxidants, flavoring, coloring, sweeting agents, solvents, co-solvents, buffering agents, chelating agents, viscosity imparting agents, surface active agents, diluents, humectants, carriers, diluents, preservatives, emulsifiers, stabilizers and tonicity modifiers. Exemplary suitable carriers for use in the pharmaceutical composition of the invention include saline, buffered saline, dextrose, and water.

Additional Active Agents

The pharmaceutical composition may also comprise further active agents effective for treatment of the particular disease concerned. By way of example, active agents presently used for treatment of WD include the copper chelators d-penicillamine (D-PA), trientine (TETA) and tetrathiomolybdate (TTM), as well as zinc salts. For treatment of cancer, useful additional active agents include known chemotherapeutic agents, including alkylating agents, antimetabolites, anti-microtubule agents, topoisomerase inhibitors; cytotoxic antibiotics, and monoclonal antibodies. Active agents for treatment of neurodegenerative disorders include, without limitation, levodopa and derivatives thereof, dopamine agonists, MAO-B inhibitors, catechol-O-methyltransferase (COMT) inhibitors, anticholinergics, amantadine, cholinesterase inhibitors, memantine and riluzole. It is within the knowledge of the skilled person to choose suitable additional agents for treatment of a specific disease.

Formulation

The pharmaceutical compositions of the invention can be formulated in various forms, e.g. in solid, liquid, gaseous or lyophilized form and may be, inter alia, in the form of an ointment, a cream, transdermal patches, a gel, powder, a tablet, solution, an aerosol, granules, pills, suspensions, emulsions, capsules, syrups, liquids, elixirs, extracts, tincture or fluid extracts or in a form which is particularly suitable for the desired method of administration. Processes known per se for producing medicaments are indicated in Forth, Henschler, Rummel (1996) Allgemeine und spezielle Pharmakologie und Toxikologie, Urban & Fischer.

Administration

A variety of routes are conceivable for administration of the methanobactins and pharmaceutical compositions according to the present invention. Typically, administration will be accomplished parentally, but oral administration is also envisaged. Methods of parenteral delivery include topical, intra-arterial, intramuscular, subcutaneous, intramedullary, intrathecal, intraventricular, intravenous, intraperitoneal, intrauterine, intravaginal, sublingual or intranasal administration.

Cancer Treatment

The methanobactins and pharmaceutical composition disclosed herein is also envisaged for treatment of various cancers. Many cancer types exhibit increased intratumoral copper and/or altered systemic copper distribution. It has been acknowledged that copper serves as a limiting factor for multiple aspects of tumor progression, including growth, angiogenesis and metastasis. Methanobactins and pharmaceutical compositions described herein are thus promising tools to inhibit these processes.

As reviewed by Denoyer et al., Metallomics. 2015 Nov. 4; 7(11):1459-76, high serum copper concentrations are reportedly associated with a variety of cancers including lymphoma, reticulum cell sarcoma, bronchogenic and laryngeal squamous cell carcinomas, cervical, breast, stomach and lung cancers, and elevated serum copper has been found to correlate with the stage of the disease and its progression in colorectal and breast cancers as well as hematological malignancies, including chronic lymphoid leukemia, non-Hodgkin's lymphoma, multiple myeloma and Hodgkin's lymphoma. Elevated copper in malignant tissues has also been established in a range of cancer types, including breast, ovarian, cervical, lung, stomach and leukemia. The role of copper in cancer development and progression remains to be elucidated. Elevated levels of redox active copper may lead to oxidative stress and chronic inflammation which are intrinsically linked to malignant transformation of cells. Therefore, it has been proposed that elevated copper in tissues or serum may be a risk factor for carcinogenesis. Methanobactins and pharmaceutical compositions described herein could be used to reduce overall copper levels and thereby minimize the risk for developing cancer.

Copper has also been reported to influence various molecular pathways inducing a pro-angiogenic response. Copper is capable of directly binding to angiogenic growth factors, and to influence their secretion and expression via activation of NFκB. Moreover, copper has been found to directly influence the ability of cancerous cells to invade and metastasize.

Papa et al., Genes Cancer. 2014 April; 5(1-2):15-21 further reported that the copper-dependent dismutase SOD1 is overexpressed in many cancers to cope with elevated levels of reactive oxygen species (ROS) caused by deregulation of the anti-oxidant machinery of the mitochondrial matrix. Depletion of copper is envisioned to reduce overall SOD1 activity, and thereby diminishing tumor cell proliferation and survival. In accordance, methanobactins and pharmaceutical compositions described herein are also envisaged for treatment of cancers which overexpress SOD1.

Known copper-chelating agents (such as D-PA) have been investigated for their capacity to control angiogenesis and thus by inference, to impair cancer growth and metastasis. However, methanobactins and pharmaceutical compositions described herein have not been elucidated for cancer treatment before. Further provided herein is therefore the use of methanobactins and pharmaceutical compositions described herein for treatment of various cancers, including without limitation, reticulum cell sarcoma, bronchogenic and laryngeal squamous cell carcinomas, cervical, breast, colorectal, stomach, lung cancers, liver cancer, prostate cancer, brain cancer, chronic lymphoid leukemia, non-Hodgkin's lymphoma, multiple myeloma and Hodgkin's lymphoma.

Neurodegenerative Disorders

Protein aggregation is a notable feature of various neurodegenerative disorders, including Parkinson disease, Alzheimer disease, Prion Disease including Creutzfeldt-Jakob disease (CJD), fatal familial insomnia (FFI), and Gerstmann-Straussler-Scheinker syndrome (GSS), familial amyotrophic lateral sclerosis (fALS) and many others. An increasing number of studies suggest that transition metals are able to accelerate the aggregation process of several proteins found in pathological deposits, and that in particular copper produces a most remarkable acceleration of aggregation. Hence, copper depletion by methanobactin treatment is therefore contemplated to reduce protein aggregation, thereby alleviating or even revert signs and symptoms of the disease.

It is therefore further envisaged to use methanobactins and pharmaceutical compositions described herein for treatment of neurodegenerative diseases including Parkinson Disease, Alzheimer Disease, Prion Disease, Huntington Disease and fALS.

Diabetes

Moreover, defective copper regulation has been suggested as a causative mechanism of organ damage in diabetes which has been attributed to impaired anti-oxidant defence mechanisms and oxidative stress. Strikingly, TETA treatment was shown to act on mitochondrial proteins with roles in energy metabolism in diabetes patients, and resulted in restoration of cardiac structure and function (Jullig et al., Proteomics Clin Appl. 2007 April; 1(4):387-99). As demonstrated in example 3 of the present application, methanobactins are surprisingly capable of efficiently removing accumulated mitochondrial copper—and are therefore, too, promising agents for a novel diabetes therapy based on the depletion of excess copper levels, particularly from the mitochondria, thereby reducing overall oxidative stress and tissue damage. In line with previous studies, methanobactins are particularly envisaged to improve diabetic cardiomyopathy and arterial and/or renal structure/function and to ameliorate left-ventricular (LV) hypertrophy in diabetic patients (see Zhang et al. Cardiovasc Diabetol. 2014 Jun. 14; 13:100).

Other Disorders

Further disease and disorders eligible for treatment with methanobactin and pharmaceutical compositions described herein comprise bacterial infections, inflammatory diseases, fibrosis, cirrhosis, lead and/or mercury poisoning.

In particular, during bacterial infections macrophages release copper in an attempt to kill invading microbes through copper toxicity. This leads to the induction of copper stress responses in invading microbes (Gleason et al., PNAS 2014 April; vol. 111, no. 16:5866-5871). According to Gleason et al. (2014) this high level of host copper is favorable for SOD5 activation of *C. albicans*. *C. albicans* is the most prevalent human fungal pathogen—a yeast fungus—, which is able to combat the host immune response (e.g. macrophages) with its expressed superoxide dismutase 5 (SOD5), a monomeric copper-only SOD. Depletion of copper is therefore more importantly to reduce overall SOD5 activity, thus reducing human fungal pathogens during bacterial infections. In accordance, methanobactins and pharmaceutical compositions described herein are also envisaged for treatment of human fungal pathogens during bacterial infections such as *C. albicans*, which overexpresses SOD5.

Therefore, the present invention encompasses a pharmaceutical composition, wherein bacterial infections are favorable for human fungal pathogens, preferably said human fungal pathogen is *Candida albicans*.

Treatment

The term "treatment" in all its grammatical forms includes therapeutic or prophylactic treatment of the diseases described herein, in particular WD. A "therapeutic or prophylactic treatment" comprises prophylactic treatments aimed at the complete prevention of clinical and/or pathological manifestations or therapeutic treatment aimed at amelioration or remission of clinical and/or pathological manifestations. The term "treatment" thus also includes the amelioration or prevention of the diseases described herein, specifically WD.

The terms "subject" or "individual" or "animal" or "patient" are used interchangeably herein to refer to any subject, particularly a mammalian subject, for whom therapy is desired. Mammalian subjects include humans, non-human primates, dogs, cats, guinea pigs, rabbits, rats, mice, horses, cattle and the like, with human subjects being particularly envisaged for treatment according to the invention.

Dosage

The exact dose of methanobactin may depend on the purpose of the treatment (e.g. prophylactic or maintenance therapy vs. treatment of acute WD), and will be ascertainable by one skilled in the art using known techniques. Adjustments for route of administration, age, body weight, general health, sex, diet, time of administration, drug interaction and the severity of the condition may be necessary, and will be ascertainable with routine experimentation by those skilled in the art. In general, dosages of 1 mg/kg body weight (bw) may be capable of eliciting the desired therapeutic effect as described elsewhere herein. Exemplary dosages applicable in the uses and methods of the invention include doses between 1 mg/kg bw and 1000 mg/kg bw, such as between 1 mg/kg bw and 100 mg/kg bw, and particularly between 1 mg/kg bw and 50 mg/kg bw, such as 1, 2, 5, 10, 15, 20, 25, 30, 35, 40, 45 or 50 mg/kg bw.

Kit

It is also envisaged that methanobactins, in particular in stabilized form, and pharmaceutical compositions described herein can be provided as part of a kit. Accordingly, in a further aspect, the present invention also relates to a kit comprising methanobactins, specifically such in stabilized form, or pharmaceutical compositions comprising the same for the use of treatment of Wilson Disease, wherein the treatment reduces (i) whole liver copper levels, (ii) overall hepatocyte copper levels and/or (iii) hepatocyte mitochondrial copper levels.

The kit may be a kit of two or more parts, and comprises the methanobactins described previously, or a pharmaceutical composition comprising the same, and further active agents and/or pharmaceutical excipients. For instance, the kit may comprise one or more active agents or pharmaceutical compositions comprising the same useful for treating WD, such as d-penicillamine (D-PA), trientine (TETA) and tetrathiomolybdate (TTM), and/or zinc salts. The kit components may be contained in a container or vials. It is envisaged that the kit components are administered simultaneously, or sequentially, or separately with respect to the administration of the methanobactins or pharmaceutical compositions comprising the same. The present invention further encompasses the application of the kit components via different administration routes. E.g., conventional copper chelators may be administered orally, whereas the parenteral route of administration can be used for methanobactins.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range. It includes, however, also the concrete number, e.g., about 20 includes 20.

The term "less than" or "greater than" includes the concrete number. For example, less than 20 means less than or equal to. Similarly, more than or greater than means more than or equal to, or greater than or equal to, respectively.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

EXAMPLES

Materials and Methods
Patient-Derived Samples

Livers from four WD patients with liver failure transplanted at the University Hospital Heidelberg for Wilson disease were included in this study. Two patients (No. 1 and 2) had received no prior copper chelation therapy, while two patients (No. 3 and 4) presented with liver failure after D-PA treatment. Patients gave their informed consent, and the study was approved by the ethical committee of the Medical University of Heidelberg, Germany. Upon explantation, WD patient livers were shock frozen in LN2 and stored at −80° C. Thawed samples were immediately fixed for histological and electron microscopy analyses.

Animals

The LPP rat strain was provided by Jimo Borjigin, University of Michigan, Ann Arbor, USA (ahmed et al., log. cit.). Rats were maintained on an ad lib Altromin 1314 diet (Altromin Spezialfutter GmbH, Germany) and tap water. The copper content of the diet was 13 mg/kg. All animals were treated under the guidelines for the care and use of laboratory animals of the Helmholtz Center Munich. LPP−/− rats are provided with an ATP7b mutation and thus are ATP7b−/−. Heterozygous LPP+/− rats served as controls in this study.

Animal Treatments

Animal experiments were approved by the government authorities of the Regierung von Oberbayern, Munich, Germany.

In Vivo Treatments

LPP rats were treated with MB either by daily i.p. injections for 3 or 5 consecutive days, or twice daily i.p. injections for 8 consecutive days at a dose of 150 mg/kg bw or 4 days via the drinking water with D-PA at a dose of 100 mg/kg bw/d or TETA at 480 mg/kg bw/d, respectively (Togashi et al., Hepatology 15, 82-87 (1992)). Based on a mean copper content of 250 µg/g w.w. in Atp7b−/− rat livers at the age of treatment start (Zischka et al., log. cit.), a LPP−/− rat liver of 8 g w.w. contains around 31.5 µmol copper. Single MB doses were chosen equimolar to this copper amount. In case of D-PA the administered dose and chosen application route has been reported to successfully prevent the onset of hepatitis in LEC rats in long-term applications (Togashi et al., log. cit.). Subchronic toxicity studies in rats have revealed no toxicity of TETA at a dose of 3000 ppm via the drinking water (Greenman et al., Fundam Appl Toxicol 29, 185-193 (1996)). Assuming 40 ml water intake per day for a rat weighing 250 g this translates to a dose of 480 mg/kg bw/d. With respect to the mean liver copper content in LPP−/− rats aged 85 days, the molar ratios of the chelators applied was MB 1:D-PA 4.3:TETA 17.4, respectively. For the intravenous MB application (150 mg/kg bw), catheters connected to a PinPort™ (Instech Laboratories, Inc., USA) were inserted in the femoral vein of the rat, fixed with non-absorbable sutures and subcutaneously tunneled and exteriorized through a skin incision made between the shoulders.

Liver Perfusion

LPP−/− livers (animal age 79-83 days) were perfused in a single pass manner with Krebs-Ringer bicarbonate solution containing 5 mM glucose (Beuers et al., J Biol Chem 278, 17810-17818 (2003)). The medium was gassed with 95% O2/5% CO2 and kept at 37° C. Rat livers were perfused via the portal vein (Beuers et al., log. cit.), the right lateral liver lobe was ligated and its copper content served as pre-perfusion control (Beuers et al., Hepatology 33, 1206-1216 (2001)). After cannulation of the bile duct a 20 min sample of bile was collected before the copper chelators were continuously added to the perfusion medium. Bile and outflow perfusate were collected in 10 min intervals as described elsewhere (Beuers et al., log. cit.). D-PA*HCl (20 mg/108 µmol), TETA*2HCl (20 mg/91 µmol), TTM*2NH4 (10 mg/38 µmol) and MB (40 mg/35 µmol) were each dissolved in 50 ml 0.9% NaCl, and continuously added to the perfusion medium via a perfusion pump (Perfusor, Braun, Melsungen) within 2 hours. The molar ratios of the chelators applied was MB 1:D-PA 3.1:TETA 2.6:TTM 1.1. LDH in the outflow perfusate was measured every ten minutes as described (Beuers et al., log. cit.). Control perfusions were done with Krebs-Ringer bicarbonate solution only.

Histological Examination, Plasma/Serum AST and Bilirubin

Formalin-fixed, paraffin-embedded liver samples were cut into 4 µm-thick sections and either stained with hematoxylin and eosin for standard analyses or with Masson trichrome for analysis of fibrotic tissue. AST activity and bilirubin concentration in animal plasma or serum were measured with a Reflotron system (Roche).

Mitochondrial Analyses

Mitochondria were derived either from frozen explanted livers from WD patients or from freshly prepared rat liver homogenates as described previously (Zischka et al., Anal Chem 80, 5051-5058 (2008)). Specifically, mitochondria were purified by differential and density gradient centrifugation using either Percoll® or Nycodenz®. Fresh rat liver mitochondria were used for respiratory measurements, chelator treatments, analyses of swelling (MPT), transmembrane potential (Lam), polarization experiments, ATP synthesis and fixed with glutaraldehyde for subsequent electron microscopy analyses. Stored frozen mitochondria were used for respiratory complex IV activity and metal analyses.

Functional integrity of isolated mitochondria was assessed by standard respiratory measurements in a Clark-type oxygen electrode (Oxygraph, Hansatech Instruments) (Zischka et al., log. cit.). Kit-based assays were used to analyze ATP synthesis (ATP Bioluminescence Assay Kit, Roche) (Zischka et al., log. cit.). Mitochondrial swelling was measured by light scattering with an absorbance reader in 96-well plate formats at 540 nm (Schulz et al., Biochimica et biophysica acta 1828, 2121-2133 (2013)). Assessment of $\Delta\psi m$ was followed by Rh123 fluorescence quenching in a 96-well plate reader (BioTek) (Schulz et al., log. cit.). Polarisation was measured in DPH and TMA-DPH-dyed mitochondria (Prendergast et al., log. cit.). In brief, mitochondria (3 mg/ml) were incubated for 30 minutes at 37° C. either with DPH or TMA-DPH (50 µM and 20 µM, respectively). Parallel and perpendicular fluorescence was assessed in duplicates at ex: 366 nm and em: 425 nm. Polarisation was calculated (Grebowski et al., Biochim Biophys Acta 1828, 241-248 (2013)) in mPol using the formula $$P=(I_\| - G*I_\perp)/(I_\| + G*I_\perp); G=0.89.$$

In Vitro Treatment of Isolated Mitochondria with Chelators

Freshly isolated density gradient purified LPP−/− mitochondria with elevated copper were subjected to chelator treatments for 30 min with either 2 mM D-PA, TETA, TTM or MB, and subsequently re-purified by a Nycodenz®-gradient to separate copper in solution from copper incorporated into mitochondria. In validation experiments, mitochondria from control rats (LPP+/−) were incubated with 1 mM DTT for 5 min at RT and thereafter $Cu^{2+}$ was added (final concentrations 200-600 µM) for additional 20 min. Copper loaded mitochondria were then re-purified by Nycodenz®-gradient centrifugation and subsequently treated with chelators as above.

Cell Culture

Figure 9:
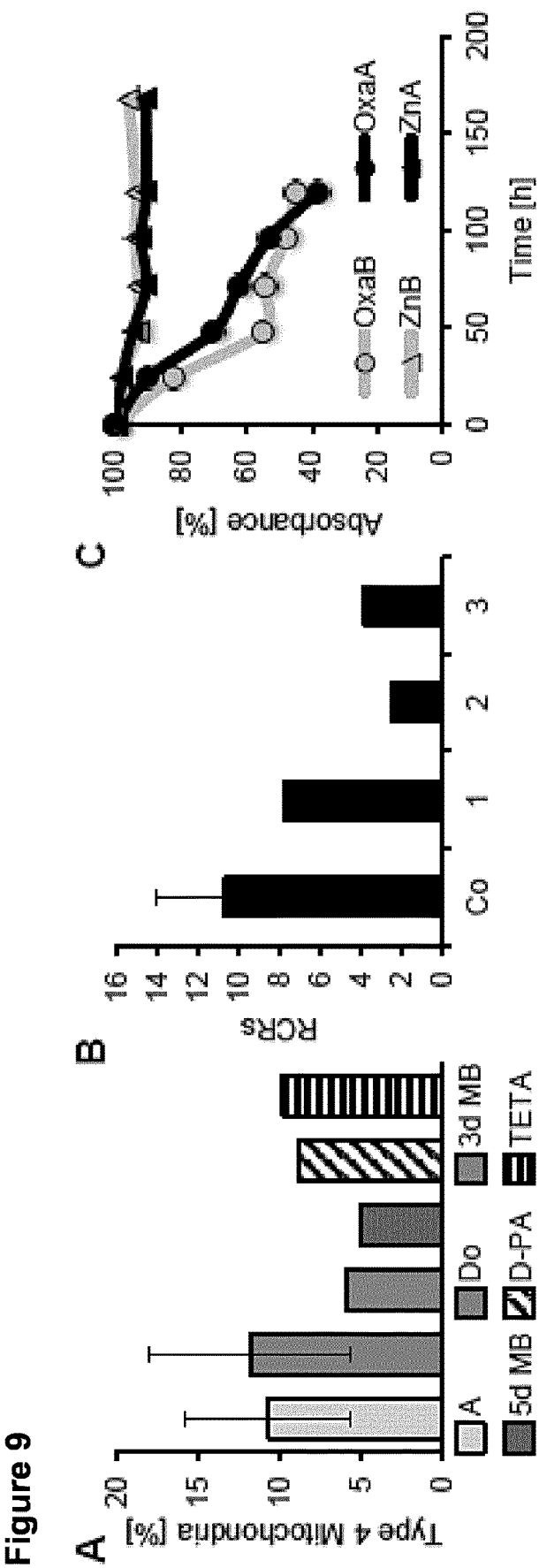

HepG2 cells were kept in MEM with 2% FCS. We found that Zn-MB is time stable at 37° C. in contrast to metal-free methanobactin (FIG. 9C). Therefore, Zn-MB, generated by preparing a 20 mM MB solution and adding an equimolar concentration of Zn solution under pH control, was used in cell culture experiments.

Neutral red cell toxicity assay was done as described elsewhere (Repetto et al., Nat Protoc 3, 1125-1131 (2008)). In brief, $2 \times 10^4$ cells were incubated for 24 hours either with medium alone (containing 2% FCS, negative control), 0.05 to 1 mM Zinc-MB, or 0.25 mM CCCP as mitochondriotoxic positive control and subsequently analyzed by neutral red.

For immunofluorescence staining, $2 \times 10^4$ cells were incubated with either medium alone, 500 µM MB or 250 µM CCCP in black 96-well plates with clear glass bottom. Staining was done by 1.6 µM Hoechst 33342 (ex 360-400 nm, em 410-480 nm), 300 nM MitoTracker® red (ex 620-640 nm, em 650-760 nm), and 1 µM nonyl acridine orange (NAO, ex 460-490 nm, em 500-550 nm) for 40 minutes at 37° C. After a washing step, fluorescence was analyzed.

To determine the cellular de-coppering efficiency of MB, cells were pretreated with 2% FCS containing medium or 15 µM copper-histidine for 24 h and subsequently subjected to a 24 h treatment with 500 µM MB. Thereafter, cells were washed two times and counted. Copper in $2.5 \times 10^6$ cells was determined by ICP-OES after wet ashing of samples with 65% nitric acid.

Cellular MB uptake was determined from cell lysates incubated for 2 or 24 h with MB at different concentrations by a competitive ELISA using a monoclonal anti-MB antibody.

Generation of HLC from Wilson Disease Patients

Urinary epithelial cells were pelleted at 400×g for 10 min from freshly donated mid-stream urine (Zhou et al., J Am Soc Nephrol 22, 1221-1228 (2011)). Cells were cultured in urinary cell medium (UCM) consisting of Dulbecco's modified Eagle medium/Ham's F-12 culture medium (DMEM/F12, Lonza) supplemented with 10% fetal bovine serum (FBS, PAA), 0.1 mM non-essential amino acids (NEAA, Sigma), 0.1 mM β-mercaptoethanol, 1 mM GlutaMAX (Life Technologies), and SingleQuot Kit CC-4127 REGM (Lonza). Urinary epithelial cells were reprogrammed by nucleofection of episomal expression vectors pCXLE-hOCT3/4-shp53-F, pCXLE-hSK, and pCXLE-hUL (Addgene) using the Amaxa Basic Nucleofector Kit (Lonza, VPI-1005). iPS cells (iPSCs) were maintained on Matrigel-coated plates in mTeSR cell culture medium and dissociated with 1 U/ml dispase (Stem Cell Technologies) into small clusters and subcultured every 5 to 7 days. WD iPSCs were differentiated into hepatocyte-like cells (HLCs) by a modification of the method reported previously (Basma et al., Gastroenterology 136, 990-999 (2009)). $5 \times 10^4$ iPSCs were plated in single cells onto 6-well plates precoated with Matrigel. The next day, the medium was changed to DMEM/F12 enriched with 100 ng/ml recombinant Activin-A (Peprotech), 100 ng/ml fibroblast growth factor-2 (FGF2, Peprotech) plus 50 ng/ml recombinant human Wnt3a (R&D Systems). Subsequently, medium was changed according to standard protocols up to day 14 (Basma et al., log. cit.). Cells were characterized by flow cytometry and by qRT-PCR analysis to assess typical markers of hepatocyte lineage.

HLCs were incubated at day 14 with Cu-histidin (15 µM) for 24 h in a 6 well plate. The following day, medium was removed and changed to OptiMEM containing MB (300 µM). After 24 h incubation, washed cells were collected, counted and their copper content assessed.

Methanobactin (MB) Antibody Generation and Competitive ELISA

Lou/c rats were immunized subcutaneously and intraperitoneally with a mixture of MB coupled to ovalbumine (50 µg) (Squarix, Marl, Germany), 5 nmol CPG oligonucleotide (Tib Molbiol, Berlin), 500 µl PBS and 500 µl incomplete Freund's adjuvant. A boost without adjuvant was given six weeks after the primary injection. Fusion was performed using standard procedures. Tissue culture supernatants (TCS) were tested in a solid-phase immunoassay with MB coupled to BSA or an irrelevant peptide coupled to BSA coated ELISA plates at a concentration of 4 µg/ml. Antibodies (mAb) from TCS bound to MB were detected with HRP conjugated mAbs against the rat IgG isotypes (T1B173 IgG2a, T1B174 IgG2b, T1B170 IgG1 all from ATCC, R-2c IgG2c homemade), thus avoiding mAbs of IgM class. HRP was visualized with ready to use TMB (1-Step™ Ultra TMB-ELISA, Thermo). 86 hybridomas that reacted specifically with MB were frozen and the antibody containing TCS were used for further analysis.

Competitive ELISA. All 86 TCS were diluted 1:10 with buffer (PBS, 5% FCS, 0.01% sodium acide). 50 µl of each TCS were pre-incubated with 50 µl MB solution (1000 ng/ml in buffer) or buffer overnight. The experiments were run in duplicates. 50 µl of the pre-incubated sample were added to ELISA plates coated with MB as used for screening. After 10 min, the plates were washed, bound antibodies against MB were detected with HRP conjugated mAbs against the rat IgG isotypes and HRP was visualized with TMB. MAbs that recognized free MB (no signal when pre-incubated with MB, positive signal in the buffer control) were further analyzed in a serial dilution of MB (1000 ng/ml to 2 ng/ml). The four mAbs that best recognized free MB were established (10610, 12D9, 18H7, 21G5, all of rat IgG2a subclass). To increase the sensitivity of the test system, the TCS of the established hybridomas were titrated on ELISA plates coated with MB. The titer of 101310 was far better (1:1260) than of 12D9 (1:320), 18H7 (1:10) and 21G5 (1:320).

For the test system 10610 was used at a dilution of 1:500 and the pre-incubation time reduced to one hour.

Metal Content Determination

Copper in liver homogenates, cell lysates and mitochondrial preparations were analyzed by ICP-OES (Ciros Vision, SPECTRO Analytical Instruments GmbH) after wet ashing of samples with 65% nitric acid (Zischka et al., log. cit.).

Miscellaneous

Electron microscopy of liver tissues and mitochondria was done as previously described32. For structural analyses of isolated mitochondria, they have been grouped into type 1: normal structured mitochondria of the "condensed" type (Hackenbrock, J Cell Biol 37, 345-369 (1968)), type 2: mitochondria with minor alterations like slightly increased cristae, type 3: mitochondria with massively increased cristae, and type 4: mitochondria with massive matrix condensations, matrix vacuolization, detachments of the inner boundary membrane, and severe cristae deformations. Methanobactin was isolated from the spent media of *Methylosinus trichosporium* OB3b as previously described (Bandow et al., Methods Enzymol 495, 259-269 (2011)). Endotoxin in methanobactin was detected by a kinetic chromogenic method (Charles River, Ecully, France) and was on average 4.5 IU/mg. Protein quantification was done by the Bradford assay (Bradford, Anal Biochem 72, 248-254 (1976)). Cytochrome C oxidase activity in isolated mitochondria was determined as described elsewhere (Kiebish et al., J Neurochem 106, 299-312 (2008)).

Copper Chelators and Chemicals

D-penicillamine*HCl (D-PA) was a gift from Heyl Pharma (Berlin), trientine*2 HCl (TETA) was from Sigma (Taufkirchen, Germany), tetrathiomolybdate*2 NH4 (98% pure) (TTM) was a gift from KT. Suzuki (Chiba University, Japan). CCCP was from Sigma. DPH and TMA-DPH were obtained from Life Technologies.

Statistics

Throughout this study N equals the number of analyzed animals and n equals the number of technical replicates of measurements. Data are presented as mean and SD. For Student's t-test, data were tested unpaired and 2-tailed, except for those represented in FIG. 3I (unpaired and 1-tailed). Differences were considered statistically significant when p-values were less than 0.05. P-values mean: $*p<0.05$, $p<0.01$, $*p<0.001$.

Example 1: Mitochondrial Impairment is Pathognomonic for Hepatic Failure in WD Patients and for Liver Damage in LPP−/− Rats Mutations causing complete functional loss of ATP7B result in severe WD phenotypes in humans (Das & Ray, Nat Clin Pract Neurol 2, 482-493 (2006)). The LPP−/− rat carries an Atp7b mutation that completely abolishes its hepatic copper transport activity (Burkhead et al. Biometals 24, 455-466 (2011)). These animals rapidly progress from a copper-burdened liver to hepatic failure and death (Zischka, loc. cit.). The diseased livers from untreated patients with acute onset of WD (who had undergone liver transplantation) were compared with the livers from LPP−/− rats with progressive disease states (FIG. 1). In addition, livers from WD patients that had received unsuccessful D-PA treatment before transplantation were included in this study (FIG. 6D).

To compare clinical stages of liver impairment, rats at ages of 80-100 days were classified, when liver damage becomes apparent, into three groups: (1) those rats "affected" by elevated liver copper, with serum AST<200 U/L, bilirubin <0.5 mg/dl, (2) rats showing "disease onset" with AST22 200 U/L, bilirubin <0.5 mg/dl and, (3) "diseased" rats with AST22 200 U/L, bilirubin >0.5 mg/dl (FIG. 10 A).

Identical tissue damage features were observed in livers of untreated WD patients and diseased LPP−/− livers (FIG. 1A). Fibrosis was observed in all WD patient livers, and beginning fibrosis was found in livers from diseased LPP−/− rats (FIG. 6A). These characteristics were absent from heterozygous LPP+/− control livers but steadily progressed in LPP−/− rats (FIG. 6B).

Another striking analogy between the livers from LPP−/− rats and WD patients was the structural damage of mitochondria (FIG. 1B and FIGS. 6C, D). Transparent vacuoles of varying sizes containing amorphous but also electron-dense material, separated inner and outer membranes, marked differences in electron densities and cristae dilations were observed (FIG. 1B and FIGS. 6C, D) depicting the typical WD mitochondrial phenotype20. Importantly, highly comparable levels of copper were found in liver homogenate and mitochondria obtained from diseased LPP−/− rats and untreated WD patient livers (FIG. 10). In contrast, lower copper content was present in the tissue homogenate from the explanted livers and isolated mitochondria of the D-PA pre-treated WD patients. This coincided with more heterogeneous impairment of the mitochondrial structure (FIG. 6D), which probably results from zonal heterogeneities originating from massive fibrosis within these livers (FIG. 6D).

Example 2: Increasing Copper Load Impairs the Mitochondrial Membrane Integrity and Function Mitochondrial copper content progressively increases with disease state in livers from LPP−/− rats (FIG. 10, FIG. 10 A). This is paralleled by increasingly severe membrane deficits, as demonstrated directly at the level of freshly isolated mitochondria (FIG. 2):

A drastic decrease in structurally normal rat liver mitochondria (type 1 and 2) in LPP−/− vs. controls and a corresponding increase in the number of structurally altered organelles (type 3 and 4, FIG. 2A) was observed.

Membrane polarization measurements with the fluorophores DPH and TMA-DPH (Prendergast et al. Biochemistry 20, 7333-7338 (1981)) revealed an alteration of the mitochondrial membrane "fluidity" at the polar head groups of the membrane lipid-water interface (TMA-DPH), but not at the membrane inner lipid phase (DPH) (FIG. 2B).

Upon induction of the mitochondrial permeability transition (MPT) by either calcium or copper, control mitochondria underwent large amplitude swelling (Zischka, loc. cit.), which was significantly reduced in mitochondria from diseased and disease onset LPP−/− rats (FIG. 2C).

The capacity of Cys-A to block calcium-induced MPT was significantly impaired in LPP−/− vs. control mitochondria (FIG. 2D).

The time stability of the inner mitochondrial transmembrane potential ($\Delta\psi$) was jeopardized, and LPP−/− mitochondria lost their membrane potential at earlier time points compared to control mitochondria (FIG. 2E).

LPP−/− mitochondria were found to have an impaired capacity to produce ATP (FIG. 9F).

Figure 7:
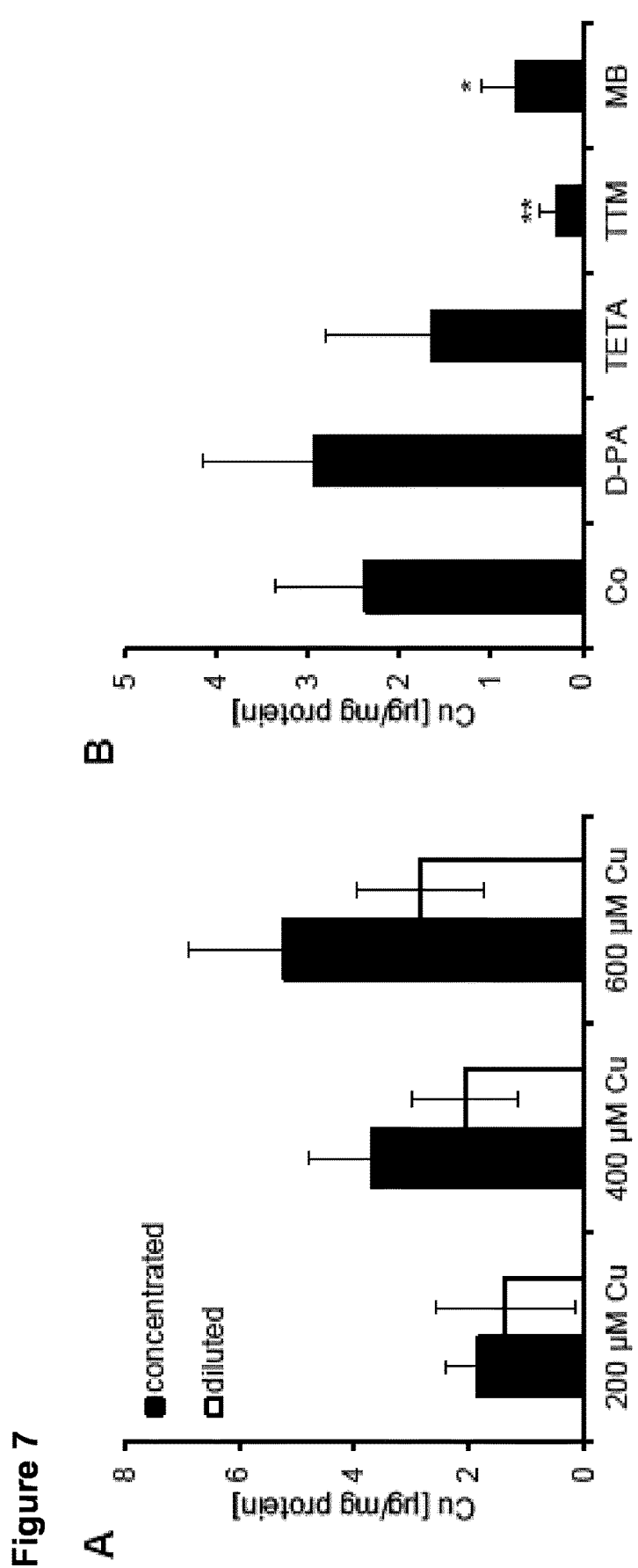
Figure 7:
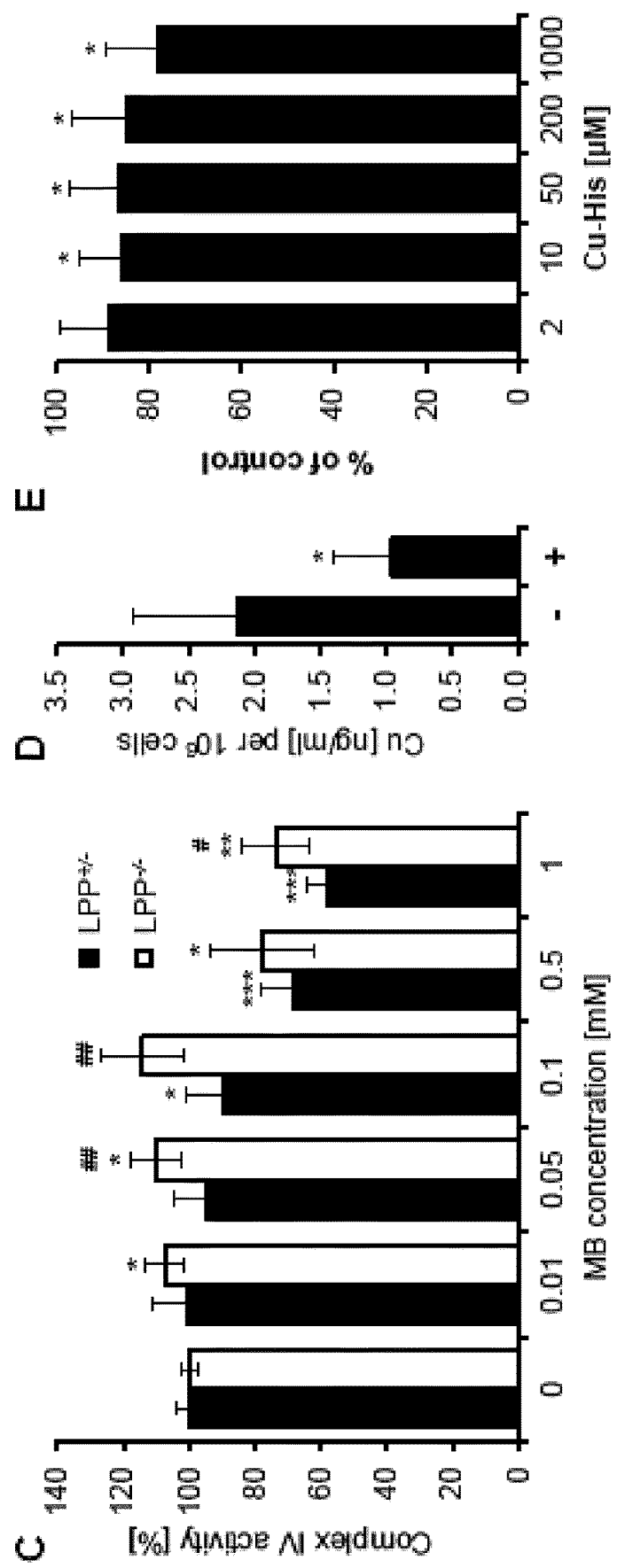

Example 3: The Bacterial Peptide Methanobactin Rapidly Depletes Accumulated Mitochondrial Copper Capability of methanobactin (MB) to existing clinically approved copper chelators D-PA, TETA and the candidate drug TTM to remove copper from freshly isolated LPP−/− mitochondria were compared. The MB peptide has an exceptionally high copper affinity and is produced by methane-oxidizing bacteria when grown in a copper poor environment (Kim et al., Science 305, 1612-1615 (2004)). In contrast to D-PA and TETA, both MB and TTM rapidly decreased copper associated with LPP−/− mitochondria (FIG. 3A). Similar results were obtained with mitochondria from wild-type rats artificially pre-loaded with copper (FIGS. 7A, B). Furthermore, MB was found to be significantly less toxic than TTM when assessing the impairment of the vital copper-dependent mitochondrial respiratory complex IV (FIGS. 3B, 7C).

Even a specific MB peptide such as mb-SB2 from *Methylocystis* strains SB2, which is structurally and chemically deviating from other MB peptides (f.e. from mb-OB3b derived from *Methylosinus trichosporium* OB3b), acts as a promising copper chelator compared to existing clinically approved copper chelators such as D-PA. In three different LPP−/− rats freshly isolated mitochondria (ATP7B−/−) were incubated 30 minutes with 1 mM cooper chelator D-PA, mb-OB3b and mb-SB2 and their chelation potency was investigated compared to the buffer treated control. In all three LPP−/− rats mitochondria MB peptide mb-SB2 decreased at least as effective as the MB peptide mb-OB3b derived from *Methylosinus trichosporium* OB3b.

Example 4: Methanobactin Efficiently De-Coppers Hepatocytes with Low Cell Toxicity At the cellular level, overnight MB treatments caused a 50% reduction of copper in HepG2 cells with either basic copper (FIG. 7D) or preloaded with copper amounts that exhibit only mild toxicity (FIGS. 3C, 7E). Moreover, in an attempt to test the efficacy of MB on WD patient samples, urinary epithelial cells from these patients were reprogrammed into induced pluripotent stem cells (iPSC) and differentiated into hepatocyte-like cells (HLC, FIGS. 7F-I). Comparable copper depletions upon MB treatment were found in both copper-preloaded HepG2 and HLCs (FIG. 3C).

Using a monoclonal antibody specific for MB, MB was found to be taken up in a dose dependent manner by HepG2 cells (FIG. 3D). Unwarranted cytotoxic effects of MB were only observed at millimolar MB concentrations (FIG. 3E). At the mitochondrial level, non-toxic MB concentrations (500 µM) reduced the mitochondrial membrane potential only partially (FIG. 3F). Thus, MB efficiently de-coppers hepatocytes without major toxic side effects.

Example 5: Methanobactin Directs Liver Copper into Bile

Figure 8:
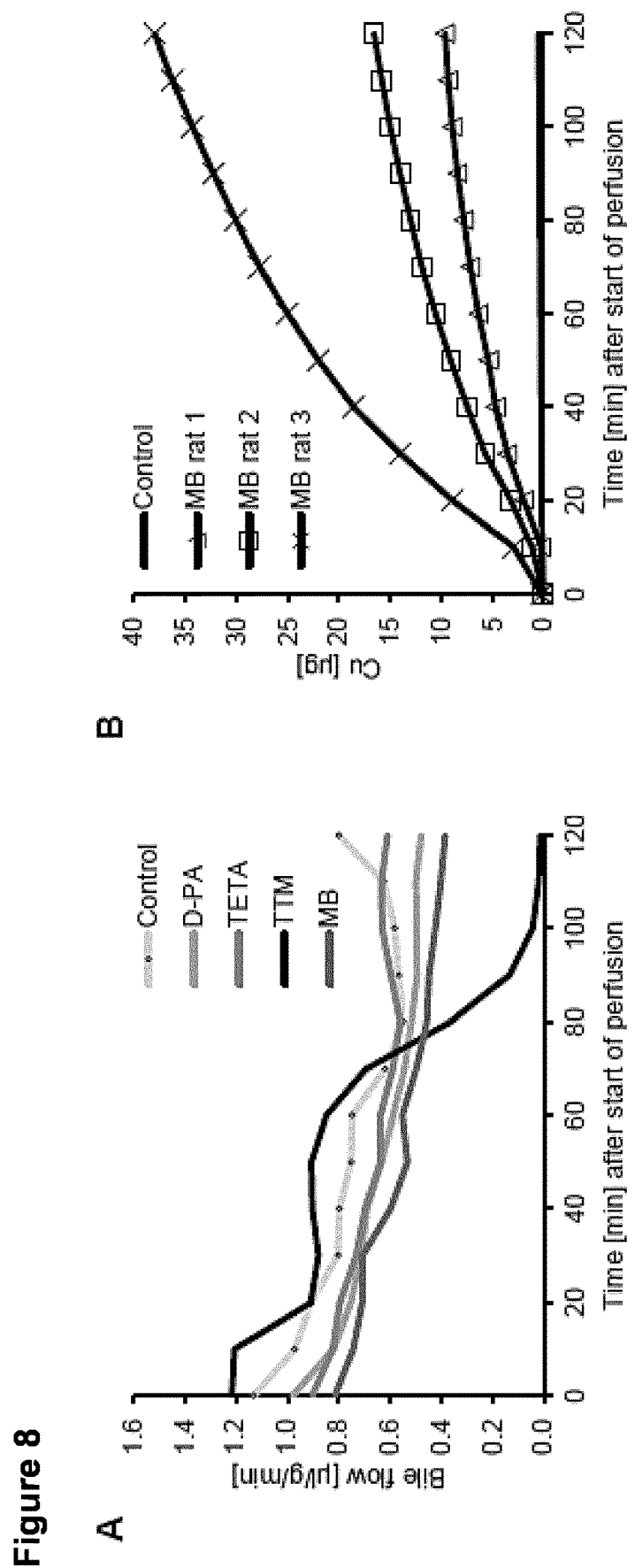
Figure 8:
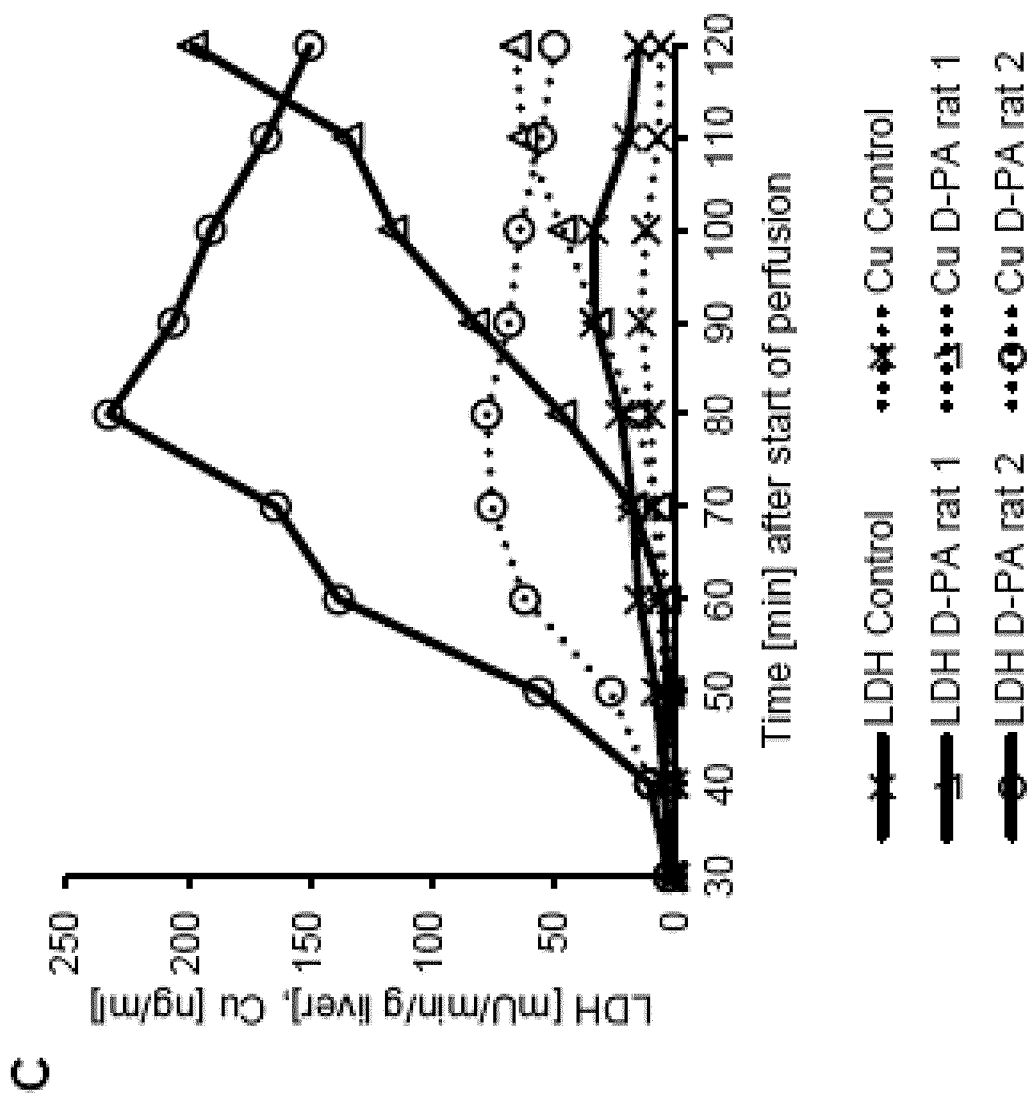

The copper removing efficiency of MB was further validated at the whole organ level (FIG. 3G-I). During a two-hour perfusion of LPP−/− livers, tenfold higher amounts of copper were released into bile, the major physiological excretion route for copper (Ferenci, Clinical gastroenterology and hepatology: the official clinical practice journal of the American Gastroenterological Association 3, 726-733 (2005)), in the presence of MB in comparison to TTM (FIG. 3G, FIGS. 8A, B). D-PA and TETA did not provoke any detectable release of copper into the bile (FIG. 3G). However, all chelators, except TTM, caused an increased presence of copper in the perfusate (FIG. 3H), which may be linked to TTMs ability to precipitate copper intra-cellularly (Ogra et al., Toxicology 106, 75-83 (1996)). The release of copper into the perfusate was partly dependent on the liver disease state, as the liver damage marker LDH paralleled the copper release curves (FIG. 8C). Noteworthy, only MB significantly reduced the copper content of the LPP−/− livers within the two hour perfusion (FIG. 3I).

Example 6: Short-Term Methanobactin Application Reverses Liver Damage in Vivo

The efficiency of a short-term MB treatment schedule was assessed in LPP−/− rats at the age of liver disease onset (85-90 days). Animals received MB (i.p.) either for 3 or 5 days or the clinically used copper chelators D-PA or TETA, which were orally administered for 4-days.

MB application resulted in a strong reduction of histopathological liver damage markers in LPP−/− livers (FIG. 4A), in contrast to treatment with D-PA or TETA. The latter two chelators were unable to avoid the increase of serum AST levels (indicative of progressive liver damage, FIG. 4B) meaning that short-term D-PA or TETA treatments were without therapeutic effect. In contrast, in six out of seven MB treated LPP−/− rats, AST levels markedly decreased (FIG. 4B) and animals regained body weight (FIG. 10B). Importantly, after 5 days of MB treatment, two LPP−/− animals with onset disease and one diseased LPP−/− rat were rescued from liver dysfunction (AST<200 U/L, FIG. 4B, FIG. 10B).

Concerning drug safety, control LPP+/− rats treated with MB did not exhibit any signs of toxicity and body weight, liver copper concentration, serum AST and bilirubin values remained within the physiological range (N=4, data not shown). Furthermore, MB was detectable in the serum for only 30 minutes (FIG. 4C).

MB induced a progressive reduction in total liver copper, which was even more pronounced in the mitochondrial compartment (FIG. 4D). No copper reduction was found upon treatment with D-PA or TETA, neither in whole liver nor in purified mitochondria (FIG. 4D). The mitochondrial de-coppering effect of MB was confirmed by ultra-structural examinations (FIG. 4E). Severely impaired mitochondria (type 4, FIG. 2A) were almost absent in isolates from MB treated LPP−/− animals, but not in isolates from D-PA or TETA treated animals (FIG. 4E, quantitation in FIG. 9A).

How long does a short-term MB treatment postpone the onset of acute liver failure? To address this issue, three LPP−/− rats were treated with MB for five days and subsequently set on MB drug holiday. Starting with the MB treatment, zinc enriched food (1000 ppm) (Halestrap, Biochem Soc Trans 38, 841-860 (2010)) was given, as zinc is a clinically relevant copper maintenance therapy in WD12. All MB-treated animals showed restoration of normal serum AST, lasting for at least two weeks, thereafter AST levels rose again (FIG. 5A). At the time of analysis, one animal was still healthy and two animals manifested different stages of liver disease (FIGS. 5A, C). The degree of liver damage correlated with mitochondrial (but not whole liver) copper levels (FIG. 5B), as well as with structural (FIG. 5D) and functional defects in mitochondria (FIG. 9B).

Intraperitoneal (i.p.) or intravenous (i.v.) MB-application routes may be alternatively used (FIGS. 10B and C). For i.v. injections, three LPP−/− rats were catheterized into the femoral vein. After a three-day recovery period, animals received daily MB doses on five consecutive days. All animals regained bodyweight and, in cases with elevated AST or bilirubin, levels returned to normal (FIG. 10O). Moreover, a profound reduction in copper content was found at the levels of the whole liver and purified mitochondria (FIG. 10O).

Example 7: Methanobactin for the Treatment of Acute Liver Failure

The capacity of MB was assessed to rescue diseased LPP−/− rats by an "acute rescue regimen" consisting of two daily MB injections for one week (i.e. 16 i.p. injections in total, FIG. 10D). Four LPP−/− rats with strongly elevated AST levels were treated (FIG. 10D). All animals survived, regained weight and presented with normal serum AST and bilirubin and exceptionally low copper values at the end of the treatment regimen (FIG. 10D). This powerful therapeutic effect is best exemplified by the case of animal no. 3 (FIG. 10D). Diseased LPP−/− rats presenting with progressive weight loss and bilirubin levels greater than 8 mg/dl (FIG. 10A) must be considered as moribund as such animals usually die within few days. In contrast, following the "acute rescue regimen", animal no. 3 regained 29% in weight, demonstrated a drastic decrease in AST and bilirubin levels down to normal, hepatic copper depletion, associated with massive structural and functional mitochondrial recovery (FIG. 10D, FIG. 9D-F).

Example 8: Repetetive Mb Treatment

Due to the efficiency of the short-term MB treatment, we did a first test aiming at replacing daily chelation therapy by a regimen consisting of repetitive treatment cycles interrupted by longer observation cycles (FIG. 14). Five LPP−/− rats as well as five age- and sex-matched LPP+/− controls were included. One pair of rats was sacrificed at experimental days 1, 8, 29, 36 and 85, respectively. At experimental day one, all animals were healthy, with the sacrificed LPP−/− rat demonstrating a pronounced liver and mitochondrial copper load and a slightly impaired mitochondrial function (87% ATP production capacity) in comparison to its LPP+/− control (pair 1). The four remaining LPP−/− rats were subjected to the first treatment cycle consisting of three daily MB injections (i.p.) for five days. All animals stayed healthy and this resulted in a 40% reduction in copper load at experimental day eight (pair 2), which increased back to starting levels after additional three weeks of observation (day 29, pair 3). Upon the second treatment cycle copper loads decreased again, but now down to 25% of the starting values, resulting in an unprecedented low copper load in LPP−/− mitochondria (day 36, pair 4). This decoppering efficiency of 75% was associated with a subsequent observation period of further seven weeks during which the remaining LPP−/− rat stayed healthy. At experimental day 85, liver and mitochondrial copper loads had risen back to values before beginning of the treatment (day 1), associated with an impaired mitochondrial function (65% ATP production capacity) in comparison to its LPP+/− control (pair 5). This corresponds to a doubling of the age when untreated LPP−/− rats become diseased.

The invention claimed is:

1. A method of treating Wilson Disease in a subject, the treatment comprising at least one treatment cycle of (a) a first phase of a copper-binding methanobactin administration followed by (b) a second phase of non-treatment, wherein the second phase exceeds the first phase lasting for a period of at least 2 weeks and wherein said methanobactin comprises the following general formula (I):

$$R^1-(X)_{2-5}-R^2 \quad (I)$$

wherein
R$^1$ and R$^2$ are each a 5-membered heterocycle comprising N and associated with an enethiolate;
and each X is independently selected from any amino acid.

2. The method of claim 1, wherein the first phase lasts for a period of 1, 2, 3, 4, 5, 6, 7, 8, 9, 10 or more consecutive days.

3. The method of claim 1, wherein the methanobactin is administered in single doses once daily, twice daily, three times daily, four times daily, every other day or continuously.

4. The method of claim 1, wherein the second phase of said treatment cycle is followed by at least one further treatment cycle, and/or wherein the method of treatment comprises recurrent treatment cycles.

5. The method of claim 1, wherein Wilson Disease comprises acute phase Wilson Disease.

6. The method of claim 5, wherein acute phase Wilson Disease is characterized by acute liver failure.

7. The method of claim 1, wherein the methanobactin is administered in a dosage of at least 1 mg/kg body weight to the subject.

8. The method of claim 1, wherein said methanobactin binds Cu(I) with a K$_d$ of 10$^{-15}$ or less and/or wherein treatment comprises at least one treatment cycle comprising administration of a methanobactin binding Cu(I) with a K$_d$ of 10$^{-15}$ or less, and at least one treatment cycle comprising administration of a methanobactin binding Cu(I) with a K$_d$ of 10$^{-15}$ or more.

9. The method of claim 1, wherein said methanobactin is derived from bacteria, and/or wherein said methanobactin is selected from (a) a *Methylosinus trichosporium* OB3b methanobactin (mb-OB3b) (b) a *Methylocystis* strain SB2 methanobactin (mb-SB2), (c) a *Methylococcus capsulatus* Bath methanobactin (mb-Bath) (d) a *Methylomicrobium album* BG8 methanobactin (mb-BG8), (e) a *Methylocystis* strain M methanobactin, (f) a *Methylocystis hirsuta* CSC1 methanobactin (g) a *Methylocystis rosea* methanobactin (mb-*rosea*), (h) a *Methylosinus* sp. strain LW3 methanobactin (mb-LW3), (i) a *Methylosinus* sp. strain LW4 methanobactin (mb-LW4), (j) a *Methylocystis* sp. strain LW5 (mb-LW5) methanobactin, (k) a *Methylosinus* sp. strain PW1 methanobactin (mb-PW1), (l) a *Methylocystis parvus* OBBP methanobactin (mb-OBBP), (m) a *Cupriavidus basiliensis* B-8 methanobactin (mb-B-8), (n) a *Pseudomonas extremaustralis* 14-3 methanobactin (mb-14-3), (o) a *Azospirillum* sp. stain B510 methanobactin (mb-B510), (p) a *Tistrella mobilis* KA081020-065 (mb-*mobilis*) methanobactin and (q) a *Comamonas composti* DSM 21721 methanobactin (mb-21721); wherein mb-OB3b is of the formula R$^1$GSCYR$^2$SCM (II), wherein R$^1$ is selected from (N-2-isopropylester-(4-thionyl-5-hydroxy-imidazole) and N-2-isopropylester-(4-thiocarbonyl-5-hydroxy-imidazolate), and R$^2$ is selected from pyrrolidine-(4-hydroxy-5-thionyl-imidazole) and pyrrolidine-(4hydroxy-5-thiocarbonyl-imidazolate), and mb-SB2 is of the formula R$^1$ASR$^2$AA (III) wherein R$^1$ is 4-guanidinobutanoyl-imidazole and R$^2$ is 1-amino-2-hydroxy-oxazolone.

10. The method of claim 9, wherein said mb-OB3b has the formula (IV) or said mb-SB2 has formula (V), wherein said mb-OB3b comprises structure (VI) or said mb-SB2 comprises structure (VII).

11. The method of claim 1, wherein said methanobactin is provided in stabilized form, wherein said methanobactin is in the form of a complex with Zn(I) and/or Zn(II) and/or is provided at a pH≥9.

12. A method of treating Wilson Disease, cancer, neurodegenerative diseases, diabetes, bacterial infections, inflammatory diseases, fibrosis, cirrhosis, familiar amyotrophic lateral sclerosis, lead and/or mercury poisoning, the method comprising administering a pharmaceutical composition to a subject in need thereof wherein the composition comprises a stabilized methanobactin, wherein said methanobactin is in the form of a complex with Zn(I) and/or Zn(II) and/or said pharmaceutical composition is provided at a pH≥9, comprising a stabilized methanobactin-complex with Zn(I) and/or Zn(II) being prepared contacting an amount of Zn(I) and/or Zn(II) and an amount of methanobactin in a ratio of 1:1 in aqueous solution.

13. The method of claim 12, wherein the bacterial infections are favorable for human fungal pathogens, wherein said human fungal pathogen is *Candida albicans*.

14. The method of claim 1 wherein treatment reduces at least one of the following (i) whole liver copper levels, (ii) overall hepatocyte copper levels and/or (iii) hepatocyte mitochondrial copper levels; and/or wherein treatment results in excretion of copper via the bile.

15. The method of claim 12 wherein treatment reduces at least one of the following (i) whole liver copper levels, (ii) overall hepatocyte copper levels and/or (iii) hepatocyte mitochondrial copper levels; and/or wherein treatment results in excretion of copper via the bile.

16. A method of treating Wilson Disease in a subject, wherein the treatment comprising at least one treatment cycle of (a) a first phase of methanobactin administration followed by (b) a second phase of non-treatment, wherein the second phase exceeds the first phase, wherein said methanobactin comprises a *Methylocystis* strain SB2 methanobactin (mb-SB2).

17. The method of claim 16, wherein the first phase lasts for a period of 1, 2, 3, 4, 5, 6, 7, 8, 9, 10 or more consecutive days.

18. The method of claim 16, wherein the methanobactin is administered in single doses once daily, twice daily, three times daily, four times daily, every other day or continuously.

19. The method of claim 16, wherein the second phase lasts for a period of at least 1 week, 2 weeks, 3 weeks, 4 weeks, 5 weeks or more.

20. The method of claim 16, wherein the second phase of said treatment cycle is followed by at least one further treatment cycle, and/or wherein the method of treatment comprises recurrent treatment cycles.

21. The method of claim 16, wherein Wilson Disease comprises acute phase Wilson Disease.

22. The method of claim 21, wherein acute phase Wilson Disease is characterized by acute liver failure.

23. The method of claim 16, wherein the methanobactin is administered in a dosage of at least 1 mg/kg body weight to the subject.

24. The method of claim 16, wherein said methanobactin binds Cu(I) with a $K_d$ of $10^{-15}$ or less and/or wherein treatment comprises at least one treatment cycle comprising administration of a methanobactin binding Cu(I) with a $K_d$ of $10^{-15}$ or less, and at least one treatment cycle comprising administration of a methanobactin binding Cu(I) with a $K_d$ of $10^{-15}$ or more.

25. The method of claim 16, wherein said mb-SB2 is of the formula $R^1ASR^2AA$ (III) wherein $R^1$ is 4-guanidinobutanoyl-imidazole and $R^2$ is 1-amino-2-hydroxy-oxazolone.

26. The method of claim 25, wherein said mb-SB2 has the formula (V).

27. The method of claim 16, wherein said mb-SB2 comprises or consists of the following structure (VII).

28. The method of claim 16, wherein said methanobactin is provided in stabilized form, wherein said methanobactin is in the form of a complex with Zn(I) and/or Zn(II) and/or is provided at a pH≥9.

29. The method of claim 12, wherein the cancer comprises reticulum cell sarcoma, bronchogenic and laryngeal squamous cell carcinomas, cervical cancer, breast cancer, colorectal cancer, stomach cancer, lung cancer, liver cancer, prostate cancer, brain cancer, chronic lymphoid leukemia, non-Hodgkin's lymphoma, multiple myeloma and Hodgkin's lymphoma.

30. The method of claim 12, wherein the neurodegenerative diseases comprise Parkinson Disease, Alzheimer Disease, Prion Disease, Huntington Disease and familiar amyotrophic lateral sclerosis (fALS).

31. A method of treating Wilson Disease in a subject, the treatment comprising at least one treatment cycle of (a) a first phase of a copper-binding methanobactin administration followed by (b) a second phase of non-treatment, wherein the second phase exceeds the first phase lasting for a period of at least 2 weeks and wherein said methanobactin comprises the following general formula (I):

wherein
$R^1$ and $R^2$ are each a 5-membered heterocycle comprising N; and each X is independently selected from any amino acid.

* * * * *

SEQUENCE LISTING

```
<160> NUMBER OF SEQ ID NOS: 18

<210> SEQ ID NO 1
<211> LENGTH: 30
<212> TYPE: PRT
<213> ORGANISM: Methylosinus sp.
```

-continued

<400> SEQUENCE: 1

Met Thr Val Lys Ile Ala Gln Lys Lys Val Leu Pro Val Ile Gly Arg
1               5                   10                  15

Ala Ala Ala Leu Cys Gly Ser Cys Tyr Pro Cys Ser Cys Met
            20                  25                  30

<210> SEQ ID NO 2
<211> LENGTH: 34
<212> TYPE: PRT
<213> ORGANISM: Methylosinus sp.

<400> SEQUENCE: 2

Met Ala Ile Lys Ile Ala Lys Lys Glu Val Leu Pro Val Val Gly Arg
1               5                   10                  15

Leu Gly Ala Met Cys Ser Ser Cys Pro Met Cys His Cys Gly Pro Leu
            20                  25                  30

Cys Pro

<210> SEQ ID NO 3
<211> LENGTH: 32
<212> TYPE: PRT
<213> ORGANISM: Methylocystis sp.

<400> SEQUENCE: 3

Met Ala Ile Lys Ile Ser Lys Lys Glu Val Leu Pro Val Val Gly Arg
1               5                   10                  15

Leu Gly Ala Met Cys Ser Ser Cys Pro Met Cys Gly Pro Leu Cys Pro
            20                  25                  30

<210> SEQ ID NO 4
<211> LENGTH: 32
<212> TYPE: PRT
<213> ORGANISM: Methylosinus sp.

<400> SEQUENCE: 4

Met Ala Ile Lys Ile Ala Lys Lys Glu Val Leu Pro Val Val Gly Arg
1               5                   10                  15

Leu Gly Ala Met Cys Ser Ser Cys Pro Met Cys Gly Pro Leu Cys Pro
            20                  25                  30

<210> SEQ ID NO 5
<211> LENGTH: 31
<212> TYPE: PRT
<213> ORGANISM: Methylosinus sp.

<400> SEQUENCE: 5

Met Thr Ile Lys Val Val Lys Lys Glu Ile Leu Pro Val Ile Gly Arg
1               5                   10                  15

Val Gln Ala Met Cys Ala Cys Asn Pro Pro Trp Cys Gly Thr Cys
            20                  25                  30

<210> SEQ ID NO 6
<211> LENGTH: 35
<212> TYPE: PRT
<213> ORGANISM: Methylocystis sp.

<400> SEQUENCE: 6

Met Ala Ile Lys Ile Val Lys Lys Glu Ile Leu Pro Val Ile Gly Arg
1               5                   10                  15

Val Gln Ala Phe Cys Ser Ser Asp Ser Gly Gly Gly Gln Ile Gly Cys

-continued

```
                  20                  25                  30

Gly Pro Ala
        35

<210> SEQ ID NO 7
<211> LENGTH: 30
<212> TYPE: PRT
<213> ORGANISM: Methylocystis sp.

<400> SEQUENCE: 7

Met Thr Ile Arg Ile Ala Lys Arg Ile Thr Leu Asn Val Ile Gly Arg
1               5                   10                  15

Ala Ser Ala Arg Cys Ala Ser Thr Cys Ala Ala Thr Asn Gly
            20                  25                  30

<210> SEQ ID NO 8
<211> LENGTH: 30
<212> TYPE: PRT
<213> ORGANISM: Methylocystis sp.

<400> SEQUENCE: 8

Met Thr Ile Arg Ile Ala Lys Arg Ile Thr Leu Asn Val Ile Gly Arg
1               5                   10                  15

Ala Ser Ala Arg Cys Ala Ser Thr Cys Ala Ala Thr Asn Gly
            20                  25                  30

<210> SEQ ID NO 9
<211> LENGTH: 30
<212> TYPE: PRT
<213> ORGANISM: Methylocystis sp.

<400> SEQUENCE: 9

Met Thr Ile Arg Ile Ala Lys Arg Ile Thr Leu Asn Val Ile Gly Arg
1               5                   10                  15

Ala Ser Ala Met Cys Ala Ser Thr Cys Ala Ala Thr Asn Gly
            20                  25                  30

<210> SEQ ID NO 10
<211> LENGTH: 27
<212> TYPE: PRT
<213> ORGANISM: Methylocystis sp.

<400> SEQUENCE: 10

Met Thr Ile Lys Ile Val Lys Arg Thr Ala Leu Ala Val Asn Gly Arg
1               5                   10                  15

Ala Gly Ala Asp Cys Gly Thr Ala Cys Trp Ala
            20                  25

<210> SEQ ID NO 11
<211> LENGTH: 27
<212> TYPE: PRT
<213> ORGANISM: Methylocystis sp.

<400> SEQUENCE: 11

Met Ala Ile Asn Ile Val Lys Arg Thr Thr Leu Val Val Asn Gly Arg
1               5                   10                  15

Thr Gly Ala Asp Cys Gly Thr Ala Cys Trp Gly
            20                  25

<210> SEQ ID NO 12
<211> LENGTH: 27
<212> TYPE: PRT
```

<213> ORGANISM: Methylosinus sp.

<400> SEQUENCE: 12

Met Ala Ile Asn Ile Val Lys Arg Thr Thr Leu Val Val Asn Gly Arg
1               5                   10                  15

Ser Gly Ala Asp Cys Gly Thr Ala Cys Trp Gly
            20                  25

<210> SEQ ID NO 13
<211> LENGTH: 29
<212> TYPE: PRT
<213> ORGANISM: Tistrella mobilis

<400> SEQUENCE: 13

Met Ser Ile Lys Ile Ser Ala Arg Lys Ala Leu Gln Ile Ala Gly Arg
1               5                   10                  15

Ala Gly Ala Arg Cys Ala Thr Ile Cys Ala Val Ala Gly
            20                  25

<210> SEQ ID NO 14
<211> LENGTH: 30
<212> TYPE: PRT
<213> ORGANISM: Cupriavidus basiliensis

<400> SEQUENCE: 14

Met Thr Ile Lys Ile Ser Lys Lys Glu Ala Ile Glu Val Arg Gly Arg
1               5                   10                  15

Ser Gly Ala Cys Cys Gly Ser Cys Cys Ala Ala Ile Gly Ala
            20                  25                  30

<210> SEQ ID NO 15
<211> LENGTH: 31
<212> TYPE: PRT
<213> ORGANISM: Pseudomonas extremaustralis

<400> SEQUENCE: 15

Met Ser Ile Lys Ile Ala Lys Lys His Thr Leu Gln Ile Ala Gly Arg
1               5                   10                  15

Ala Gly Ala Cys Cys Ala Ser Cys Cys Ala Pro Leu Gly Val Asn
            20                  25                  30

<210> SEQ ID NO 16
<211> LENGTH: 31
<212> TYPE: PRT
<213> ORGANISM: Azospirillum sp.

<400> SEQUENCE: 16

Met Thr Ile Lys Ile Ala Lys Lys Gln Thr Leu Ser Val Ala Gly Arg
1               5                   10                  15

Ala Gly Ala Cys Cys Gly Ser Cys Cys Ala Pro Val Gly Val Asn
            20                  25                  30

<210> SEQ ID NO 17
<211> LENGTH: 31
<212> TYPE: PRT
<213> ORGANISM: Comamonas composti

<400> SEQUENCE: 17

Met Lys Ile Lys Val Thr Lys Lys Thr Thr Met Thr Val Ala Gly Arg
1               5                   10                  15

Ala Gly Ala Cys Cys Ala Ser Cys Cys Ala Pro Val Gly Val Asn
            20                  25                  30

```
<210> SEQ ID NO 18
<211> LENGTH: 35
<212> TYPE: PRT
<213> ORGANISM: Methylocystis sp.

<400> SEQUENCE: 18

Met Ala Ile Lys Ile Val Lys Lys Glu Ile Leu Pro Val Ile Gly Arg
1               5                   10                  15

Val Gln Ala Phe Cys Ser Ser Cys Ser Gly Gly Gly Gln Cys Gly Cys
            20                  25                  30

Gly Pro Ala
        35
```